(12) United States Patent
Schwarz et al.

(10) Patent No.: US 7,521,396 B2
(45) Date of Patent: Apr. 21, 2009

(54) SUBSTITUTED (THIOXO)CARBONYLA-MINOPHENYLURACILS

(75) Inventors: Hans-Georg Schwarz, Langenfeld (DE); Roland Andree, Langenfeld (DE); Dorothee Hoischen, Düsseldorf (DE); Joachim Kluth, Langenfeld (DE); Karl-Heinz Linker, Leverkusen (DE); Anton Vidal-Ferran, Barcelona (ES); Mark Wilhelm Drewes, Langenfeld (DE); Peter Dahmen, Neuss (DE); Dieter Feucht, Eschborn (DE); Rolf Pontzen, Leichlingen (DE)

(73) Assignee: Bayer CropScience AG, Monheim (DE)

( * ) Notice: Subject to any disclaimer, the term of this patent is extended or adjusted under 35 U.S.C. 154(b) by 494 days.

(21) Appl. No.: 10/514,153

(22) PCT Filed: Apr. 22, 2003

(86) PCT No.: PCT/EP03/04138

§ 371 (c)(1),
(2), (4) Date: Nov. 21, 2005

(87) PCT Pub. No.: WO03/093244

PCT Pub. Date: Nov. 13, 2003

(65) Prior Publication Data

US 2006/0089262 A1    Apr. 27, 2006

(30) Foreign Application Priority Data

May 2, 2002    (DE) .............................. 102 19 434

(51) Int. Cl.
| C07D 239/54 | (2006.01) |
| C07D 401/12 | (2006.01) |
| C07D 403/12 | (2006.01) |
| C07D 413/12 | (2006.01) |
| C07D 417/12 | (2006.01) |
| A01N 43/54 | (2006.01) |

(52) U.S. Cl. ................ 504/243; 544/311; 544/309; 544/310; 544/312

(58) Field of Classification Search ............... 544/311; 504/243

See application file for complete search history.

(56) References Cited

U.S. PATENT DOCUMENTS

| 5,084,084 | A | 1/1992 | Satow et al. | ............ 71/92 |
| 5,127,935 | A | 7/1992 | Satow et al. | ............ 71/92 |
| 5,154,755 | A | 10/1992 | Satow et al. | ............ 71/92 |
| 5,356,863 | A | 10/1994 | Satow et al. | ............ 504/243 |
| 6,303,783 | B1 * | 10/2001 | Karp | ............ 544/319 |
| 6,734,139 | B1 * | 5/2004 | Feucht et al. | ............ 504/128 |

FOREIGN PATENT DOCUMENTS

| JP | 9-48761 | 2/1997 |
| WO | 96/35679 | 11/1996 |
| WO | 97/09319 | 3/1997 |
| WO | 98/06706 | 2/1998 |
| WO | 99/21837 | 5/1999 |
| WO | 00/02867 | 1/2000 |

* cited by examiner

*Primary Examiner*—Venkataraman Balasubramanian
(74) *Attorney, Agent, or Firm*—Richard E. L. Henderson

(57) ABSTRACT

The invention relates to compounds of the formula (I)

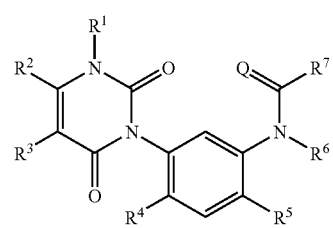

in which Q, $R^1$, $R^2$, $R^3$, $R^4$, $R^5$, $R^6$, $R^7$ are as defined in the disclosure, to processes for their preparation, and to their use as herbicides.

15 Claims, No Drawings

SUBSTITUTED (THIOXO)CARBONYLAMINOPHENYLURACILS

The present patent application has been filed under 35 U.S.C. 371 as a national stage application of PCT/EP03/04138, filed Apr. 22, 2003, which was published in German as International Patent Publication WO 03/093244 on Nov. 13, 2003, which is entitled to the right of priority of German Patent Application 102 19 434.3, filed May 2, 2002.

The invention relates to novel substituted (thioxo)carbonylaminophenyluracils, to the process for their preparation and to their use as plant treatment agents, in particular as herbicides.

Certain substituted aryluracils are already known (for example EP-A-408 382, U.S. Pat. Nos. 5,084,084, 5,127,935, 5,154,755, EP-A-563 384, U.S. Pat. No. 5,356,863, JP-A-09 048 761—cited in Chem. Abstracts 126:238387, WO 99/21837 A, U.S. Pat. No. 6,303,783). However, these compounds have hitherto not attained any particular importance since they have a number of disadvantages.

This invention now provides novel substituted (thioxo)carbonylaminophenyluracils of the general formula (I)

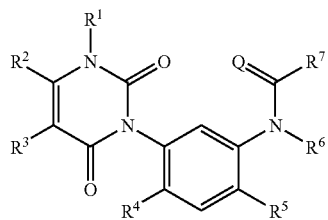

in which

Q represents oxygen or sulphur, $R^1$ represents hydrogen, amino or optionally cyano, halogen or $C_1$-$C_4$-alkoxy-substituted alkyl having 1 to 6 carbon atoms, $R^2$ represents carboxyl, cyano, carbamoyl, thiocarbamoyl or in each case optionally cyano, halogen or $C_1$-$C_4$-alkoxy-substituted alkyl or alkoxy-carbonyl having in each case 1 to 6 carbon atoms in the alkyl groups, $R^3$ represents hydrogen, halogen or optionally halogen-substituted alkyl having 1 to 6 carbon atoms, $R^4$ represents hydrogen, cyano, carbamoyl, thiocarbamoyl or halogen, $R^5$ represents cyano, carbamoyl, thiocarbamoyl, halogen, or represents in each case optionally halogen-substituted alkyl or alkoxy having in each case 1 to 6 carbon atoms, $R^6$ represents hydrogen, represents optionally cyano-, carboxyl-, halogen-, $C_1$-$C_4$-alkoxy-, $C_1$-$C_4$-alkylthio-, $C_1$-$C_4$-alkylsulphinyl-, $C_1$-$C_4$-alkylsulphonyl-, $C_1$-$C_4$-alkyl-carbonyl- or $C_1$-$C_4$-alkoxy-carbonyl-substituted alkyl having 1 to 6 carbon atoms, represents in each case optionally cyano-, halogen- or $C_1$-$C_4$-alkoxy-substituted alkylcarbonyl, alkoxycarbonyl or alkylsulphonyl having in each case 1 to 6 carbon atoms in the alkyl groups, represents in each case optionally halogen-substituted alkenyl, alkenylcarbonyl, alkenylsulphonyl or alkynyl having in each case 3 to 6 carbon atoms in the alkenyl or alkynyl groups, represents in each case optionally cyano, halogen or $C_1$-$C_4$-alkyl-substituted cycloalkyl, cycloalkylalkyl, cycloalkylcarbonyl, cycloalkylalkylcarbonyl, cycloalkylsulphonyl or cycloalkylalkylsulphonyl having in each case 3 to 6 carbon atoms in the cycloalkyl groups and, if appropriate, 1 to 4 carbon atoms in the alkyl moiety, represents in each case optionally nitro-, cyano-, halogen-, $C_1$-$C_4$-alkyl-, $C_1$-$C_4$-haloalkyl-, $C_1$-$C_4$-alkoxy-, $C_1$-$C_4$-haloalkoxy- or $C_1$-$C_4$-alkoxy-carbonyl-substituted aryl, arylalkyl, arylcarbonyl, arylalkylcarbonyl, arylsulphonyl or arylalkylsulphonyl having in each case 6 or 10 carbon atoms in the aryl groups and, if appropriate, 1 to 4 carbon atoms in the alkyl moiety, or represents in each case optionally nitro-, cyano-, halogen-, $C_1$-$C_4$-alkyl-, $C_1$-$C_4$-haloalkyl-, $C_1$-$C_4$-alkoxy-, $C_1$-$C_4$-haloalkoxy- or $C_1$-$C_4$-alkoxy-carbonyl-substituted heterocyclylcarbonyl, heterocyclylalkylcarbonyl, heterocyclylsulphonyl or heterocyclylalkylsulphonyl having in each case up to 6 carbon atoms, up to 5 nitrogen atoms and/or 1 or 2 oxygen or sulphur atoms as ring members— where the heterocyclyl groups in each case also optionally contain 1 or 2 —SO groups, 1 or 2 —$SO_2$ groups, 1 or 2 —CO groups or 1 or 2 —CS groups, and $R^7$ represents in each case optionally halogen-substituted alkoxycarbonylalkoxy, alkoxycarbonylalkylthio, alkenyloxycarbonylalkoxy, alkenyloxycarbonylalkylthio, alkynyloxycarbonylalkoxy, alkynyloxycarbonylalkylthio, carbamoylalkoxy, carbamoylalkylthio, alkylaminocarbonylalkoxy, alkylaminocarbonylalkylthio, dialkylaminocarbonylalkoxy, dialkylaminocarbonylalkylthio, N-alkyl-N-alkenylaminocarbonylalkoxy, N-alkyl-N-alkenylaminocarbonylalkylthio, dialkenylaminocarbonylalkoxy, dialkenylaminocarbonylalkylthio, N-alkyl-N-alkynylaminocarbonylalkoxy, N-alkyl-N-alkynylaminocarbonylalkylthio having in each case up to 6 carbon atoms in the alkyl, alkenyl or alkynyl groups, or $R^7$ represents hydroxyamino, represents in each case optionally halogen-substituted N-alkylhydroxyamino, alkoxyamino, N-alkylalkoxyamino, alkoxycarbonylalkoxyamino or N-alkylalkoxycarbonylalkoxyamino having in each case 1 to 6 carbon atoms in the alkyl groups, represents in each case optionally halogen-substituted alkenyloxyamino, N-alkylalkenyloxyamino, N-alkenylalkoxyamino or N-alkenylalkenyloxyamino having in each case 3 to 6 carbon atoms in the alkenyl groups and, if appropriate, 1 to 6 carbon atoms in the alkyl groups, represents cycloalkyloxyamino or N-alkylcycloalkyloxyamino having in each case 3 to 6 carbon atoms in the cycloalkyl groups and, if appropriate, 1 to 6 carbon atoms in the alkyl group, or represents in each case optionally halogen-substituted aryloxyamino or N-alkylaryloxyamino having in each case 6 or 10 carbon atoms in the aryl groups and, if appropriate, 1 to 6 carbon atoms in the alkyl group, or $R^7$ represents cyanoalkylamino having 1 to 6 carbon atoms, represents optionally cyano-, halogen-, $C_1$-$C_4$-alkoxy- or $C_1$-$C_4$-alkoxycarbonyl-substituted dialkylamino having in each case 1 to 6 carbon atoms in the alkyl groups, represents in each case optionally cyano-, halogen- or $C_1$-$C_4$-alkoxy-carbonyl-substituted N-alkyl-N-alkenylamino or N-alkyl-N-alkynylamino having in each case up to 6 carbon atoms in the alkyl, alkenyl or alkynyl groups, or represents dialkenylamino or dialkynylamino having in each case up to 6 carbon atoms in the alkenyl or alkynyl groups, or $R^7$ represents in each case optionally nitro-, cyano-, halogen-, $C_1$-$C_4$-alkyl-, $C_1$-$C_4$-haloalkyl-, $C_1$-$C_4$-alkoxy-, $C_1$-$C_4$-haloalkoxy-, $C_1$-$C_4$-alkylthio-, $C_1$-$C_4$-haloalkylthio-, $C_1$-$C_4$-alkoxy-carbonyl-, $C_3$-$C_6$-cycloalkyl- or phenyl-substituted heterocyclyloxy, heterocyclylthio, heterocyclylamino, N-alkylheterocyclylamino, N-alkylheterocyclylalkylamino or —N=(heterocyclyl), where the monocyclic or bicyclic heterocyclyl group contains up to 6 carbon atoms, up to 5 nitrogen atoms and/or 1 or 2 oxygen atoms and/or 1 or 2 sulphur atoms and optionally additionally 1 or 2 —SO groups and/or 1 or 2 —SO$_2$ groups and/or 1 or 2 —CO groups and/or 1 or 2 —CS groups, and the alkyl group contains, if appropriate, 1 to 6 carbon atoms, or $R^7$ represents a monocyclic or bicyclic nitrogen heterocycle which is attached via N, contains up to 9 carbon atoms, up to 5 nitrogen atoms and optionally additionally 1 or 2 oxygen or sulphur atoms and optionally additionally 1 or 2 —SO groups, 1 or 2 —SO$_2$ groups, 1 or 2 —CO groups, 1 or 2 —CS groups or one cyanoimino group (C=N—CN) and is optionally substituted by nitro, cyano, halogen, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, $C_1$-$C_4$-alkoxy-carbonyl, $C_1$-$C_4$-alkoxy-carbonyl-$C_1$-$C_2$-alkoxy, $C_1$-$C_4$-alkyl-carbonylamino, $C_1$-$C_4$-alkoxy-carbonyl-amino, $C_2$-$C_4$-alkylenedioxy, $C_3$-$C_6$-cycloalkyl or phenyl, including the possible stereoisomeric forms.

In the definitions, the hydrocarbon chains, such as alkyl or alkenyl, are in each case straight-chain or branched—including in combination with heteroatoms, such as in alkoxy.

Optionally substituted radicals can be mono- or polysubstituted, where in the case of polysubstitution the substituents can be identical or different.

Preferred substituents or ranges of radicals present in the formulae listed above and below are defined below:

Q preferably represents oxygen.

$R^1$ preferably represents hydrogen, amino or optionally cyano-, fluorine-, chlorine-, bromine-, methoxy-, ethoxy-, n- or i-propoxy-substituted alkyl having 1 to 5 carbon atoms.

$R^2$ preferably represents carboxyl, cyano, carbamoyl, thiocarbamoyl or in each case optionally cyano-, fluorine-, chlorine-, bromine-, methoxy-, ethoxy-, n- or i-propoxy-substituted alkyl or alkoxycarbonyl having in each case 1 to 5 carbon atoms in the alkyl groups.

$R^3$ preferably represents hydrogen, fluorine, chlorine, bromine or optionally fluorine-, chlorine- or bromine-substituted alkyl having 1 to 5 carbon atoms.

$R^4$ preferably represents hydrogen, cyano, carbamoyl, thiocarbamoyl, fluorine, chlorine or bromine.

$R^5$ preferably represents cyano, carbamoyl, thiocarbamoyl, fluorine, chlorine, bromine, or in each case optionally fluorine-, chlorine- or bromine-substituted alkyl or alkoxy having in each case 1 to 5 carbon atoms.

$R^6$ preferably represents hydrogen, represents optionally cyano-, carboxyl-, fluorine-, chlorine-, bromine-, methoxy-, ethoxy-, n- or i-propoxy-, methylthio-, ethylthio-, n- or i-propylthio-, methylsulphinyl-, ethylsulphinyl-, n- or i-propylsulphinyl-, methylsulphonyl- or ethylsulphonyl-, acetyl-, propionyl-, n- or i-butyroyl-, methoxycarbonyl-, ethoxycarbonyl-, n- or i-propoxycarbonyl-substituted alkyl having 1 to 5 carbon atoms, represents in each case optionally cyano-, fluorine-, chlorine-, bromine-, methoxy-, ethoxy-, n- or i-propoxy-substituted alkylcarbonyl, alkoxycarbonyl or alkylsulphonyl having in each case 1 to 5 carbon atoms in the alkyl groups, represents in each case optionally fluorine-, chlorine- or bromine-substituted alkenyl, alkenyl-carbonyl, alkenylsulphonyl or alkynyl having in each case 3 to 5 carbon atoms in the alkenyl or alkynyl groups, represents in each case optionally cyano-, fluorine-, chlorine-, bromine-, methyl-, ethyl-, n- or i-propyl-substituted cycloalkyl, cycloalkylalkyl, cycloalkylcarbonyl, cycloalkylalkylcarbonyl, cycloalkylsulphonyl or cycloalkylalkylsulphonyl having in each case 3 to 6 carbon atoms in the cycloalkyl groups and, if appropriate, 1 to 3 carbon atoms in the alkyl moiety, represents in each case optionally nitro-, cyano-, fluorine-, chlorine-, bromine-, methyl-, ethyl-, n- or i-propyl-, n-, i-, s- or t-butyl-, trifluoromethyl-, chlorodifluoromethyl-, fluorodichloromethyl-, methoxy-, ethoxy-, n- or i-propoxy-, n-, i-, s- or t-butoxy-, difluoromethoxy-, trifluoromethoxy-, chlorodifluoromethoxy-, fluorodichloromethoxy-, methoxycarbonyl-, ethoxycarbonyl-, n- or i-propoxycarbonyl-, n-, i-, s- or t-butoxycarbonyl-substituted aryl, arylalkyl, arylcarbonyl, arylalkylcarbonyl, arylsulphonyl or arylalkylsulphonyl having in each case 6 or 10 carbon atoms in the aryl groups and, if appropriate, 1 to 3 carbon atoms in the alkyl moiety, or represents in each case optionally nitro-, cyano-, fluorine-, chlorine-, bromine-, methyl-, ethyl-, n- or i-propyl-, n-, i-, s- or t-butyl-, trifluoromethyl-, chlorodifluoromethyl-, fluorodichloromethyl-, methoxy-, ethoxy-, n- or i-propoxy-, n-, i-, s- or t-butoxy-, difluoromethoxy-, trifluoromethoxy-, chlorodifluoromethoxy-, fluorodichloromethoxy-, methoxycarbonyl-, ethoxycarbonyl-, n- or i-propoxycarbonyl-, n-, i-, s- or t-butoxycarbonyl-substituted heterocyclylcarbonyl, heterocyclylalkylcarbonyl, heterocyclylsulphonyl or heterocyclylalkylsulphonyl having in each case up to 5 carbon atoms, up to 4 nitrogen atoms and/or one oxygen or sulphur atom as ring members—where the heterocyclyl groups each also optionally contain an —SO group, an —SO$_2$ group, 1 or 2 —CO groups or 1 or 2 —CS groups.

$R^7$ preferably represents in each case optionally halogen-substituted alkoxycarbonylalkoxy, alkoxycarbonylalkylthio, alkenyloxycarbonylalkoxy, alkenyloxycarbonylalkylthio, alkynyloxycarbonylalkoxy, alkynyloxycarbonylalkylthio, carbamoylalkoxy, carbamoylalkylthio, alkylaminocarbonylalkoxy, alkylaminocarbonylalkylthio, dialkylaminocarbonylalkoxy, dialkylaminocarbonylalkylthio, dialkenylaminocarbonylalkoxy, dialkenylaminocarbonylalkylthio, dialkynylaminocarbonyloxy or dialkynylaminocarbonylalkylthio having in each case up to 5 carbon atoms in the alkyl, alkenyl or alkynyl groups.

$R^7$ furthermore preferably represents hydroxyamino, represents in each case optionally halogen-substituted N-alkylhydroxyamino, alkoxyamino, N-alkylalkoxyamino, alkoxycarbonylalkoxyamino or N-alkylalkoxycarbonylalkoxyamino having in each case 1 to 5 carbon atoms in the alkyl groups, represents in each case optionally halogen-substituted alkenyloxyamino, N-alkylalkenyloxyamino, N-alkenylalkoxyamino or N-alkenylalkenyloxyamino having in each case 3 to 5 carbon atoms in the alkenyl groups and, if appropriate, 1 to 5 carbon atoms in the alkyl groups, represents cycloalkyloxyamino or N-alkylcycloalkyloxyamino having in each case 3 to 6 carbon atoms in the cycloalkyl groups and, if appropriate, 1 to 3 carbon atoms in the alkyl group, or represents in each case optionally halogen-substituted aryloxyamino or N-alkylaryloxyamino having in each case 6 or 10 carbon atoms in the aryl groups and, if appropriate, 1 to 3 carbon atoms in the alkyl group.

$R^7$ furthermore preferably represents cyanoalkylamino having 1 to 5 carbon atoms, represents in each case optionally cyano-, fluorine-, chlorine-, methoxy-, ethoxy-, n- or i-propoxy-, methoxycarbonyl-, ethoxycarbonyl-, n- or i-propoxycarbonyl-substituted dialkylamino having in each case 1 to 5 carbon atoms in the alkyl groups, represents in each case optionally cyano-, fluorine-, chlorine-, methoxy-, ethoxy-, n- or i-propoxy-, methoxycarbonyl-, ethoxycarbonyl-, n- or i-propoxycarbonyl-substituted N-alkyl-N-alkenylamino or N-alkyl-N-alkynylamino having in each case up to 5 carbon atoms in the alkyl, alkenyl or alkynyl groups, represents dialkenylamino or dialkynylamino having in each case up to 5 carbon atoms in the alkenyl or alkynyl groups.

$R^7$ furthermore preferably represents in each case optionally nitro-, cyano-, fluorine-, chlorine-, bromine-, methyl-, ethyl-, n- or i-propyl-, n-, i-, s- or t-butyl-, difluoromethyl-, dichloromethyl-, trifluoromethyl-, chlorodifluoromethyl-, fluorodichloromethyl-, methoxy-, ethoxy-, n- or i-propoxy-, n-, i-, s- or t-butoxy-, difluoromethoxy-, trifluoromethoxy-, chlorodifluoromethoxy-, methylthio-, ethylthio-, n- or i-propylthio-, n-, i-, s- or t-butylthio-, difluoromethylthio-, trifluoromethylthio-, chlorodifluoromethylthio-, methoxycarbonyl-, ethoxycarbonyl-, n- or i-propoxycarbonyl-, n-, i-, s- or t-butoxycarbonyl-, cyclopropyl-, cyclobutyl-, cyclopentyl-, cyclohexyl- or phenyl-substituted heterocyclyloxy, heterocyclylthio, heterocyclylamino, N-alkylheterocyclylamino, N-alkylheterocyclylalkylamino or —N=(heterocyclyl), where the monocyclic or bicyclic heterocyclyl group contains up to 6 carbon atoms, up to 5 nitrogen atoms and/or 1 or 2 oxygen atoms and/or 1 or 2 sulphur atoms and optionally additionally 1 or 2 —SO groups and/or 1 or 2 —SO$_2$ groups and/or 1 or 2 —CO groups and/or 1 or 2 —CS groups and the alkyl group contains, if appropriate, 1 to 3 carbon atoms.

$R^7$ furthermore preferably represents a monocyclic or bicyclic nitrogen heterocycle which is attached via N, contains up to 9 carbon atoms, up to 5 nitrogen atoms and optionally additionally 1 or 2 oxygen or sulphur atoms and optionally additionally 1 or 2 —SO groups, 1 or 2 —SO2 groups, 1 or 2 —CO groups, 1 or 2 —CS groups or one cyanoimino group (C=N—CN) and is optionally substituted by nitro, cyano, fluorine, chlorine, bromine, methyl, ethyl, n- or i-propyl, n-, i-, s- or t-butyl, difluoromethyl, dichloromethyl, trifluoromethyl, chlorodifluoromethyl, fluorodichloromethyl, methoxy, ethoxy, n- or i-propoxy, n-, i-, s- or t-butoxy, difluoromethoxy, trifluoromethoxy, chlorodifluoromethoxy, methylthio, ethylthio, n- or i-propylthio, n-, i-, s- or t-butylthio, difluoromethylthio, trifluoromethylthio, chlorodifluoromethylthio, methoxycarbonyl, ethoxycarbonyl, n- or i-propoxycarbonyl, n-, i-, s- or t-butoxycarbonyl, methoxycarbonylmethoxy, ethoxycarbonylmethoxy, acetylamino, propionylamino, methoxycarbonylamino, ethoxycarbonylamino, ethylenedioxy, propylenedioxy, cyclopropyl, cyclobutyl, cyclopentyl, cyclohexyl or phenyl.

$R^1$ particularly preferably represents hydrogen, amino or in each case optionally cyano-, fluorine-, chlorine-, bromine-, methoxy-, ethoxy-, n- or i-propoxy-substituted methyl, ethyl, n- or i-propyl, n-, i- or s-butyl.

$R^2$ particularly preferably represents carboxyl, cyano, carbamoyl, thiocarbamoyl or in each case optionally cyano-, fluorine-, chlorine-, bromine-, methoxy-, ethoxy-, n- or i-propoxy-substituted methyl, ethyl, n- or i-propyl, methoxycarbonyl, ethoxycarbonyl, n- or i-propoxycarbonyl.

$R^3$ particularly preferably represents hydrogen, fluorine, chlorine, bromine or in each case optionally fluorine-, chlorine- or bromine-substituted methyl, ethyl, n- or i-propyl.

$R^4$ particularly preferably represents hydrogen, cyano, carbamoyl, thiocarbamoyl, fluorine, chlorine or bromine.

$R^5$ particularly preferably represents cyano, carbamoyl, thiocarbamoyl, fluorine, chlorine, bromine, or in each case optionally fluorine-, chlorine- or bromine-substituted methyl, ethyl, n- or i-propyl, methoxy, ethoxy, n- or i-propoxy.

$R^6$ particularly preferably represents hydrogen, represents in each case optionally cyano-, carboxyl-, fluorine-, chlorine-, bromine-, methoxy-, ethoxy-, n- or i-propoxy-, methylthio-, ethylthio-, n- or i-propylthio-, methylsulphinyl-, ethylsulphinyl-, n- or i-propylsulphinyl-, methylsulphonyl- or ethylsulphonyl-, acetyl-, propionyl-, n- or i-butyroyl-, methoxycarbonyl-, ethoxycarbonyl-, n- or i-propoxycarbonyl-substituted methyl, ethyl, n- or i-propyl, n-, i- or s-butyl, represents in each case optionally cyano-, fluorine-, chlorine-, bromine-, methoxy-, ethoxy-, n- or i-propoxy-substituted acetyl, propionyl, n- or i-butyroyl, methoxycarbonyl, ethoxycarbonyl, n- or i-propoxycarbonyl, n-, i-, s- or t-butoxycarbonyl, methylsulphonyl, ethylsulphonyl, n- or i-propylsulphonyl, n-, i- or s-butylsulphonyl, represents in each case optionally fluorine-, chlorine- or bromine-substituted propenyl, butenyl, propenylsulphonyl, butenylsulphonyl, propynyl or butynyl, represents in each case optionally cyano-, fluorine-, chlorine-, bromine-, methyl- or ethyl-substituted cyclopropyl, cyclobutyl, cyclopentyl, cyclohexyl, cyclopropylmethyl, cyclobutylmethyl, cyclopentylmethyl, cyclohexylmethyl, cyclopropylcarbonyl, cyclobutylcarbonyl, cyclopentylcarbonyl, cyclohexylcarbonyl, cyclopropylmethylcarbonyl, cyclobutylmethylcarbonyl, cyclopentylmethylcarbonyl, cyclohexylmethylcarbonyl, cyclopropylsulphonyl, cyclobutylsulphonyl, cyclopentylsulphonyl, cyclohexylsulphonyl, cyclopropylmethylsulphonyl, cyclobutylmethylsulphonyl, cyclopentylmethylsulphonyl or cyclohexylmethylsulphonyl, represents in each case optionally nitro-, cyano-, fluorine-, chlorine-, bromine-, methyl-, ethyl-, n- or i-propyl-, n-, i-, s- or t-butyl-, trifluoromethyl-, chlorodifluoromethyl-, fluorodichloromethyl-, methoxy-, ethoxy-, n- or i-propoxy-, n-, i-, s- or t-butoxy-, difluoromethoxy-, trifluoromethoxy-, chlorodifluoromethoxy-, fluorodichloromethoxy-, methoxycarbonyl-, ethoxycarbonyl-, n- or i-propoxycarbonyl-, n-, i-, s- or t-butoxycarbonyl-substituted phenyl, phenylmethyl, phenylethyl, phenylpropyl, benzoyl, phenylacetyl, phenylsulphonyl or phenylmethylsulphonyl, or represents in each case optionally nitro-, cyano-, fluorine-, chlorine-, bromine-, methyl-, ethyl-, n- or i-propyl-, n-, i-, s- or t-butyl-, trifluoromethyl-, chlorodifluoromethyl-, fluorodichloromethyl-, methoxy-, ethoxy-, n- or i-propoxy-, n-, i-, s- or t-butoxy-, difluoromethoxy-, trifluoromethoxy-, chlorodifluoromethoxy-, fluorodichloromethoxy-, methoxycarbonyl-, ethoxycarbonyl-, n- or i-propoxycarbonyl-, n-, i-, s- or t-butoxycarbonyl-substituted heterocyclylcarbonyl, heterocyclylmethylcarbonyl, heterocyclylsulphonyl or heterocyclylmethylsulphonyl, where the heterocyclyl grouping is selected from the group consisting of furyl, tetrahydrofuryl, thienyl, pyrrolyl, pyrrolinyl, pyrrolidinyl, oxopyrrolidinyl, pyrrolyl, pyrazolyl, oxazolyl, oxazolinyl, oxazolidinyl, isoxazolyl, thiazolyl, thiazolinyl, thiazolidinyl, cyanoiminothiazolidinyl, imidazolyl, imidazolinyl, 2-oxo-1,3-diazacyclopentyl (2-oxoimidazolidinyl), triazolyl, oxotriazolinyl, thioxotriazolinyl, pyridinyl, piperidinyl, oxopiperidinyl, 2-oxo-1,3-diazacyclohexyl, morpholinyl, piperazinyl.

$R^7$ particularly preferably represents methoxycarbonylmethoxy, ethoxycarbonylmethoxy, n- or i-propoxycarbonylmethoxy, n-, i-, s- or t-butoxycarbonylmethoxy, methoxycarbonylethoxy, ethoxycarbonylethoxy, n- or i-propoxycarbonylethoxy, n-, i-, s- or t-butoxycarbonylethoxy, methoxycarbonylmethylthio, ethoxycarbonylmethylthio, n- or i-propoxycarbonylmethylthio, n-, i-, s- or t-butoxycarbonylmethylthio, methoxycarbonylethylthio, ethoxycarbonylethylthio, n- or i-propoxycarbonylethylthio, n-, i-, s- or t-butoxycarbonylethylthio, propenyloxycarbonylmethoxy, butenyloxycarbonylmethoxy, propenyloxycarbonylethoxy, butenyloxycarbonylethoxy, propenyloxycarbonylmethylthio, butenyloxycarbonylmethylthio, propenyloxycarbonylethylthio, butenyloxycarbonylethylthio, propynyloxycarbonylmethoxy, butynyloxycarbonylmethoxy, propynyloxycarbonylethoxy, butynyloxycarbonylethoxy, propynyloxycarbonylmethylthio, butynyloxycarbonylmethylthio, propynyloxycarbonylethylthio, butynyloxycarbonylethylthio, carbamoylmethoxy, carbamoylethoxy, carbamoylmethylthio, carbamoylethylthio, methylaminocarbonylmethoxy, ethylaminocarbonylethoxy, n- or i-propylaminocarbonylmethoxy, n-, i-, s- or t-butylaminocarbonylmethoxy, methylaminocarbonylethoxy, ethylaminocarbonylethoxy, n- or i-propylaminocarbonylethoxy, n-, i-, s- or t-butylaminocarbonylethoxy, methylaminocarbonylmethylthio, ethylaminocarbonylmethylthio, n- or i-propylaminocarbonylmethylthio, n-, i-, s- or t-butylaminocarbonylmethylthio, methylaminocarbonylethylthio, ethylaminocarbonylethylthio, n- or i-propylaminocarbonylethylthio, n-, i-, s- or t-butylaminocarbonylethylthio, dimethylaminocarbonylmethoxy, diethylaminocarbonylmethoxy, dimethylaminocarbonylethoxy, diethylaminocarbonylethoxy, dimethylaminocarbonylmethylthio, diethylaminocarbonylmethylthio, dimethylaminocarbonylethylthio, diethylaminocarbonylethylthio, dipropenylaminocarbonylmethoxy, dipropenylaminocarbonylethoxy, dipropenylaminocarbonylmethylthio, dipropenylaminocarbonylethylthio, dipropynylaminocarbonylmethoxy, dipropynylaminocarbonylethoxy, dipropynylaminocarbonylmethylthio or dipropynylaminocarbonylethylthio.

$R^7$ furthermore particularly preferably represents hydroxyamino, represents N-methylhydroxyamino, N-ethylhydroxyamino, N-n-propylhydroxyamino, N-i-propylhydroxyamino, methoxyamino, ethoxyamino, n- or i-propoxyamino, n-, i-, s- or t-butoxyamino, N-methylmethoxyamino, N-ethylmethoxyamino, N-methylethoxyamino, methoxycarbonylmethoxyamino, ethoxycarbonylmethoxyamino, n- or i-propoxycarbonylmethoxyamino, methoxycarbonylethoxyamino, ethoxycarbonylethoxyamino, n- or i-propoxycarbonylethoxyamino, N-methylmethoxycarbonylmethoxyamino, N-methylethoxycarbonylmethoxyamino, N-methyl-n-propoxycarbonylmethoxyamino, N-methyl-i-propoxycarbonylmethoxyamino, N-methylmethoxycarbonylethoxyamino, N-methylethoxycarbonylethoxyamino, N-methyl-n-propoxycarbonylethoxyamino, N-methyl-i-propoxycarbonylethoxyamino, propenyloxyamino, butenyloxyamino, N-methylpropenyloxyamino, N-methylbutenyloxyamino, N-propenyl-methoxyamino, N-propenylethoxyamino, N-propenyl-n-propoxyamino, N-propenyl-i-propoxyamino, N-propenylpropenyloxyamino, represents cyclopentyloxyamino, cyclohexyloxyamino, N-methylcyclopentyloxyamino or N-methylcyclohexyloxyamino, or represents phenoxyamino or N-methylphenoxyamino.

$R^7$ furthermore particularly preferably represents cyanomethylamino, cyanoethylamino, cyanopropylamino or cyanobutylamino, represents in each case optionally cyano-, fluorine-, chlorine-, methoxy-, ethoxy-, n- or i-propoxy-, methoxycarbonyl-, ethoxycarbonyl, n- or i-propoxycarbonyl-substituted dimethylamino, diethylamino, dipropylamino or dibutylamino, represents in each case optionally cyano-, fluorine-, chlorine-, methoxy-, ethoxy-, n- or i-propoxy-, methoxycarbonyl-, ethoxycarbonyl-, n- or i-propoxycarbonyl-substituted N-methyl-N-propenylamino, N-methyl-N-butenylamino, N-ethyl-N-propenylamino, N-ethyl-N-butenylamino, N-propyl-N-propenylamino, N-propyl-N-butenylamino, N-butyl-N-propenylamino, N-butyl-N-butenylamino, N-methyl-N-propynylamino, N-methyl-N-butynylamino, N-ethyl-N-propynylamino, N-ethyl-N-butynylamino, N-propyl-N-propynylamino, N-propyl-N-butynylamino, N-butyl-N-propynylamino, N-butyl-N-butynylamino, or represents dipropenylamino, dibutenylamino, dipropynylamino or dibutynylamino.

$R^7$ furthermore particularly preferably represents in each case optionally nitro-, cyano-, fluorine-, chlorine-, bromine-, methyl-, ethyl-, n- or i-propyl-, n-, i-, s- or t-butyl-, difluoromethyl-, dichloromethyl-, trifluoromethyl-, chlorodifluoromethyl-, fluorodichloromethyl-, methoxy-, ethoxy-, n- or i-propoxy-, n-, i-, s- or t-butoxy-, difluoromethoxy-, trifluoromethoxy-, chlorodifluoromethoxy-, methylthio-, ethylthio-, n- or i-propylthio-, n-, i-, s- or t-butylthio-, difluoromethylthio-, trifluoromethylthio-, chlorodifluoromethylthio-, methoxycarbonyl-, ethoxycarbonyl-, n- or i-propoxycarbonyl-, n-, i-, s- or t-butoxycarbonyl-, methoxycarbonylmethoxy-, acetylamino-, ethylenedioxy-, propylenedioxy-, cyclopropyl-, cyclobutyl-, cyclopentyl-, cyclohexyl- or phenyl-substituted heterocyclyloxy, heterocyclylthio, heterocyclylamino, N-methylheterocyclylamino, N-ethylheterocyclylamino, N-methylheterocyclylmethylamino, N-ethylheterocyclylmethylamino or —N=(heterocyclyl), where the heterocyclyl grouping is selected from the group consisting of furyl, tetrahydrofuryl, thienyl, pyrrolyl, pyrrolinyl, pyrrolidinyl, oxopyrrolidinyl, pyrrolyl, pyrazolyl, oxazolyl, oxazolinyl, oxazolidinyl, isoxazolyl, thiazolyl, thiazolinyl, thiazolidinyl, cyanoiminothiazolidinyl, imidazolyl, imidazolinyl, 2-oxo-1,3-diazacyclopentyl (2-oxoimidazolidinyl), triazolyl, oxotriazolinyl, thioxotriazolinyl, pyridinyl, piperidinyl, oxopiperidinyl, 2-oxo-1,3-diazacyclohexyl, morpholinyl, piperazinyl, pyrimidinyl.

$R^7$ furthermore particularly preferably represents a monocyclic or bicyclic nitrogen heterocycle from the group consisting of pyrrolyl, pyrrolinyl, pyrrolidinyl, oxopyrrolidinyl, pyrazolyl, imidazolyl, imidazolinyl, 2-oxo-1,3-diazacyclopentyl (2-oxoimidazolidinyl), 2-oxooxazolidinyl, isoxazolidinyl, thiazolinyl, 2-oxothiazolidinyl, isothiazolidinyl, 1-oxoisothiazolidinyl, 1,1-dioxoisothiazolidinyl, 2-cyanoiminothiazolidinyl, triazolyl, oxotriazolinyl, thioxotriazolinyl, pyridinyl, piperidinyl, oxopiperidinyl, 1,2-oxazacyclohexyl, 1,2-oxazacyclohexenyl, 2-oxo-1,3-diazacyclohexyl, morpholinyl or piperazinyl, which is attached via N and is optionally substituted by nitro, cyano, fluorine, chlorine, bromine, methyl, ethyl, n- or i-propyl, n-, i-, s- or t-butyl, difluoromethyl, dichloromethyl, trifluoromethyl, chlorodifluoromethyl, fluorodichloromethyl, methoxy, ethoxy, n- or i-propoxy, n-, i-, s- or t-butoxy, difluoromethoxy, trifluoromethoxy, chlorodifluoromethoxy, methylthio, ethylthio, n- or i-propylthio, n-, i-, s- or t-butylthio, difluoromethylthio, trifluoromethylthio, chlorodifluoromethylthio, methoxycarbonyl, ethoxycarbonyl, n- or i-propoxycarbonyl, n-, i-, s- or t-butoxycarbonyl, cyclopropyl, cyclobutyl, cyclopentyl, cyclohexyl or phenyl.

$R^1$ very particularly preferably represents hydrogen, amino or in each case optionally cyano-, fluorine-, chlorine-, methoxy- or ethoxy-substituted methyl, ethyl, n- or i-propyl.

$R^2$ very particularly preferably represents in each case optionally cyano-, fluorine-, chlorine-, methoxy-, ethoxy-, n- or i-propoxy-substituted methyl, ethyl, n- or i-propyl.

$R^3$ very particularly preferably represents hydrogen, fluorine, chlorine or in each case optionally fluorine- or chlorine-substituted methyl or ethyl.

$R^4$ very particularly preferably represents hydrogen, fluorine or chlorine.

$R^5$ very particularly preferably represents cyano, carbamoyl, thiocarbamoyl, fluorine, chlorine, bromine, or in each case optionally fluorine- or chlorine-substituted methyl, ethyl, methoxy or ethoxy.

$R^6$ very particularly preferably represents hydrogen, represents in each case optionally cyano-, carboxyl-, fluorine-, chlorine-, methoxy-, ethoxy-, n- or i-propoxy-, methylthio-, ethylthio-, methylsulphinyl-, ethylsulphinyl-, methylsulphonyl- or ethylsulphonyl-, acetyl-, propionyl-, n- or i-butyroyl-, methoxycarbonyl-, ethoxycarbonyl-, n- or i-propoxycarbonyl-substituted methyl, ethyl, n- or i-propyl, n-, i- or s-butyl, represents in each case optionally cyano-, fluorine-, chlorine-, bromine-, methoxy-, ethoxy-, n- or i-propoxy-substituted acetyl, propionyl, n- or i-butyroyl, methoxycarbonyl, ethoxycarbonyl, n- or i-propoxycarbonyl, methylsulphonyl, ethylsulphonyl, n- or i-propylsulphonyl, n-, i- or s-butylsulphonyl, represents in each case optionally fluorine-, chlorine- or bromine-substituted propenyl, butenyl, propynyl or butynyl, represents in each case optionally cyano-, fluorine-, chlorine-, methyl- or ethyl-substituted cyclopropyl, cyclopentyl, cyclohexyl, cyclopropylmethyl, cyclopentylmethyl, cyclohexylmethyl, cyclopropylcarbonyl, cyclopentylcarbonyl, cyclohexylcarbonyl, cyclopropylsulphonyl, cyclopentylsulphonyl or cyclohexylsulphonyl, represents in each case optionally nitro-, cyano-, fluorine-, chlorine-, bromine-, methyl-, ethyl-, n- or i-propyl-, n-, i-, s- or t-butyl-, trifluoromethyl-, chlorodifluoromethyl-, fluorodichloromethyl-, methoxy-, ethoxy-, n- or i-propoxy-, difluoromethoxy-, trifluoromethoxy-, chlorodifluoromethoxy-, fluorodichloromethoxy-, methoxycarbonyl-, ethoxycarbonyl-, n- or i-propoxycarbonyl-, n-, i-, s- or t-butoxycarbonyl-substituted phenyl, phenylmethyl, phenylethyl, benzoyl, phenylacetyl, phenylsulphonyl or phenylmethylsulphonyl, or represents in each case optionally nitro-, cyano-, fluorine-, chlorine-, bromine-, methyl-, ethyl-, n- or i-propyl-, n-, i-, s- or t-butyl-, trifluoromethyl-, chlorodifluoromethyl-, fluorodichloromethyl-, methoxy-, ethoxy-, n- or i-propoxy-, n-, i-, s- or t-butoxy-, difluoromethoxy-, trifluoromethoxy-, chlorodifluoromethoxy-, fluorodichloromethoxy-, methoxycarbonyl-, ethoxycarbonyl-, n- or i-propoxycarbonyl-, n-, i-, s- or t-butoxycarbonyl-substituted heterocyclylcarbonyl, heterocyclylmethylcarbonyl, heterocyclylsulphonyl or heterocyclylmethylsulphonyl, where the heterocyclyl grouping is selected from the group consisting of furyl, tetrahydrofuryl, thienyl, pyrrolyl, pyrrolinyl, pyrrolidinyl, oxopyrrolidinyl, pyrrolyl, pyrazolyl, oxazolyl, oxazolinyl, oxazolidinyl, isoxazolyl, thiazolyl, thiazolinyl, thiazolidinyl, cyanoiminothiazolidinyl, imidazolyl, imidazolinyl, 2-oxo-1,3-diazacyclopentyl (2-oxoimidazolidinyl), triazolyl, oxotriazolinyl, thioxotriazolinyl, pyridinyl, piperidinyl, oxopiperidinyl, 2-oxo-1,3-diazacyclohexyl, morpholinyl, piperazinyl.

$R^7$ very particularly preferably represents methoxycarbonylmethoxy, ethoxycarbonylmethoxy, n- or i-propoxycarbonylmethoxy, n-, i-, s- or t-butoxycarbonylmethoxy, methoxycarbonylethoxy, ethoxycarbonylethoxy, n- or i-propoxycarbonylethoxy, n-, i-, s- or t-butoxycarbonylethoxy, methoxycarbonylmethylthio, ethoxycarbonylmethylthio, n- or i-propoxycarbonylmethylthio, n-, i-, s- or t-butoxycarbonylmethylthio, methoxycarbonylethylthio, ethoxycarbonylethylthio, n- or i-propoxycarbonylethylthio, n-, i-, s- or t-butoxycarbonylethylthio, propenyloxycarbonylmethoxy, butenyloxycarbonylmethoxy, propenyloxycarbonylethoxy, butenyloxycarbonylethoxy, propenyloxycarbonylmethylthio, butenyloxycarbonylmethylthio, propenyloxycarbonylethylthio, butenyloxycarbonylethylthio, propynyloxycarbonylmethoxy, butynyloxycarbonylmethoxy, propynyloxycarbonylethoxy, butynyloxycarbonylethoxy, propynyloxycarbonylmethylthio, butynyloxycarbonylmethylthio, propynyloxycarbonylethylthio, butynyloxycarbonylethylthio, methylaminocarbonylmethoxy, ethylaminocarbonylethoxy, n- or i-propylaminocarbonylmethoxy, n-, i-, s- or t-butylaminocarbonylmethoxy, methylaminocarbonylethoxy, ethylaminocarbonylethoxy, n- or i-propylaminocarbonylethoxy, n-, i-, s- or t-butylaminocarbonylethoxy, methylaminocarbonylmethylthio, ethylaminocarbonylmethylthio, n- or i-propylaminocarbonylmethylthio, n-, i-, s- or t-butylaminocarbonylmethylthio, methylaminocarbonylethylthio, ethylaminocarbonylethylthio, n- or i-propylaminocarbonylethylthio, n-, i-, s- or t-butylaminocarbonylethylthio, dimethylaminocarbonylmethoxy, diethylaminocarbonylmethoxy, dimethylaminocarbonylethoxy, diethylaminocarbonylethoxy, dimethylaminocarbonylmethylthio, diethylaminocarbonylmethylthio, dimethylaminocarbonylethylthio, diethylaminocarbonylethylthio, dipropenylaminocarbonylmethoxy, dipropenylaminocarbonylethoxy, dipropenylaminocarbonylmethylthio, dipropenylaminocarbonylethylthio, dipropynylaminocarbonylmethoxy, dipropynylaminocarbonylethoxy, dipropynylaminocarbonylmethylthio or dipropynylaminocarbonylethylthio.

$R^7$ furthermore very particularly preferably represents hydroxyamino, represents N-methylhydroxyamino, N-ethyl-hydroxyamino, N-n-propylhydroxyamino, N-i-propylhydroxyamino, methoxyamino, ethoxyamino, n- or i-propoxyamino, n-, i-, s- or t-butoxyamino, N-methylmethoxyamino, N-ethylmethoxyamino, N-methylethoxyamino, methoxycarbonylmethoxyamino, ethoxycarbonylmethoxyamino, n- or i-propoxycarbonylmethoxyamino, methoxycarbonylethoxyamino, ethoxycarbonylethoxyamino, n- or i-propoxycarbonylethoxyamino, N-methylmethoxycarbonylmethoxyamino, N-methylethoxycarbonylmethoxyamino, N-methyl-n-propoxycarbonylmethoxyamino, N-methyl-i-propoxycarbonylmethoxyamino, N-methyl-methoxycarbonylethoxyamino, N-methylethoxycarbonylethoxyamino, N-methyl-n-propoxycarbonylethoxyamino, N-methyl-i-propoxycarbonylethoxyamino, propenyloxyamino, butenyloxyamino, N-methyl-propenyloxyamino, N-methylbutenyloxyamino, N-propenylmethoxyamino, N-propenylethoxyamino, N-propenyl-n-propoxyamino, N-propenyl-i-propoxyamino, N-propenylpropenyloxyamino, or represents phenoxyamino or N-methylphenoxyamino.

$R^7$ furthermore very particularly preferably represents cyanoethylamino, cyanopropylamino or cyanobutylamino, represents dimethylamino, diethylamino, di-n-propylamino, di-i-propylamino, di-n-butylamino or di-i-butylamino, represents N-methylcyanoethylamino, N-ethylcyanoethylamino, N-n-propylcyanoethylamino, N-i-propylcyanoethylamino, N-methylfluoroethylamino, N-ethylfluoroethylamino, N-n-propylfluoroethylamino, N-i-propylfluoroethylamino, N-methylmethoxyethylamino, N-ethylmethoxyethylamino, N-methylethoxyethylamino, N-ethylethoxyethylamino, N-methylmethoxycarbonylmethylamino, N-methylethoxycarbonylmethylamino, N-methylmethoxycarbonylethylamino, N-methylethoxycarbonylethylamino, represents N-methyl-N-propenylamino, N-methyl-N-butenylamino, N-ethyl-N-propenylamino, N-ethyl-N-butenylamino, N-propyl-N-propenylamino, N-propyl-N-butenylamino, N-butyl-N-propenylamino, N-butyl-N-butenylamino, N-methyl-N-propynylamino, N-methyl-N-butynylamino, N-ethyl-N-propynylamino, N-ethyl-N-butynylamino, N-propyl-N-propynylamino, N-propyl-N-butynylamino, N-butyl-N-propynylamino or N-butyl-N-butynylamino, or represents dipropenylamino, dibutenylamino, dipropynylamino or dibutynylamino.

$R^7$ furthermore very particularly preferably represents in each case optionally nitro-, cyano-, fluorine-, chlorine-, bromine-, methyl-, ethyl-, n- or i-propyl-, n-, i-, s- or t-butyl-, difluoromethyl-, dichloromethyl-, trifluoromethyl-, chlorodifluoromethyl-, fluorodichloromethyl-, methoxy-, ethoxy-, n- or i-propoxy-, n-, i-, s- or t-butoxy-, difluoromethoxy-, trifluoromethoxy-, chlorodifluoromethoxy-, methylthio-, ethylthio-, n- or i-propylthio-, n-, i-, s- or t-butylthio-, difluoromethylthio-, trifluoromethylthio-, chlorodifluoromethylthio-, methoxycarbonyl-, ethoxycarbonyl-, n- or i-propoxycarbonyl-, n-, i-, s- or t-butoxycarbonyl-, cyclopropyl-, cyclobutyl-, cyclopentyl-, cyclohexyl- or phenyl-substituted heterocyclyloxy, heterocyclylthio, heterocyclylamino, N-methylheterocyclylamino, N-methylheterocyclylmethylamino or —N=(heterocyclyl), where the heterocyclyl grouping is selected from the group consisting of furyl, tetrahydrofuryl, thienyl, pyrrolyl, pyrrolinyl, pyrrolidinyl, oxopyrrolidinyl, pyrrolyl, pyrazolyl, oxazolyl, oxazolinyl, oxazolidinyl, isoxazolyl, thiazolyl, thiazolinyl, thiazolidinyl, cyanoiminothiazolidinyl, imidazolyl, imidazolinyl, 2-oxo-1,3-diazacyclopentyl (2-oxoimidazolidinyl), triazolyl, oxotriazolinyl, thioxotriazolinyl, pyridinyl, piperidinyl, oxopiperidinyl, 2-oxo-1,3-diazacyclohexyl, morpholinyl, piperazinyl, pyrimidinyl.

$R^7$ furthermore very particularly preferably represents a monocyclic or bicyclic nitrogen heterocycle from the group consisting of pyrrolyl, pyrrolinyl, pyrrolidinyl, oxopyrrolidinyl, pyrazolyl, imidazolyl, imidazolinyl, 2-oxo-1,3-diazacyclopentyl (2-oxoimidazolidinyl), 2-oxo-1,3-oxazacyclopentyl (2-oxooxazolidinyl), isoxazolidinyl, thiazolinyl, 2-oxothiazolidinyl, 1,1-dioxoisothiazolidinyl, 2-cyanoiminothiazolidinyl, triazolyl, oxotriazolinyl, thioxotriazolinyl, pyridinyl, piperidinyl, oxopiperidinyl, 2-oxo-1,3-diazacyclohexyl, morpholinyl or piperazinyl, which is attached via N and is optionally substituted by nitro, cyano, fluorine, chlorine, bromine, methyl, ethyl, n- or i-propyl, n-, i-, s- or t-butyl, difluoromethyl, dichloromethyl, trifluoromethyl, chlorodifluoromethyl, fluorodichloromethyl, methoxy, ethoxy, n- or i-propoxy, n-, i-, s- or t-butoxy, difluoromethoxy, trifluoromethoxy, chlorodifluoromethoxy, methylthio, ethylthio, n- or i-propylthio, n-, i-, s- or t-butylthio, difluoromethylthio, trifluoromethylthio, chlorodifluoromethylthio, methoxycarbonyl, ethoxycarbonyl, n- or i-propoxycarbonyl, n-, i-, s- or t-butoxycarbonyl, cyclopropyl, cyclobutyl, cyclopentyl, cyclohexyl or phenyl.

$R^6$ most preferably represents hydrogen, represents in each case optionally fluorine-, chlorine-, methoxy- or ethoxy-substituted methyl, ethyl, acetyl, methoxycarbonyl or ethoxycarbonyl.

$R^6$ especially preferably represents hydrogen, methyl or ethyl.

Preference according to the invention is given to the compounds of the formula (I) which contain a combination of the meanings listed above as being preferred.

Particular preference according to the invention is given to the compounds of the formula (I) which contain a combination of the meanings listed above as being particularly preferred.

Very particular preference according to the invention is given to the compounds of the formula (I) which contain a combination of the meanings listed above as being very particularly preferred.

A very particularly preferred group are those compounds of the formula (I) in which Q represents oxygen or sulphur,
$R^1$ represents hydrogen, amino or methyl,
$R^2$ represents cyano or trifluoromethyl,
$R^3$ represents hydrogen, chlorine or methyl,
$R^4$ represents hydrogen, fluorine or chlorine,
$R^5$ represents cyano, thiocarbamoyl, chlorine, bromine or trifluoromethyl,
$R^6$ represents hydrogen, represents in each case optionally cyano-, fluorine-, chlorine-, methoxy-, ethoxy-, methylthio-, ethylthio-, methylsulphinyl-, ethylsulphinyl-, methylsulphonyl-, ethylsulphonyl-, acetyl-, propionyl-, methoxycarbonyl- or ethoxycarbonyl-substituted methyl or ethyl, represents in each case optionally cyano-, fluorine-, chlorine-, bromine-, methoxy- or ethoxy-substituted acetyl, propionyl, methoxycarbonyl, ethoxycarbonyl, represents in each case optionally fluorine- or chlorine-substituted methylsulphonyl or ethylsulphonyl, represents in each case optionally fluorine- or chlorine-substituted propenyl, butenyl, propynyl or butynyl, represents in each case optionally fluorine-, chlorine- or methyl-substituted cyclopropyl or cyclopropylmethyl, cyclopropylcarbonyl or cyclopropylsulphonyl, represents in each case optionally nitro-, cyano-, fluorine-, chlorine-, bromine-, methyl-, ethyl-, n- or i-propyl-, n-, i-, s- or t-butyl-, trifluoromethyl-, chlorodifluoromethyl-, fluorodichloromethyl-, methoxy-, ethoxy-, n- or i-propoxy-, difluoromethoxy-, trifluoromethoxy-, chlorodifluoromethoxy-, fluorodichloromethoxy-, methoxycarbonyl-, ethoxycarbonyl-, n- or i-propoxycarbonyl-substituted phenyl, phenylmethyl, phenylethyl, benzoyl, phenylacetyl, phenylsulphonyl or phenylmethylsulphonyl, or represents in each case optionally nitro-, cyano-, fluorine-, chlorine-, bromine-, methyl-, ethyl-, n- or i-propyl-, n-, i-, s- or t-butyl-, trifluoromethyl-, chlorodifluoromethyl-, fluorodichloromethyl-, methoxy-, ethoxy-, n- or i-propoxy-, n-, i-, s- or t-butoxy-, difluoromethoxy-, trifluoromethoxy-, chlorodifluoromethoxy-, fluorodichloromethoxy-, methoxycarbonyl-, ethoxycarbonyl-, n- or i-propoxycarbonyl-, n-, i-, s- or t-butoxycarbonyl-substituted heterocyclylcarbonyl, heterocyclylmethylcarbonyl, heterocyclylsulphonyl or heterocyclylmethylsulphonyl, where the heterocyclyl grouping is selected from the group consisting of furyl, tetrahydrofuryl, thienyl, pyrrolyl, pyrrolinyl, pyrrolidinyl, oxopyrrolidinyl, pyrrolyl, pyrazolyl, oxazolyl, oxazolinyl, oxazolidinyl, isoxazolyl, thiazolyl, thiazolinyl, thiazolidinyl, cyanoiminothiazolidinyl, imidazolyl, imidazolinyl, 2-oxo-1,3-diazacyclopentyl (2-oxoimidazolidinyl), triazolyl, oxotriazolinyl, thioxotriazolinyl, pyridinyl, piperidinyl, oxopiperidinyl, 2-oxo-1,3-diazacyclohexyl, morpholinyl, piperazinyl, and $R^7$ represents methoxycarbonylmethoxy, ethoxycarbonylmethoxy, n- or i-propoxycarbonylmethoxy, n-, i-, s- or t-butoxycarbonylmethoxy, methoxycarbonylethoxy, ethoxycarbonylethoxy, n- or i-propoxycarbonylethoxy, n-, i-, s- or t-butoxycarbonylethoxy, methoxycarbonylmethylthio, ethoxycarbonylmethylthio, n- or i-propoxycarbonylmethylthio, n-, i-, s- or t-butoxycarbonylmethylthio, methoxycarbonylethylthio, ethoxycarbonylethylthio, n- or i-propoxycarbonylethylthio, n-, i-, s- or t-butoxycarbonylethylthio, propenyloxycarbonylmethoxy, butenyloxycarbonylmethoxy, propenyloxycarbonylethoxy, butenyloxycarbonylethoxy, propenyloxycarbonylmethylthio, butenyloxycarbonylmethylthio, propenyloxycarbonylethylthio, butenyloxycarbonylethylthio, propynyloxycarbonylmethoxy, butynyloxycarbonylmethoxy, propynyloxycarbonylethoxy, butynyloxycarbonylethoxy, propynyloxycarbonylmethylthio, butynyloxycarbonylmethylthio, propynyloxycarbonylethylthio, butynyloxycarbonylethylthio, methylaminocarbonylmethoxy, ethylaminocarbonylethoxy, n- or i-propylaminocarbonylmethoxy, n-, i-, s- or t-butylaminocarbonylmethoxy, methylaminocarbonylethoxy, ethylaminocarbonylethoxy, n- or i-propylaminocarbonylethoxy, n-, i-, s- or t-butylaminocarbonylethoxy, methylaminocarbonylmethylthio, ethylaminocarbonylmethylthio, n- or i-propylaminocarbonylmethylthio, n-, i-, s- or t-butylaminocarbonylmethylthio, methylaminocarbonylethylthio, ethylaminocarbonylethylthio, n- or i-propylaminocarbonylethylthio, n-, i-, s- or t-butylaminocarbonylethylthio, dimethylaminocarbonylmethoxy, diethylaminocarbonylmethoxy, dimethylaminocarbonylethoxy, diethylaminocarbonylethoxy, dimethylaminocarbonylmethylthio, diethylaminocarbonylmethylthio, dimethylaminocarbonylethylthio, diethylaminocarbonylethylthio, dipropenylaminocarbonylmethoxy, dipropenylaminocarbonylethoxy, dipropenylaminocarbonylmethylthio, dipropenylaminocarbonylethylthio, dipropynylaminocarbonylmethoxy, dipropynylaminocarbonylethoxy, dipropynylaminocarbonylmethylthio or dipropynylaminocarbonylethylthio.

A further very particularly preferred group are those compounds of the formula (I) in which Q represents oxygen or sulphur, $R^1$ represents hydrogen, amino or methyl, $R^2$ represents cyano or trifluoromethyl, $R^3$ represents hydrogen, chlorine or methyl, $R^4$ represents hydrogen, fluorine or chlorine, $R^5$ represents cyano, thiocarbamoyl, chlorine, bromine or trifluoromethyl, $R^6$ represents hydrogen, represents in each case optionally cyano-, fluorine-, chlorine-, methoxy-, ethoxy-, methylthio-, ethylthio-, methylsulphinyl-, ethylsulphinyl-, methylsulphonyl-, ethylsulphonyl-, acetyl-, propionyl-, methoxycarbonyl- or ethoxycarbonyl-substituted methyl or ethyl, represents in each case optionally cyano-, fluorine-, chlorine-, bromine-, methoxy- or ethoxy-substituted acetyl, propionyl, methoxycarbonyl, ethoxycarbonyl, represents in each case optionally fluorine- or chlorine-substituted methylsulphonyl or ethylsulphonyl, represents in each case optionally fluorine- or chlorine-substituted propenyl, butenyl, propynyl or butynyl, represents in each case optionally fluorine-, chlorine- or methyl-substituted cyclopropyl or cyclopropylmethyl, cyclopropylcarbonyl or cyclopropylsulphonyl, represents in each case optionally nitro-, cyano-, fluorine-, chlorine-, bromine-, methyl-, ethyl-, n- or i-propyl-, n-, i-, s- or t-butyl-, trifluoromethyl-, chlorodifluoromethyl-, fluorodichloromethyl-, methoxy-, ethoxy-, n- or i-propoxy-, difluoromethoxy-, trifluoromethoxy-, chlorodifluoromethoxy-, fluorodichloromethoxy-, methoxycarbonyl-, ethoxycarbonyl-, n- or i-propoxycarbonyl-substituted phenyl, phenylmethyl, phenylethyl, benzoyl, phenylacetyl, phenylsulphonyl or phenylmethylsulphonyl, or represents in each case optionally nitro-, cyano-, fluorine-, chlorine-, bromine-, methyl-, ethyl-, n- or i-propyl-, n-, i-, s- or t-butyl-, trifluoromethyl-, chlorodifluoromethyl-, fluorodichloromethyl-, methoxy-, ethoxy-, n- or i-propoxy-, n-, i-, s- or t-butoxy-, difluoromethoxy-, trifluoromethoxy-, chlorodifluoromethoxy-, fluorodichloromethoxy-, methoxycarbonyl-, ethoxycarbonyl-, n- or i-propoxycarbonyl-, n-, i-, s- or t-butoxycarbonyl-substituted heterocyclylcarbonyl, heterocyclylmethylcarbonyl, heterocyclylsulphonyl or heterocyclylmethylsulphonyl, where the heterocyclyl grouping is selected from the group consisting of furyl, tetrahydrofuryl, thienyl, pyrrolyl, pyrrolinyl, pyrrolidinyl, oxopyrrolidinyl, pyrrolyl, pyrazolyl, oxazolyl, oxazolinyl, oxazolidinyl, isoxazolyl, thiazolyl, thiazolinyl, thiazolidinyl, cyanoiminothiazolidinyl, imidazolyl, imidazolinyl, 2-oxo-1,3-diazacyclopentyl (2-oxoimidazolidinyl), triazolyl, oxotriazolinyl, thioxotriazolinyl, pyridinyl, piperidinyl, oxopiperidinyl, 2-oxo-1,3-diazacyclohexyl, morpholinyl, piperazinyl, and $R^7$ represents hydroxyamino, represents N-methylhydroxyamino, N-ethylhydroxyamino, N-n-propylhydroxyamino, N-i-propylhydroxyamino, methoxyamino, ethoxyamino, n- or i-propoxyamino, n-, i-, s- or t-butoxyamino, N-methylmethoxyamino, N-ethylmethoxyamino, N-methylethoxyamino, methoxycarbonylmethoxyamino, ethoxycarbonylmethoxyamino, n- or i-propoxycarbonylmethoxyamino, methoxycarbonylethoxyamino, ethoxycarbonylethoxyamino, n- or i-propoxycarbonylethoxyamino, N-methylmethoxycarbonylmethoxyamino, N-methylethoxycarbonylmethoxyamino, N-methyl-n-propoxycarbonylmethoxyamino, N-methyl-i-propoxycarbonylmethoxyamino, N-methyl-methoxycarbonylethoxyamino, N-methylethoxycarbonylethoxyamino, N-methyl-n-propoxycarbonylethoxyamino, N-methyl-i-propoxycarbonylethoxyamino, propenyloxyamino, butenyloxyamino, N-methyl-propenyloxyamino, N-methylbutenyloxyamino, N-propenylmethoxyamino, N-propenylethoxyamino, N-propenyl-n-propoxyamino, N-propenyl-i-propoxyamino, N-propenylpropenyloxyamino, or represents phenoxyamino or N-methylphenoxyamino.

A further very particularly preferred group are those compounds of the formula (I) in which Q represents oxygen or sulphur, $R^1$ represents hydrogen, amino or methyl, $R^2$ represents cyano or trifluoromethyl, $R^3$ represents hydrogen, chlorine or methyl, $R^4$ represents hydrogen, fluorine or chlorine, $R^5$ represents cyano, thiocarbamoyl, chlorine, bromine or trifluoromethyl, $R^6$ represents hydrogen, represents in each case optionally cyano-, fluorine-, chlorine-, methoxy-, ethoxy-, methylthio-, ethylthio-, methylsulphinyl-, ethylsulphinyl-, methylsulphonyl-, ethylsulphonyl-, acetyl-, propionyl-, methoxycarbonyl- or ethoxycarbonyl-substituted methyl or ethyl, represents in each case optionally cyano-, fluorine-, chlorine-, bromine-, methoxy- or ethoxy-substituted acetyl, propionyl, methoxycarbonyl, ethoxycarbonyl, represents in each case optionally fluorine- or chlorine-substituted methylsulphonyl or ethylsulphonyl, represents in each case optionally fluorine- or chlorine-substituted propenyl, butenyl, propynyl or butynyl, represents in each case optionally fluorine-, chlorine- or methyl-substituted cyclopropyl or cyclopropylmethyl, cyclopropylcarbonyl or cyclopropylsulphonyl, represents in each case optionally nitro-, cyano-, fluorine-, chlorine-, bromine-, methyl-, ethyl-, n- or i-propyl-, n-, i-, s- or t-butyl-, trifluoromethyl-, chlorodifluoromethyl-, fluorodichloromethyl-, methoxy-, ethoxy-, n- or i-propoxy-, difluoromethoxy-, trifluoromethoxy-, chlorodifluoromethoxy-, fluorodichloromethoxy-, methoxycarbonyl-, ethoxycarbonyl-, n- or i-propoxycarbonyl-substituted phenyl, phenylmethyl, phenylethyl, benzoyl, phenylacetyl, phenylsulphonyl or phenylmethylsulphonyl, or represents in each case optionally nitro-, cyano-, fluorine-, chlorine-, bromine-, methyl-, ethyl-, n- or i-propyl-, n-, i-, s- or t-butyl-, trifluoromethyl-, chlorodifluoromethyl-, fluorodichloromethyl-, methoxy-, ethoxy-, n- or i-propoxy-, n-, i-, s- or t-butoxy-, difluoromethoxy-, trifluoromethoxy-, chlorodifluoromethoxy-, fluorodichloromethoxy-, methoxycarbonyl-, ethoxycarbonyl-, n- or i-propoxycarbonyl-, n-, i-, s- or t-butoxycarbonyl-substituted heterocyclylcarbonyl, heterocyclylmethylcarbonyl, heterocyclylsulphonyl or heterocyclylmethylsulphonyl, where the heterocyclyl grouping is selected from the group consisting of furyl, tetrahydrofuryl, thienyl, pyrrolyl, pyrrolinyl, pyrrolidinyl, oxopyrrolidinyl, pyrrolyl, pyrazolyl, oxazolyl, oxazolinyl, oxazolidinyl, isoxazolyl, thiazolyl, thiazolinyl, thiazolidinyl, cyanoiminothiazolidinyl, imidazolyl, imidazolinyl, 2-oxo-1,3-diaza-cyclopentyl (2-oxoimidazolidinyl), triazolyl, oxotriazolinyl, thioxotriazolinyl, pyridinyl, piperidinyl, oxopiperidinyl, 2-oxo-1,3-diazacyclohexyl, morpholinyl, piperazinyl, and $R^7$ represents cyanoethylamino, cyanopropylamino or cyanobutylamino, represents dimethylamino, diethylamino, di-n-propylamino, di-i-propylamino, di-n-butylamino or di-i-butylamino, represents N-methylcyanoethylamino, N-ethylcyanoethylamino, N-n-propylcyanoethylamino, N-i-propylcyanoethylamino, N-methylfluoroethylamino, N-ethylfluoroethylamino, N-n-propylfluoroethylamino, N-i-propylfluoroethylamino, N-methylmethoxyethylamino, N-ethylmethoxyethylamino, N-methylethoxyethylamino, N-ethylethoxyethylamino, N-methylmethoxycarbonylmethylamino, N-methylethoxycarbonylmethylamino, N-methylmethoxycarbonylethylamino, N-methylethoxycarbonylethylamino, represents N-methyl-N-propenylamino, N-methyl-N-butenylamino, N-ethyl-N-propenylamino, N-ethyl-N-butenylamino, N-propyl-N-propenylamino, N-propyl-N-butenylamino, N-butyl-N-propenylamino, N-butyl-N-butenylamino, N-methyl-N-propynylamino, N-methyl-N-butynylamino, N-ethyl-N-propynylamino, N-ethyl-N-butynylamino, N-propyl-N-propynylamino, N-propyl-N-butynylamino, N-butyl-N-propynylamino or N-butyl-N-butynylamino, or represents dipropenylamino, dibutenylamino, dipropynylamino or dibutynylamino.

A further very particularly preferred group are those compounds of the formula (I) in which
Q represents oxygen or sulphur,
$R^1$ represents hydrogen, amino or methyl,
$R^2$ represents cyano or trifluoromethyl,
$R^3$ represents hydrogen, chlorine or methyl,
$R^4$ represents hydrogen, fluorine or chlorine,
$R^5$ represents cyano, thiocarbamoyl, chlorine, bromine or trifluoromethyl,
$R^6$ represents hydrogen, represents in each case optionally cyano-, fluorine-, chlorine-, methoxy-, ethoxy-, methylthio-, ethylthio-, methylsulphinyl-, ethylsulphinyl-, methylsulphonyl-, ethylsulphonyl-, acetyl-, propionyl-, methoxycarbonyl- or ethoxycarbonyl-substituted methyl or ethyl, represents in each case optionally cyano-, fluorine-, chlorine-, bromine-, methoxy- or ethoxy-substituted acetyl, propionyl, methoxycarbonyl, ethoxycarbonyl, represents in each case optionally fluorine- or chlorine-substituted methylsulphonyl or ethylsulphonyl, represents in each case optionally fluorine- or chlorine-substituted propenyl, butenyl, propynyl or butynyl, represents in each case optionally fluorine-, chlorine- or methyl-substituted cyclopropyl or cyclopropylmethyl, cyclopropylcarbonyl or cyclopropylsulphonyl, represents in each case optionally nitro-, cyano-, fluorine-, chlorine-, bromine-, methyl-, ethyl-, n- or i-propyl-, n-, i-, s- or t-butyl-, trifluoromethyl-, chlorodifluoromethyl-, fluorodichloromethyl-, methoxy-, ethoxy-, n- or i-propoxy-, difluoromethoxy-, trifluoromethoxy-, chlorodifluoromethoxy-, fluorodichloromethoxy-, methoxycarbonyl-, ethoxycarbonyl-, n- or i-propoxycarbonyl-substituted phenyl, phenylmethyl, phenylethyl, benzoyl, phenylacetyl, phenylsulphonyl or phenylmethylsulphonyl, or represents in each case optionally nitro-, cyano-, fluorine-, chlorine-, bromine-, methyl-, ethyl-, n- or i-propyl-, n-, i-, s- or t-butyl-, trifluoromethyl-, chlorodifluoromethyl-, fluorodichloromethyl-, methoxy-, ethoxy-, n- or i-propoxy-, n-, i-, s- or t-butoxy-, difluoromethoxy-, trifluoromethoxy-, chlorodifluoromethoxy-, fluorodichloromethoxy-, methoxycarbonyl-, ethoxycarbonyl-, n- or i-propoxycarbonyl-, n-, i-, s- or t-butoxycarbonyl-substituted heterocyclylcarbonyl, heterocyclylmethylcarbonyl, heterocyclylsulphonyl or heterocyclylmethylsulphonyl, where the heterocyclyl grouping is selected from the group consisting of furyl, tetrahydrofuryl, thienyl, pyrrolyl, pyrrolinyl, pyrrolidinyl, oxopyrrolidinyl, pyrrolyl, pyrazolyl, oxazolyl, oxazolinyl, oxazolidinyl, isoxazolyl, thiazolyl, thiazolinyl, thiazolidinyl, cyanoiminothiazolidinyl, imidazolyl, imidazolinyl, 2-oxo-1,3-diazacyclopentyl (2-oxoimidazolidinyl), triazolyl, oxotriazolinyl, thioxotriazolinyl, pyridinyl, piperidinyl, oxopiperidinyl, 2-oxo-1,3-diazacyclohexyl, morpholinyl, piperazinyl, and $R^7$ represents in each case optionally nitro-, cyano-, fluorine-, chlorine-, bromine-, methyl-, ethyl-, n- or i-propyl-, n-, i-, s- or t-butyl-, difluoromethyl-, dichloromethyl-, trifluoromethyl-, chlorodifluoromethyl-, fluorodichloromethyl-, methoxy-, ethoxy-, n- or i-propoxy-, n-, i-, s- or t-butoxy-, difluoromethoxy-, trifluoromethoxy-, chlorodifluoromethoxy-, methylthio-, ethylthio-, n- or i-propylthio-, n-, i-, s- or t-butylthio-, difluoromethylthio-, trifluoromethylthio-, chlorodifluoromethylthio-, methoxycarbonyl-, ethoxycarbonyl-, n- or i-propoxycarbonyl-, n-, i-, s- or t-butoxycarbonyl-, cyclopropyl-, cyclobutyl-, cyclopentyl-, cyclohexyl- or phenyl-substituted heterocyclyloxy, heterocyclylthio, heterocyclylamino, N-methylheterocyclylamino, N-methylheterocyclylmethylamino or —N=(heterocyclyl), where the heterocyclyl grouping is selected from the group consisting of furyl, tetrahydrofuryl, thienyl, pyrrolyl, pyrrolinyl, pyrrolidinyl, oxopyrrolidinyl, pyrrolyl, pyrazolyl, oxazolyl, oxazolinyl, oxazolidinyl, isoxazolyl, thiazolyl, thiazolinyl, thiazolidinyl, cyanoiminothiazolidinyl, imidazolyl, imidazolinyl, 2-oxo-1,3-diazacyclopentyl (2-oxoimidazolidinyl), triazolyl, oxotriazolinyl, thioxotriazolinyl, pyridinyl, piperidinyl, oxopiperidinyl, 2-oxo-1,3-diazacyclohexyl, morpholinyl, piperazinyl, pyrimidinyl.

A further very particularly preferred group are those compounds of the formula (I) in which
Q represents oxygen or sulphur,
$R^1$ represents hydrogen, amino or methyl,
$R^2$ represents cyano or trifluoromethyl,
$R^3$ represents hydrogen, chlorine or methyl,
$R^4$ represents hydrogen, fluorine or chlorine,
$R^5$ represents cyano, thiocarbamoyl, chlorine, bromine or trifluoromethyl, $R^6$ represents hydrogen, represents in each case optionally cyano-, fluorine-, chlorine-, methoxy-, ethoxy-, methylthio-, ethylthio-, methylsulphinyl-, ethylsulphinyl-, methylsulphonyl-, ethylsulphonyl-, acetyl-, propionyl-, methoxycarbonyl- or ethoxycarbonyl-substituted methyl or ethyl, represents in each case optionally cyano-, fluorine-, chlorine-, bromine-, methoxy- or ethoxy-substituted acetyl, propionyl, methoxycarbonyl, ethoxycarbonyl, represents in each case optionally fluorine- or chlorine-substituted methylsulphonyl or ethylsulphonyl, represents in each case optionally fluorine- or chlorine-substituted propenyl, butenyl, propynyl or butynyl, represents in each case optionally fluorine-, chlorine- or methyl-substituted cyclopropyl or cyclopropylmethyl, cyclopropylcarbonyl or cyclopropylsulphonyl, represents in each case optionally nitro-, cyano-, fluorine-, chlorine-, bromine-, methyl-, ethyl-, n- or i-propyl-, n-, i-, s- or t-butyl-, trifluoromethyl-, chlorodifluoromethyl-, fluorodichloromethyl-, methoxy-, ethoxy-, n- or i-propoxy-, difluoromethoxy-, trifluoromethoxy-, chlorodifluoromethoxy-, fluorodichloromethoxy-, methoxycarbonyl-, ethoxycarbonyl-, n- or i-propoxycarbonyl-substituted phenyl, phenylmethyl, phenylethyl, benzoyl, phenylacetyl, phenylsulphonyl or phenylmethylsulphonyl, or represents in each case optionally nitro-, cyano-, fluorine-, chlorine-, bromine-, methyl-, ethyl-, n- or i-propyl-, n-, i-, s- or t-butyl-, trifluoromethyl-, chlorodifluoromethyl-, fluorodichloromethyl-, methoxy-, ethoxy-, n- or i-propoxy-, n-, i-, s- or t-butoxy-, difluoromethoxy-, trifluoromethoxy-, chlorodifluoromethoxy-, fluorodichloromethoxy-, methoxycarbonyl-, ethoxycarbonyl-, n- or i-propoxycarbonyl-, n-, i-, s- or t-butoxycarbonyl-substituted heterocyclylcarbonyl, heterocyclylmethylcarbonyl, heterocyclylsulphonyl or heterocyclylmethylsulphonyl, where the heterocyclyl grouping is selected from the group consisting of furyl, tetrahydrofuryl, thienyl, pyrrolyl, pyrrolinyl, pyrrolidinyl, oxopyrrolidinyl, pyrrolyl, pyrazolyl, oxazolyl, oxazolinyl, oxazolidinyl, isoxazolyl, thiazolyl, thiazolinyl, thiazolidinyl, cyanoiminothiazolidinyl, imidazolyl, imidazolinyl, 2-oxo-1,3-diazacyclopentyl (2-oxoimidazolidinyl), triazolyl, oxotriazolinyl, thioxotriazolinyl, pyridinyl, piperidinyl, oxopiperidinyl, 2-oxo-1,3-diazacyclohexyl, morpholinyl, piperazinyl, and $R^7$ represents a monocyclic or bicyclic nitrogen heterocycle from the group consisting of pyrrolyl, pyrrolinyl, pyrrolidinyl, oxopyrrolidinyl, pyrazolyl, imidazolyl, imidazolinyl, 2-oxo-1,3-diazacyclopentyl (2-oxoimidazolidinyl), 2-oxo-1,3-oxazacyclopentyl (2-oxooxazolidinyl), isoxazolidinyl, thiazolinyl, 2-oxothiazolidinyl, 1,1-dioxoisothiazolidinyl, 2-cyanoiminothiazolidinyl, triazolyl, oxotriazolinyl, thioxotriazolinyl, pyridinyl, piperidinyl, oxopiperidinyl, 2-oxo-1,3-diazacyclohexyl, morpholinyl, piperazinyl, which is attached via N and is optionally substituted by nitro, cyano, fluorine, chlorine, bromine, methyl, ethyl, n- or i-propyl, n-, i-, s- or t-butyl, difluoromethyl, dichloromethyl, trifluoromethyl, chlorodifluoromethyl, fluorodichloromethyl, methoxy, ethoxy, n- or i-propoxy, n-, i-, s- or t-butoxy, difluoromethoxy, trifluoromethoxy, chlorodifluoromethoxy, methylthio, ethylthio, n- or i-propylthio, n-, i-, s- or t-butylthio, difluoromethylthio, trifluoromethylthio, chlorodifluoromethylthio, methoxycarbonyl, ethoxycarbonyl, n- or i-propoxycarbonyl, n-, i-, s- or t-butoxycarbonyl, cyclopropyl, cyclobutyl, cyclopentyl, cyclohexyl or phenyl.

The general or preferred radical definitions listed above apply both to the end products of the formula (I) and, correspondingly, to the starting materials or intermediates required in each case for the preparation. These radical definitions can be combined with one another as desired, i.e. including combinations between the given preferred ranges.

The novel substituted (thioxo)carbonylaminophenyluracils of the general formula (I) have potent and selective herbicidal activity.

The novel substituted (thioxo)carbonylaminophenyluracils of the general formula (I) are obtained with iso(thio)cyanatophenyluraciles of the general formula (II)

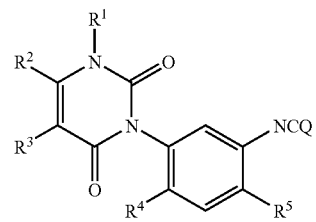

(II)

in which

Q, $R^1$, $R^2$, $R^3$, $R^4$ and $R^5$ are as defined above, are reacted with compounds of the general formula (III)

H—$R^7$ (III)

in which $R^7$ is as defined above, if appropriate in the presence of one or more reaction auxiliaries and if appropriate in the presence of one or more diluents, and the resulting substituted (thioxo)carbonylaminophenyluracils of the general formula (Ia)

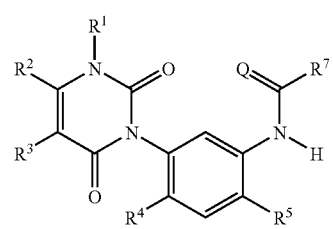

(Ia)

in which

Q, $R^1$, $R^2$, $R^3$, $R^4$, $R^5$ and $R^7$ are as defined above are, if appropriate, reacted with compounds of the general formula (IV)

X—$R^6$ (IV)

in which $R^6$ is as defined above, except for hydrogen, and

X represents halogen (in particular chlorine, bromine or iodine), or optionally also represents acetyloxy, propionyloxy, methoxysulphonyloxy or ethoxysulphonyloxy, if appropriate in the presence of one or more reaction auxiliaries and if appropriate in the presence of one or more diluents.

Using, for example, 3-(2,4-dichlorio-5-isothiocyanatophenyl)-1-methyl-6-trifluoromethyl-1H-pyrimidine-2,4-dione and N,O-dimethylhydroxylamine as starting materials, the course of the reaction in the process according to the invention can be illustrated by the formula scheme below:

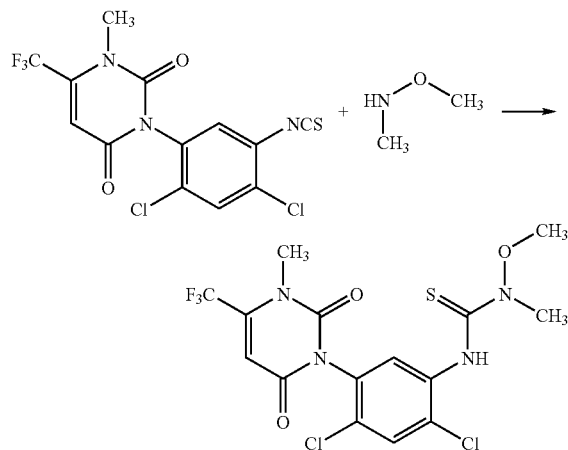

The formula (II) provides a general definition of the (thioxo)carbonylaminophenyluracils to be used as starting materials in the process according to the invention for preparing compounds of the formula (I). In the formula (II), Q, $R^1$, $R^2$, $R^3$, $R^4$ and $R^5$ preferably have those meanings which have already been mentioned above, in connection with the description of the compounds of the formula (I) according to the invention, as being preferred, particularly preferred or very particularly preferred for Q, $R^1$, $R^2$, $R^3$, $R^4$ and $R^5$.

Except for the compound 3-(4-chloro-2-fluoro-5-isothiocyanatophenyl)-1-methyl-6-trifluoromethyl-2,4-(1H,3H)-pyrimidinedione (cf. U.S. Pat. No. 6,303,783), the starting materials of the general formula (II) have hitherto not been disclosed in the literature; except for the compound 3-(4-chloro-2-fluoro-5-isothiocyanatophenyl)-1-methyl-6-trifluoromethyl-2,4-(1H,3H)-pyrimidinedione they also form, as novel substances, part of the subject-matter of the present application.

The iso(thio)cyanatophenyluracils of the general formula (II) are obtained when aminophenyluracils of the general formula (V)

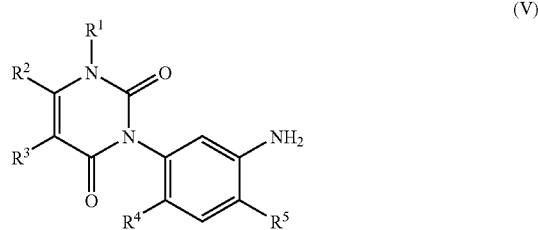

in which
$R^1$, $R^2$, $R^3$, $R^4$ and $R^5$ are as defined above,
are reacted with phosgene (or diphosgene) or thiophosgene, if appropriate in the presence of a reaction auxiliary such as, for example, diazabicyclo[2.2.2]octane, and in the presence of a diluent, such as, for example, acetone, toluene, xylene or chlorobenzene, at temperatures between 0° C. and 150° C., and the volatile components are distilled off under reduced pressure after the reaction has ended (cf. the Preparation Examples). The compounds of the formula (V) are known compounds.

The formulae (III) and (IV) provide general definitions of the compounds further to be used as starting materials. Here, $R^6$ and $R^7$ preferably have those meanings which have already been mentioned above, in connection with the description of the compounds of the formula (I) according to the invention, as being preferred, particularly preferred, very particularly preferred or most preferred for $R^6$ and $R^7$, respectively.

The starting materials of the formulae (III) and (IV) are known chemicals of synthesis.

The process according to the invention for preparing the compounds of the general formula (I) is preferably carried out using a reaction auxiliary. Reaction auxiliaries suitable for the process according to the invention are, in general, the customary inorganic or organic bases or acid acceptors. These preferably include alkali metal or alkaline earth metal acetates, amides, carbonates, bicarbonates, hydrides, hydroxides or alkoxides, such as, for example, sodium acetate, potassium acetate or calcium acetate, lithium amide, sodium amide, potassium amide or calcium amide, sodium carbonate, potassium carbonate or calcium carbonate, sodium bicarbonate, potassium bicarbonate or calcium bicarbonate, lithium hydride, sodium hydride, potassium hydride or calcium hydride, lithium hydroxide, sodium hydroxide, potassium hydroxide or calcium hydroxide, sodium methoxide, ethoxide, n- or i-propoxide, n-, i-, s- or t-butoxide or potassium methoxide, ethoxide, n- or i-propoxide, n-, i-, s- or t-butoxide; furthermore also basic organic nitrogen compounds, such as, for example, trimethylamine, triethylamine, tripropylamine, tributylamine, ethyldiisopropylamine, N,N-dimethylcyclohexylamine, dicyclohexylamine, ethyldicyclohexylamine, N,N-dimethylaniline, N,N-dimethylbenzylamine, pyridine, 2-methyl-, 3-methyl-, 4-methyl-, 2,4-dimethyl-, 2,6-dimethyl-, 3,4-dimethyl- and 3,5-dimethylpyridine 5-ethyl-2-methylpyridine, 4-dimethylaminopyridine, N-methylpiperidine, 1,4-diazabicyclo[2.2.2]octane (DABCO), 1,5-diazabicyclo[4.3.0]non-5-ene (DBN) or 1,8-diazabicyclo[5.4.0]undec-7-ene (DBU).

The process according to the invention for preparing the compounds of the general formula (I) is preferably carried out using a diluent. Diluents suitable for carrying out the process according to the invention are especially inert organic solvents. These include, in particular, aliphatic, alicyclic or aromatic, optionally halogenated hydrocarbons, such as benzine, benzene, toluene, xylene, chlorobenzene, dichlorobenzene, petroleum ether, hexane, cyclohexane, dichloromethane, chloroform, carbon tetrachloride; ethers, such as diethyl ether, diisopropyl ether, dioxane, tetrahydrofuran or ethylene glycol dimethyl ether or ethylene glycol diethyl ether; ketones, such as acetone, butanone or methyl isobutyl ketone; nitrites, such as acetonitrile, propionitrile or butyronitrile; amides, such as N,N-dimethylformamide, N,N-dimethylacetamide, N-methylformanilide, N-methylpyrrolidone or hexamethylphosphoric triamide; esters, such as methyl acetate or ethyl acetate; sulphoxides, such as dimethyl sulphoxide; alcohols, such as methanol, ethanol, n- or i-propanol, ethylene glycol monomethyl ether, ethylene glycol monoethyl ether, diethylene glycol monomethyl ether, diethylene glycol monoethyl ether, mixtures thereof with water or pure water.

When carrying out the process according to the invention, the reaction temperatures can be varied within a relatively wide range. In general, the process is carried out at temperatures between 0° C. and 150° C., preferably between 10° C. and 120° C.

The process according to the invention is generally carried out under atmospheric pressure. However, it is also possible to carry out the process according to the invention under elevated or reduced pressure—in general between 0.1 bar and 10 bar.

For carrying out the process according to the invention, the starting materials are generally employed in approximately equimolar amounts. However, it is also possible to use a relatively large excess of one of the components. The reaction is generally carried out in a suitable diluent in the presence of a reaction auxiliary and the reaction mixture is generally stirred at the required temperature for a number of hours. Work-up is carried out by customary methods (cf. the Preparation Examples).

The active compounds according to the invention can be used as defoliants, desiccants, haulm killers and, especially, as weed killers. Weeds in the broadest sense are understood to mean all plants which grow in locations where they are undesired. Whether the substances according to the invention act as total or selective herbicides depends essentially on the amount used.

The active compounds according to the invention can be used, for example, in connection with the following plants:

Dicotyledonous weeds of the genera: *Abutilon, Amaranthus, Ambrosia, Anoda, Anthemis, Aphanes, Atriplex, Bellis, Bidens, Capsella, Carduus, Cassia, Centaurea, Chenopodium, Cirsium, Convolvulus, Datura, Desmodium, Emex, Erysimum, Euphorbia, Galeopsis, Galinsoga, Galium, Hibiscus, Ipomoea, Kochia, Lamium, Lepidium, Lindernia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsola, Senecio, Sesbania, Sida, Sinapis, Solanum, Sonchus, Sphenoclea, Stellaria, Taraxacum, Thlaspi, Trifolium, Urtica, Veronica, Viola, Xanthium.*

Dicotyledonous crops of the genera: *Arachis, Beta, Brassica, Cucumis, Cucurbita, Helianthus, Daucus, Glycine, Gossypium, Ipomoea, Lactuca, Linum, Lycopersicon, Nicotiana, Phaseolus, Pisum, Solanum, Vicia.*

Monocotyledonous weeds of the genera: *Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria, Sorghum.*

Monocotyledonous crops of the genera: *Allium, Ananas, Asparagus, Avena, Hordeum, Oryza, Panicum, Saccharum, Secale, Sorghum, Triticale, Triticum, Zea.*

However, the use of the active compounds according to the invention is in no way restricted to these genera, but also extends in the same manner to other plants.

The active compounds according to the invention are suitable, depending on the concentration, for the total control of weeds, for example on industrial terrain and rail tracks, and on paths and areas with and without tree plantings. Similarly, the active compounds according to the invention can be employed for controlling weeds in perennial crops, for example forests, decorative tree plantings, orchards, vineyards, citrus groves, nut orchards, banana plantations, coffee plantations, tea plantations, rubber plantations, oil palm plantations, cocoa plantations, soft fruit plantings and hop fields, on lawns, turf and pastureland, and for the selective control of weeds in annual crops.

The compounds of the formula (I) according to the invention have strong herbicidal activity and a broad active spectrum when used on the soil and on above-ground parts of plants. To a certain extent they are also suitable for the selective control of monocotyledonous and dicotyledonous weeds in monocotyledonous and dicotyledonous crops, both by the pre-emergence and by the post-emergence method.

At certain concentrations or application rates, the active compounds according to the invention can also be employed for controlling animal pests and fungal or bacterial plant diseases. If appropriate, they can also be used as intermediates or precursors for the synthesis of other active compounds.

All plants and plant parts can be treated in accordance with the invention. Plants are to be understood as meaning in the present context all plants and plant populations such as desired and undesired wild plants or crop plants (including naturally occurring crop plants). Crop plants can be plants which can be obtained by conventional plant breeding and optimization methods or by biotechnological and genetic engineering methods or by combinations of these methods, including the transgenic plants and inclusive of the plant cultivars protectable or not protectable by plant breeders' rights. Plant parts are to be understood as meaning all parts and organs of plants above and below the ground, such as shoot, leaf, flower and root, examples which may be mentioned being leaves, needles, stalks, stems, flowers, fruit bodies, fruits, seeds, roots, tubers and rhizomes. The plant parts also include harvested material, and vegetative and generative propagation material, for example cuttings, tubers, rhizomes, offsets and seeds.

Treatment according to the invention of the plants and plant parts with the active compounds is carried out directly or by allowing the compounds to act on their surroundings, environment or storage space by the customary treatment methods, for example by immersion, spraying, evaporation, fogging, scattering, painting on and, in the case of propagation material, in particular in the case of seeds, also by applying one or more coats.

The active compounds can be converted into the customary formulations such as solutions, emulsions, wettable powders, suspensions, powders, dusts, pastes, soluble powders, granules, suspension-emulsion concentrates, natural and synthetic materials impregnated with active compound, and microencapsulations in polymeric materials.

These formulations are produced in a known manner, for example by mixing the active compounds with extenders, that is, liquid solvents and/or solid carriers, optionally with the use of surfactants, that is, emulsifiers and/or dispersants, and/or foam formers.

If the extender used is water, it is also possible, for example, to use organic solvents as cosolvents. The following are essentially suitable as liquid solvents: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example mineral oil fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, or else water.

Suitable solid carriers are: for example ammonium salts and ground natural minerals such as kaolins, clays, talc, chalk, quartz, attapulgite, montmorillonite or diatomaceous earth, and ground synthetic materials such as highly-disperse silica, alumina and silicates; suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks; suitable emulsifiers and/or foam formers are: for example nonionic and anionic emulsifiers such as polyoxyethylene fatty acid esters, polyoxyethylene fatty alcohol ethers, for example alkylaryl polyglycol ethers, alkylsulphonates, alkyl sulphates, arylsulphonates, or else protein hydrolysates; suitable dispersants are: for example lignin-sulphite waste liquors and methylcellulose.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other additives can be mineral and vegetable oils.

It is possible to use colorants such as inorganic pigments, for example iron oxide, titanium oxide and Prussian Blue, and organic colorants such as alizarin colorants, azo colorants and metal phthalocyanine colorants, and trace nutrients such as salts of iron, manganese, boron, copper, cobalt, molybdenum and zinc.

The formulations generally comprise between 0.1 and 95% by weight of active compound, preferably between 0.5 and 90%.

For controlling weeds, the active compounds according to the invention, as such or in their formulations, can also be used as mixtures with known herbicides and/or substances which improve the compatibility with crop plants ("safeners"), finished formulations or tank mixes being possible. Also possible are mixtures with weed-killers comprising one or more known herbicides and a safener.

Possible components for the mixtures are known herbicides, for example acetochlor, acifluorfen (-sodium), aclonifen, alachlor, alloxydim (-sodium), ametryne, amicarbazone, amidochlor, amidosulfuron, anilofos, asulam, atrazine, azafenidin, azimsulfuron, beflubutamid, benazolin (-ethyl), benfuresate, bensulfuron (-methyl), bentazone, benzfendizone, benzobicyclon, benzofenap, benzoylprop (-ethyl), bialaphos, bifenox, bispyribac (-sodium), bromobutide, bromofenoxim, bromoxynil, butachlor, butafenacil (-allyl), butroxydim, butylate, cafenstrole, caloxydim, carbetamide, carfentrazone (-ethyl), chlomethoxyfen, chloramben, chloridazone, chlorimuron (-ethyl), chlornitrofen, chlorsulfuron, chlortoluron, cinidon (-ethyl), cinmethylin, cinosulfuron, clefoxydim, clethodim, clodinafop (-propargyl), clomazone, clomeprop, clopyralid, clopyrasulfuron (-methyl), cloransulam (-methyl), cumyluron, cyanazine, cybutryne, cycloate, cyclosulfamuron, cycloxydim, cyhalofop (-butyl), 2,4-D, 2,4-DB, desmedipham, diallate, dicamba, dichlorprop (-P), diclofop (-methyl), diclosulam, diethatyl (-ethyl), difenzoquat, diflufenican, diflufenzopyr, dimefuron, dimepiperate, dimethachlor, dimethametryn, dimethenamid, dimexyflam, dinitramine, diphenamid, diquat, dithiopyr, diuron, dymron, epropodan, EPTC, esprocarb, ethalfluralin, ethametsulfuron (-methyl), ethofumesate, ethoxyfen, ethoxysulfuron, etobenzanid, fenoxaprop (-P-ethyl), fentrazamide, flamprop (-isopropyl, -isopropyl-L, -methyl), flazasulfuron, florasulam, fluazifop (-P-butyl), fluazolate, flucarbazone (-sodium), flufenacet, flufenpyr, flumetsulam, flumiclorac (-pentyl), flumioxazin, flumipropyn, flumetsulam, fluometuron, fluorochloridone, fluoroglycofen (-ethyl), flupoxam, flupropacil, flurpyrsulfuron (-methyl, -sodium), flurenol (-butyl), fluridone, fluroxypyr (-butoxypropyl, -meptyl), flurprimidol, flurtamone, fluthiacet (-methyl), fluthiamide, fomesafen, foramsulfuron, glufosinate (-ammonium), glyphosate (-isopropylammonium), halosafen, haloxyfop (-ethoxyethyl, -P-methyl), hexazinone, imazamethabenz (-methyl), imazamethapyr, imazamox, imazapic, imazapyr, imazaquin, imazethapyr, imazosulfuron, iodosulfuron (-methyl, -sodium), ioxynil, isopropalin, isoproturon, isouron, isoxaben, isoxachlortole, isoxaflutole, isoxapyrifop, ketospiradox, lactofen, lenacil, linuron, MCPA, mecoprop, mefenacet, mesotrione, metamitron, metazachlor, methabenzthiazuron, metobenzuron, metobromuron, (alpha-) metolachlor, metosulam, metoxuron, metribuzin, metsulfuron (-methyl), molinate, monolinuron, naproanilide, napropamide, neburon, nicosulfuron, norflurazon, orbencarb, oryzalin, oxadiargyl, oxadiazon, oxasulfuron, oxaziclomefone, oxyfluorfen, paraquat, pelargonic acid, pendimethalin, pendralin, penoxysulam, pentoxazone, pethoxamide, phenmedipham, picolinafen, piperophos, pretilachlor, primisulfuron (-methyl), profluazol, profoxydim, prometryn, propachlor, propanil, propaquizafop, propisochlor, propoxycarbazone (-sodium), propyzamide, prosulfocarb, prosulfuron, pyraflufen (-ethyl), pyrazogyl, pyrazolate, pyrazosulfuron (-ethyl), pyrazoxyfen, pyribenzoxim, pyributicarb, pyridate, pyridatol, pyriftalid, pyriminobac (-methyl), pyrithiobac (-sodium), quinchlorac, quimnerac, quinoclamine, quizalofop (-P-ethyl, -P-tefuryl), rimsulfuron, sethoxydim, simazine, simetryn, sulcotrione, sulfentrazone, sulfometuron (-methyl), sulfosate, sulfosulfuron, tebutam, tebuthiuron, tepraloxydim, terbuthylazine, terbutryn, thenylchlor, thiafluamide, thiazopyr, thidiazimin, thifensulfuron (-methyl), thiobencarb, tiocarbazil, tralkoxydim, triallate, triasulfuron, tribenuron (-methyl), triclopyr, tridiphane, trifluralin, trifloxysulfuron, triflusulfuron (-methyl), tritosulfuron.

Also suitable for the mixtures are known safeners, for example AD-67, BAS-145138, benoxacor, cloquintocet (-mexyl), cymetrinil, 2,4-D, DKA-24, dichlormid, dymron, fenclorim, fenchlorazole (-ethyl), flurazole, fluxofenim, furilazole, isoxadifen (-ethyl), MCPA, mecoprop (-P), mefenpyr (-diethyl), MG-191, oxabetrinil, PPG-1292, R-29148.

A mixture with other known active compounds, such as fungicides, insecticides, acaricides, nematicides, bird repellents, plant nutrients and agents which improve soil structure, is also possible.

The active compounds can be used as such, in the form of their formulations or in the use forms prepared therefrom by further dilution, such as ready-to-use solutions, suspensions, emulsions, powders, pastes and granules. They are used in a customary manner, for example by watering, spraying, atomizing or broadcasting.

The active compounds according to the invention can be applied both before and after emergence of the plants. They can also be incorporated into the soil before sowing.

The amount of active compound used can vary within a relatively wide range. It depends essentially on the nature of the desired effect. In general, the amounts used are between 1 g and 10 kg of active compound per hectare of soil surface, preferably between 5 g and 5 kg per ha.

As already mentioned above, it is possible to treat all plants and their parts according to the invention. In a preferred embodiment, wild plant species and plant cultivars, or those obtained by conventional biological breeding methods, such as crossing or protoplast fusion, and parts thereof, are treated. In a further preferred embodiment, transgenic plants and plant cultivars obtained by genetic engineering, if appropriate in combination with conventional methods (Genetically Modified Organisms), and parts thereof are treated. The term "parts" or "parts of plants" or "plant parts" has been explained above.

Particularly preferably, plants of the plant cultivars which are in each case commercially available or in use are treated according to the invention. Plant cultivars are understood as meaning plants with particular properties ("traits") which are grown by conventional cultivation, by mutagenesis or by recombinant DNA techniques. These may be cultivars, biotypes or genotypes.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the substances and compositions to be used according to the invention—also in combination with other agrochemical compounds, better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products are possible which exceed the effects which were actually to be expected.

The transgenic plants or plant cultivars (i.e. those obtained by genetic engineering) which are preferably to be treated according to the invention include all plants which, in the genetic modification, received genetic material which imparts particularly advantageous useful properties ("traits") to these plants. Examples of such properties are better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products. Further and particularly emphasized examples of such properties are a better defense of the plants against animal and microbial pests, such as against insects, mites, phytopathogenic fungi, bacteria and/or viruses, and also increased tolerance of the plants to certain herbicidally active compounds. Examples of transgenic plants which may be mentioned are the important crop plants, such as cereals (wheat, rice), maize, soya beans, potatoes, cotton, oilseed rape and also fruit plants (with the fruits apples, pears, citrus fruits and grapes), and particular emphasis is given to maize, soya beans, potatoes, cotton and oilseed rape. Traits that are emphasized are in particular increased defence of the plants against insects by toxins formed in the plants, in particular those formed in the plants by the genetic material from *Bacillus thuringiensis* (for example by the genes CryIA(a), CryIA(b), CryIA(c), CryIIA, CryIIIA, CryIIIB2, Cry9c Cry2Ab, Cry3Bb and CryIF and also combinations thereof) (hereinbelow referred to as "Bt plants"). Traits which are also particularly emphasized are the increased resistance of plants to fungi, bacteria and viruses by systemic acquired resistance (SAR), systemin, phytoalexins, elicitors and resistance genes and the correspondingly expressed proteins and toxins. Traits that are furthermore particularly emphasized are the increased tolerance of the plants to certain herbicidally active compounds, for example imidazolinones, sulphonylureas, glyphosate or phosphinotricin (for example the "PAT" gene). The genes which impart the desired traits in question can also be present in combination with one another in the transgenic plants. Examples of "Bt plants" which may be mentioned are maize varieties, cotton varieties, soya bean varieties and potato varieties which are sold under the trade names YIELD GARD® (for example maize, cotton, soya beans), KnockOut® (for example maize), StarLink® (for example maize), Bollgard® (cotton), Nucotn® (cotton) and NewLeaf® (potato). Examples of herbicide-tolerant plants which may be mentioned are maize varieties, cotton varieties and soya bean varieties which are sold under the trade names Roundup Ready® (tolerance to glyphosate, for example maize, cotton, soya bean), Liberty Link® (tolerance to phosphinothricin, for example oilseed rape), IMI® (tolerance to imidazolinones) and STS® (tolerance to sulphonylureas, for example maize). Herbicide-resistant plants (plants bred in a conventional manner for herbicide tolerance) which may be mentioned include the varieties sold under the name Clearfield® (for example maize). Of course, these statements also apply to plant cultivars having these genetic traits or genetic traits still to be developed, which cultivars will be developed and/or marketed in the future.

The plants listed can be treated according to the invention in a particularly advantageous manner with the compounds of the formula I or the active compound mixtures according to the invention where, in addition to the efficient control of the weed plants, the abovementioned synergistic effects with the transgenic plants or plant cultivars may occur. The preferred ranges stated above for the active compounds or mixtures also apply to the treatment of these plants. Particular emphasis is given to the treatment of plants with the compounds or mixtures specifically mentioned in the present text.

The active compounds are also suitable for controlling animal pests, in particular insects, arachnids and nematodes encountered in agriculture, in forests, in the protection of stored products and the protection of materials and in the hygiene sector. They can preferably be used as crop-protecting agents. They are effective against normally sensitive and resistant species and against all or some stages of development.

When used as insecticides, the active compounds according to the invention can furthermore be present in their commercial formulations and in the use forms prepared from these formulations as a mixture with synergists. Synergists are compounds which enhance the action of the active compounds without it being necessary for the added synergist to be active for its part.

The active compound content of the use forms prepared from the commercial formulations can vary within wide ranges. The active compound concentration of the use forms can be from 0.0000001 to 95% by weight of active compound, and is preferably from 0.0001 to 1% by weight.

Application is carried out in a manner suitable for the use forms.

The active compounds of the formula (I) according to the invention are also suitable for controlling arthropods which infest agricultural productive livestock, such as, for example, cattle, sheep, goats, horses, pigs, donkeys, camels, buffalo, rabbits, chickens, turkeys, ducks, geese and bees, other pets, such as, for example, dogs, cats, caged birds and aquarium fish, and also so-called test animals, such as, for example, hamsters, guinea pigs, rats and mice. By controlling these arthropods, cases of death and reduction in productivity (for meat, milk, wool, hides, eggs, honey etc.) should be diminished, so that more economic and easier animal husbandry is possible by use of the active compounds according to the invention.

The active compounds according to the invention are used in the veterinary sector in a known manner by enteral administration in the form of, for example, tablets, capsules, potions, drenches, granules, pastes, boluses, the feed-through process and suppositories, by parenteral administration, such as, for example, by injection (intramuscular, subcutaneous, intravenous, intraperitoneal and the like), implants, by nasal administration, by dermal use in the form, for example, of dipping or bathing, spraying, pouring on and spotting on, washing and powdering, and also with the aid of moulded articles containing the active compound, such as collars, ear marks, tail marks, limb bands, halters, marking devices and the like.

When used for cattle, poultry, pets and the like, the active compounds of the formula (I) can be used as formulations (for example powders, emulsions, free-flowing compositions), which comprise the active compounds in an amount of 1 to 80% by weight, directly or after 100 to 10 000-fold dilution, or they can be used as a chemical bath.

The active compounds are also suitable for controlling animal pests, in particular insects, arachnids and mites, encountered in closed spaces, such as, for example, apartments, factory halls, offices, vehicle cabins and the like. For controlling these pests, they can be used on their own or in combination with other active compounds and auxiliaries in household insecticide products. They are active against sensitive and resistant species and against all stages of development.

They are used in aerosols, pressure-free spray products, for example pump and atomizer sprays, automatic fogging systems, foggers, foams, gels, evaporator products with evaporator tablets made of cellulose or polymer, liquid evaporators, gel and membrane evaporators, propeller-driven evaporators, energy-free or passive evaporation systems, moth papers, moth bags and moth gels, as granules or dusts, in baits for spreading or in bait stations.

The preparation and the use of the active compounds according to the invention is illustrated by the examples below.

PREPARATION EXAMPLES

Example 1

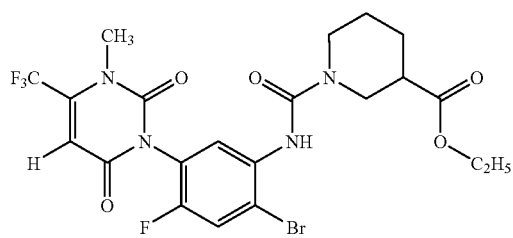

A mixture of 2.50 g (6.1 mmol) of 3-(4-bromo-2-fluoro-5-isocyanatophenyl)-1-methyl-6-trifluoromethyl-1H-pyrimidine-2,4-dione, 0.96 g (6.1 mmol) of ethyl piperidine-3-carboxylate, 2 drops of triethylamine and 30 ml of acetonitrile is stirred at room temperature (about 20° C.) for 15 hours and then concentrated under reduced pressure. The residue is worked up by column chromatography (silica gel, hexane/ethyl acetate, vol.: 2:1).

This gives 1.50 g (42% of theory) of ethyl 1-[2-bromo-4-fluoro-5-(3-methyl-2,6-dioxo-4-trifluoromethyl-3,6-dihydro-2H-pyrimidin-1-yl)phenylcarbamoyl]piperidine-3-carboxylate.

logP (pH 2): 2.98

Analogously to Example 1 and in accordance with the general description of the preparation process according to the invention, it is also possible to prepare, for example, the compounds of the general formula (I) listed in Table 1 below.

TABLE 1

(I)

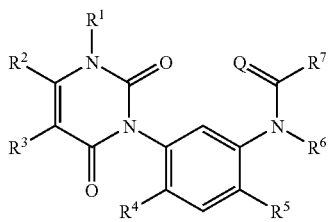

Examples of compounds of the formula (I). In all cases, Q represents oxygen.

| Ex. No. | R¹ | R² | R³ | R⁴ | R⁵ | R⁶ | R⁷ | Physical data |
|---|---|---|---|---|---|---|---|---|
| 2 | CH₃ | CF₃ | H | F | Br | H | 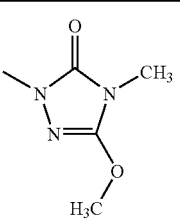 | logP = 2.51[a] |
| 3 | CH₃ | CF₃ | H | F | Br | H | 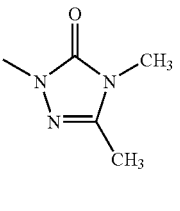 | logP = 2.31[a] |
| 4 | CH₃ | CF₃ | H | F | Br | H | 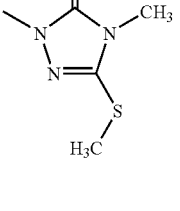 | logP = 2.73[a] |

TABLE 1-continued

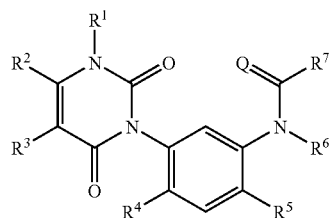

(I)

Examples of compounds of the formula (I). In all cases, Q represents oxygen.

| Ex. No. | R¹ | R² | R³ | R⁴ | R⁵ | R⁶ | R⁷ | Physical data |
|---|---|---|---|---|---|---|---|---|
| 5 | CH₃ | CF₃ | H | F | Br | H | 1,3-dimethylimidazolidin-2-one-yl | logP = 2.55ᵃ⁾ |
| 6 | CH₃ | CF₃ | H | F | Br | H | 1-methyl-3-ethylimidazolidin-2-one-yl | logP = 2.85ᵃ⁾ |
| 7 | CH₃ | CF₃ | H | F | Br | H | 1,3-dimethyltetrahydropyrimidin-2-one-yl | logP = 2.79ᵃ⁾ |
| 8 | CH₃ | CF₃ | H | F | Br | H | N(CH₃)(OCH₃) | logP = 2.67ᵃ⁾ |
| 9 | CH₃ | CF₃ | H | F | Br | H | NH(OCH₃) | logP = 2.19ᵃ⁾ |
| 10 | CH₃ | CF₃ | H | F | Br | H | CH(OCH₃)(CH₃)C(O)OC₂H₅ | logP = 3.06ᵃ⁾ |
| 11 | CH₃ | CF₃ | H | F | Cl | H | 2-(methylthio)-4,5-dihydrothiazol-yl | logP = 3.50ᵃ⁾ |
| 12 | CH₃ | CF₃ | H | F | Cl | H | CH(SCH₃)(CH₃)C(O)OC₂H₅ | logP = 3.11ᵃ⁾ |
| 13 | CH₃ | CF₃ | H | F | Cl | H | CH₂(SCH₃)C(O)OC₂H₅ | logP = 2.80ᵃ⁾ |

TABLE 1-continued

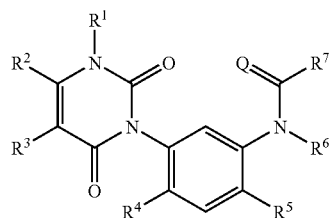

(I)

Examples of compounds of the formula (I). In all cases, Q represents oxygen.

| Ex. No. | R¹ | R² | R³ | R⁴ | R⁵ | R⁶ | R⁷ | Physical data |
|---|---|---|---|---|---|---|---|---|
| 14 | CH₃ | CF₃ | H | F | Cl | H | methyl (methylthio)acetate group | logP = 2.55[a] |
| 15 | CH₃ | CF₃ | H | F | Cl | H | N-methyl cyanomethylamino group | logP = 2.06[a] |
| 16 | CH₃ | CF₃ | H | F | Br | H | 2-(methylthio)-4,5-dihydrothiazole group | logP = 3.53[a] |
| 17 | CH₃ | CF₃ | H | F | Br | H | ethyl 2-(methylthio)propanoate group | logP = 3.15[a] |
| 18 | CH₃ | CF₃ | H | F | Br | H | ethyl (methylthio)acetate group | logP = 2.90[a] |
| 19 | CH₃ | CF₃ | H | F | Br | H | methyl (methylthio)acetate group | logP = 2.59[a] |
| 20 | CH₃ | CF₃ | H | F | Br | H | N-methyl cyanomethylamino group | logP = 2.08[a] |
| 21 | CH₃ | CF₃ | H | F | Cl | H | N-methyl-N-methoxy-methylamino group | logP = 2.60[a] |
| 22 | CH₃ | CF₃ | H | F | Cl | H | N-methyl-O-allyloxy-amino group | logP = 2.60[a] |
| 23 | CH₃ | CF₃ | H | F | Cl | H | 3-methyl-2-(cyanoimino)thiazolidine group | |

TABLE 1-continued

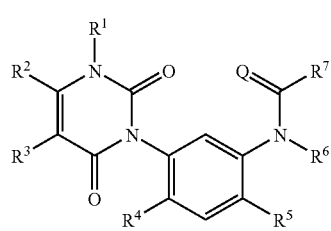

(I)

Examples of compounds of the formula (I). In all cases, Q represents oxygen.

| Ex. No. | $R^1$ | $R^2$ | $R^3$ | $R^4$ | $R^5$ | $R^6$ | $R^7$ | Physical data |
|---|---|---|---|---|---|---|---|---|
| 24 | $CH_3$ | $CF_3$ | H | F | Cl | H | isoxazolidinyl | logP = 2.58[a] |
| 25 | $CH_3$ | $CF_3$ | H | F | Cl | H | oxazolidin-2-one-yl | logP = 2.55[a] |
| 26 | $CH_3$ | $CF_3$ | H | F | Br | H | NH-O-CH(CH=CH$_2$) | logP = 2.67[a] |
| 27 | $CH_3$ | $CF_3$ | H | F | Cl | H | NH-O-C$_2$H$_5$ | logP = 2.45[a] |
| 28 | $CH_3$ | $CF_3$ | H | F | Br | H | isoxazolidinyl | logP = 2.63[a] |
| 29 | $CH_3$ | $CF_3$ | H | F | Br | H | N=C(thiazolidinyl)-CN | — |
| 30 | $CH_3$ | $CF_3$ | H | F | Br | H | oxazolidin-2-one-yl | logP = 2.59[a] |
| 31 | $CH_3$ | $CF_3$ | H | F | Br | H | N=C(3-methylthiazol-2-ylidene) | logP = 2.59[a] |
| 32 | $CH_3$ | $CF_3$ | H | F | Cl | H | N=C(3-methylthiazol-2-ylidene) | logP = 2.51[a] |

TABLE 1-continued

Examples of compounds of the formula (I). In all cases, Q represents oxygen.

| Ex. No. | R¹ | R² | R³ | R⁴ | R⁵ | R⁶ | R⁷ | Physical data |
|---|---|---|---|---|---|---|---|---|
| 33 | CH₃ | CF₃ | H | F | Br | H | methyl 1-methylpyrrolidine-2-carboxylate | logP = 2.52[a] |
| 34 | CH₃ | CF₃ | H | F | Cl | H | methyl 1-methylpyrrolidine-2-carboxylate | logP = 2.46[a] |
| 35 | CH₃ | CF₃ | H | F | Cl | H | (pyridin-2-yl)amino | logP = 2.88[a] |
| 36 | CH₃ | CF₃ | H | F | Br | H | ethyl 1-methylpiperidine-4-carboxylate | logP = 2.88[a] |
| 37 | CH₃ | CF₃ | H | F | Br | H | N-methyl-N-(furan-2-ylmethyl)amino | logP = 2.95[a] |
| 38 | CH₃ | CF₃ | H | F | Br | H | N-methyl-N-(1-methylethyl)aminoethyl(methyl)amino | logP = 2.79[a] |
| 39 | CH₃ | CF₃ | H | F | Br | H | (4,5-dihydrothiazol-2-yl)amino | logP = 2.16[a] |
| 40 | CH₃ | CF₃ | H | F | Br | H | 2-ethyl-5-methyl-1,3,4-thiadiazole | logP = 2.06[a] |

TABLE 1-continued

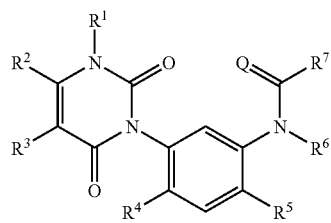

(I)

Examples of compounds of the formula (I). In all cases, Q represents oxygen.

| Ex. No. | $R^1$ | $R^2$ | $R^3$ | $R^4$ | $R^5$ | $R^6$ | $R^7$ | Physical data |
|---|---|---|---|---|---|---|---|---|
| 41 | $CH_3$ | $CF_3$ | H | F | Br | H | morpholinylmethyl | logP = 2.16[a] |
| 42 | $CH_3$ | $CF_3$ | H | F | Cl | H | ethyl 1-methylpiperidine-4-carboxylate | logP = 2.84[a] |
| 43 | $CH_3$ | $CF_3$ | H | F | Cl | H | ethyl 1-methylpiperidine-3-carboxylate | logP = 2.93[a] |
| 44 | $CH_3$ | $CF_3$ | H | F | Cl | H | N-methyl-N-(furan-2-ylmethyl)amino | logP = 2.88[a] |
| 45 | $CH_3$ | $CF_3$ | H | F | Cl | H | N-methyl-N-(2-methyl-1-methylpropyl)amino | logP = 2.58[a] |
| 46 | $CH_3$ | $CF_3$ | H | F | Cl | H | N-(2-cyanoethyl)-N-ethylamino | logP = 2.36[a] |
| 47 | $CH_3$ | $CF_3$ | H | F | Cl | H | N-(2-cyanoethyl)-N-methylamino | logP = 2.12[a] |

TABLE 1-continued

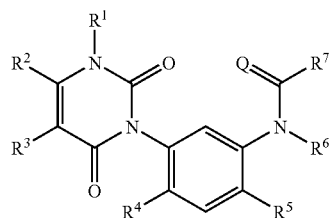

(I)

Examples of compounds of the formula (I). In all cases, Q represents oxygen.

| Ex. No. | R¹ | R² | R³ | R⁴ | R⁵ | R⁶ | R⁷ | Physical data |
|---|---|---|---|---|---|---|---|---|
| 48 | CH₃ | CF₃ | H | F | Cl | H | (N-methylamino-thiazoline) | logP = 2.11[a] |
| 49 | CH₃ | CF₃ | H | F | Cl | H | (morpholinyl-methyl) | logP = 2.11[a] |
| 50 | CH₃ | CF₃ | H | F | CN | H | (CH₃NH-O-CH₂-C(O)-O-C₂H₅) | M.p.: 130° C. |
| 51 | CH₃ | CF₃ | H | F | Cl | H | (1,3-dimethyl-imidazolidin-2-one) | logP = 2.52[a] |
| 52 | CH₃ | CF₃ | H | F | CN | H | (1,3-dimethyl-imidazolidin-2-one) | |
| 53 | CH₃ | CF₃ | H | F | Cl | H | (1-methyl-3-ethyl-imidazolidin-2-one) | logP = 2 2.81[a] |
| 54 | CH₃ | CF₃ | H | F | CN | H | (1-methyl-3-ethyl-imidazolidin-2-one) | |
| 55 | CH₃ | CF₃ | H | F | Cl | H | (CH₃O-CH(CH₃)-C(O)-O-C₂H₅) | |
| 56 | CH₃ | CF₃ | H | F | Cl | H | (1,3-dimethyl-tetrahydropyrimidin-2-one) | logP = 2.76[a] |

TABLE 1-continued

Examples of compounds of the formula (I). In all cases, Q represents oxygen.

| Ex. No. | R¹ | R² | R³ | R⁴ | R⁵ | R⁶ | R⁷ | Physical data |
|---|---|---|---|---|---|---|---|---|
| 57 | CH₃ | CF₃ | H | F | CN | H | 1,3-dimethyl-tetrahydropyrimidin-2(1H)-one-yl | |
| 58 | CH₃ | CF₃ | H | F | CN | H | N(CH₃)(OCH₃) | ¹H-NMR (DMSO-D₆, δ): 6.58 ppm |
| 59 | CH₃ | CF₃ | H | F | CN | H | isoxazolidin-2-yl | ¹H-NMR (DMSO-D₆, δ): 6.58 ppm |
| 60 | CH₃ | CF₃ | H | F | CN | H | 1-methyl-4-(methoxycarbonyl)piperidin-4-yl | ¹H-NMR (DMSO-D₆, δ): 6.58 ppm |
| 61 | CH₃ | CF₃ | H | F | CN | H | CH(C₂H₅)ON(CH₃)C(O)NH(3-Cl-C₆H₄) | ¹H-NMR (DMSO-D₆, δ): 6.55 ppm |
| 62 | CH₃ | CF₃ | H | F | Cl | H | 2-methyl-1,2-oxazinan-2-yl | logP = 2.89ᵃ⁾ |
| 63 | CH₃ | CF₃ | H | F | Br | H | 2-methyl-1,2-oxazinan-2-yl | logP = 2.96ᵃ⁾ |
| 64 | CH₃ | CF₃ | H | F | CN | H | 2-methyl-1,2-oxazinan-2-yl | |
| 65 | CH₃ | CF₃ | H | F | Cl | H | 2-methyl-5,6-dihydro-2H-1,2-oxazin-2-yl | logP = 2.78ᵃ⁾ |

TABLE 1-continued
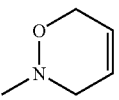
Examples of compounds of the formula (I). In all cases, Q represents oxygen.
| Ex. No. | R¹ | R² | R³ | R⁴ | R⁵ | R⁶ | R⁷ | Physical data |
|---|---|---|---|---|---|---|---|---|
| 66 | CH₃ | CF₃ | H | F | Br | H | 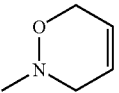 | logP = 2.85[a] |
| 67 | CH₃ | CF₃ | H | F | CN | H | 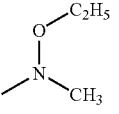 | |
| 68 | CH₃ | CF₃ | H | F | Cl | H | 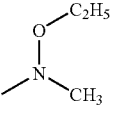 | logP = 2.99[a] |
| 69 | CH₃ | CF₃ | H | F | Br | H | 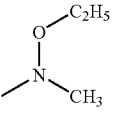 | logP = 3.06[a] |
| 70 | CH₃ | CF₃ | H | F | CN | H | 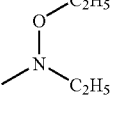 | |
| 71 | CH₃ | CF₃ | H | F | Cl | H | 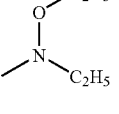 | logP = 3.35[a] |
| 72 | CH₃ | CF₃ | H | F | Br | H | 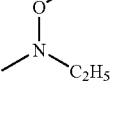 | logP = 3.41[a] |
| 73 | CH₃ | CF₃ | H | F | CN | H | | |
| 74 | CH₃ | CF₃ | H | F | Cl | H | 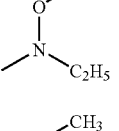 | logP = 2.93[a] |
| 75 | CH₃ | CF₃ | H | F | Br | H | 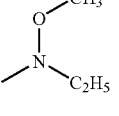 | logP = 3.01[a] |

TABLE 1-continued

Examples of compounds of the formula (I). In all cases, Q represents oxygen.

| Ex. No. | R¹ | R² | R³ | R⁴ | R⁵ | R⁶ | R⁷ | Physical data |
|---|---|---|---|---|---|---|---|---|
| 76 | CH₃ | CF₃ | H | F | CN | H | –N(CH₃)–O–CH₃ with C₂H₅ on N | |
| 77 | CH₃ | CF₃ | H | F | Cl | CH₃ | –N(CH₃)–O–CH₃ with CH₃ on N | logP = 2.53[a] |
| 78 | CH₃ | CF₃ | H | F | Br | CH₃ | –N(CH₃)–O–CH₃ with CH₃ on N | |
| 79 | CH₃ | CF₃ | H | F | CN | CH₃ | –N(CH₃)–O–CH₃ with CH₃ on N | |
| 80 | CH₃ | CF₃ | H | F | Cl | H | 1-methylpiperidin-4-yl–O–CH₃ | |
| 81 | CH₃ | CF₃ | H | F | Br | H | 1-methylpiperidin-4-yl–O–CH₃ | |
| 82 | CH₃ | CF₃ | H | F | Cl | H | –CH₂–O–(1-methylpiperidin-4-yl), methyl ester | |

TABLE 1-continued
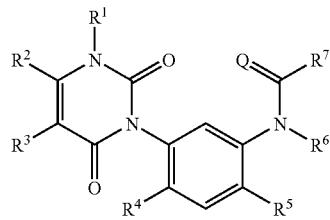
(I)
Examples of compounds of the formula (I). In all cases, Q represents oxygen.
| Ex. No. | R¹ | R² | R³ | R⁴ | R⁵ | R⁶ | R⁷ | Physical data |
|---|---|---|---|---|---|---|---|---|
| 83 | CH₃ | CF₃ | H | F | Br | H | 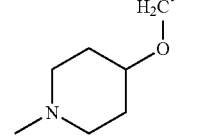 | |
| 84 | CH₃ | CF₃ | H | F | Cl | H | 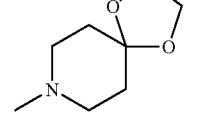 | logP = 2.29[a] |
| 85 | CH₃ | CF₃ | H | F | Br | H | 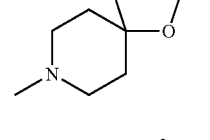 | logP = 2.35[a] |
| 86 | CH₃ | CF₃ | H | F | Cl | H | 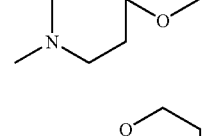 | logP = 2.29[a] |
| 87 | CH₃ | CF₃ | H | F | Br | H | 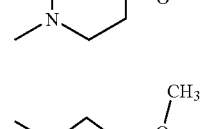 | logP = 2.35[a] |
| 88 | CH₃ | CF₃ | H | F | Cl | H | 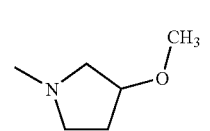 | |
| 89 | CH₃ | CF₃ | H | F | Br | H | 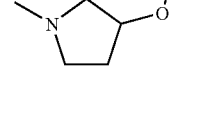 | |

TABLE 1-continued
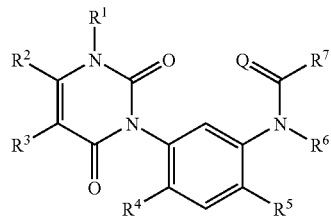
Examples of compounds of the formula (I). In all cases, Q represents oxygen.
| Ex. No. | R¹ | R² | R³ | R⁴ | R⁵ | R⁶ | R⁷ | Physical data |
|---|---|---|---|---|---|---|---|---|
| 90 | CH₃ | CF₃ | H | F | Cl | H | 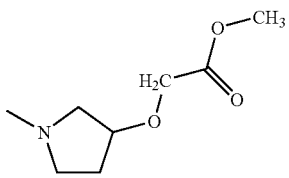 | |
| 91 | CH₃ | CF₃ | H | F | Br | H | 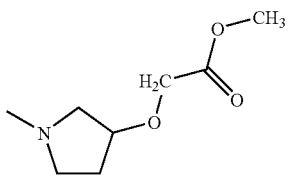 | |
| 92 | CH₃ | CF₃ | H | F | Cl | H | 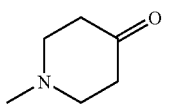 | logP = 1.93ᵃ⁾ |
| 93 | CH₃ | CF₃ | H | F | Br | H | 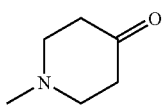 | logP = 1.97ᵃ⁾ |
| 94 | CH₃ | CF₃ | H | F | Cl | H | 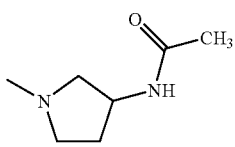 | logP = 1.74ᵃ⁾ |
| 95 | CH₃ | CF₃ | H | F | Br | H | 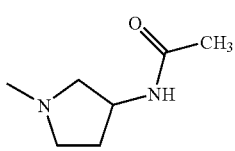 | logP = 1.80ᵃ⁾ |
| 96 | CH₃ | CF₃ | H | F | Cl | H | 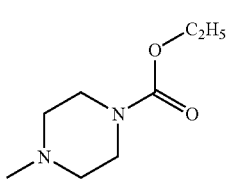 | logP = 2.43ᵃ⁾ |

TABLE 1-continued

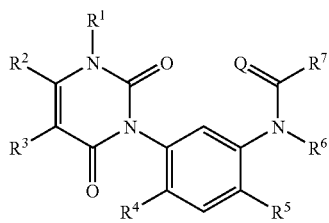

(I)

Examples of compounds of the formula (I). In all cases, Q represents oxygen.

| Ex. No. | R¹ | R² | R³ | R⁴ | R⁵ | R⁶ | R⁷ | Physical data |
|---|---|---|---|---|---|---|---|---|
| 97 | CH₃ | CF₃ | H | F | Br | H | (4-methylpiperazin-1-yl)carboxylate ethyl ester | logP = 2.47[a] |
| 98 | CH₃ | CF₃ | H | F | Cl | H | 1-methylazepan-1-yl | logP = 3.02[a] |
| 99 | CH₃ | CF₃ | H | F | Br | H | 1-methylazepan-1-yl | logP = 3.10[a] |
| 100 | CH₃ | CF₃ | H | F | Cl | H | HN(CH₃)O-C(CH₃)₂-C(O)OC₂H₅ | logP = 3.11[a] |
| 101 | CH₃ | CF₃ | H | F | Br | H | HN(CH₃)O-C(CH₃)₂-C(O)OC₂H₅ | logP = 3.16[a] |
| 102 | CH₃ | CF₃ | H | F | Cl | H | 2-methyl-1,2-thiazolidine 1,1-dioxide | logP = 2.38[a] |
| 103 | CH₃ | CF₃ | H | F | Br | H | 2-methyl-1,2-thiazolidine 1,1-dioxide | logP = 2.41[a] |
| 104 | CH₃ | CF₃ | H | F | Cl | H | CH₃NH-O-CH₂-C(O)OCH₂CH₃ | logP = 2.58[a] |
| 105 | CH₃ | CF₃ | H | F | Br | H | CH₃NH-O-CH₂-C(O)OCH₂CH₃ | logP = 2.62[a] |

TABLE 1-continued

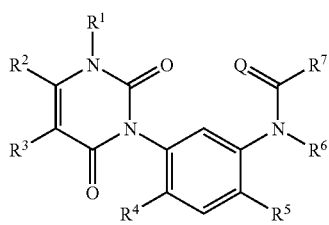

Examples of compounds of the formula (I). In all cases, Q represents oxygen.

| Ex. No. | R¹ | R² | R³ | R⁴ | R⁵ | R⁶ | R⁷ | Physical data |
|---|---|---|---|---|---|---|---|---|
| 106 | CH₃ | CF₃ | H | F | Cl | -CH₂-CH=CH-CH₂- (allyl type) | N(CH₃)-O-CH₃ | logP = 2.96$^{a)}$ |
| 107 | CH₃ | CF₃ | H | F | Cl | -CH₂C(O)OCH₃ | N(CH₃)-O-CH₃ | logP = 2.72$^{a)}$ |
| 108 | CH₃ | CF₃ | H | F | Cl | -CH₂-C≡CH | N(CH₃)-O-CH₃ | logP = 2.75$^{a)}$ |
| 109 | CH₃ | CF₃ | H | F | Cl | -S(O)₂CH₃ | N(CH₃)-O-CH₃ | logP = 2.56$^{a)}$ |
| 110 | CH₃ | CF₃ | H | F | Cl | -S(O)₂CH₂CH₃ | N(CH₃)-O-CH₃ | logP = 2.77$^{a)}$ |
| 111 | CH₃ | CF₃ | H | F | Cl | C₂H₅ | N(CH₃)-O-CH₃ | logP = 2.80$^{a)}$ |
| 112 | CH₃ | CF₃ | H | F | Br | H | 3-oxomorpholin-4-yl | logP = 2.69$^{a)}$ |
| 113 | CH₃ | CF₃ | H | F | Cl | H | 3-hydroxypyrrolidin-1-yl | logP = 1.72$^{a)}$ |
| 114 | CH₃ | CF₃ | H | F | Br | H | 3-hydroxypyrrolidin-1-yl | logP = 1.89$^{a)}$ |
| 115 | CH₃ | CF₃ | H | F | Cl | H | 3-hydroxypiperidin-1-yl | logP = 1.89$^{a)}$ |

TABLE 1-continued
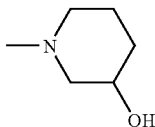
Examples of compounds of the formula (I). In all cases, Q represents oxygen.
| Ex. No. | R¹ | R² | R³ | R⁴ | R⁵ | R⁶ | R⁷ | Physical data |
|---|---|---|---|---|---|---|---|---|
| 116 | CH₃ | CF₃ | H | F | Br | H |  | logP = 1.93[a] |
| 117 | CH₃ | CF₃ | H | F | Cl | H |  | logP = 1.77[a] |
| 118 | CH₃ | CF₃ | H | F | Br | H | 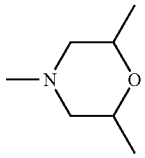 | logP = 1.81[a] |
| 119 | CH₃ | CF₃ | H | F | Cl | H | 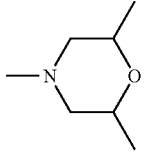 | logP = 2.50[a] |
| 120 | CH₃ | CF₃ | H | F | Br | H | 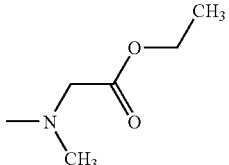 | logP = 2.55[a] |
| 121 | CH₃ | CF₃ | H | F | Cl | H | 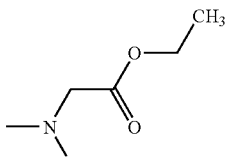 | logP = 2.48[a] |
| 122 | CH₃ | CF₃ | H | F | Br | H | 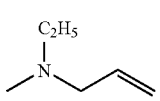 | logP = 2.54[a] |
| 123 | CH₃ | CF₃ | H | F | Br | H | C₂H₅ (N-methyl-N-allyl) | logP = 3.07[a] |

TABLE 1-continued
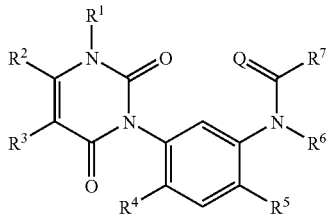
(I)
Examples of compounds of the formula (I). In all cases, Q represents oxygen.
| Ex. No. | $R^1$ | $R^2$ | $R^3$ | $R^4$ | $R^5$ | $R^6$ | $R^7$ | Physical data |
|---|---|---|---|---|---|---|---|---|
| 124 | $CH_3$ | $CF_3$ | H | F | Cl | H | 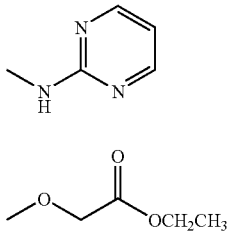 | logP = 2.56[a] |
| 125 | $CH_3$ | $CF_3$ | H | F | Br | H | 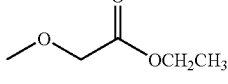 | logP = 2.79[a] |
| 126 | $CH_3$ | $CF_3$ | H | F | Cl | H | 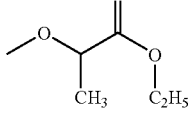 | logP = 2.74[a] |
| 127 | $CH_3$ | $CF_3$ | H | F | Cl | H | 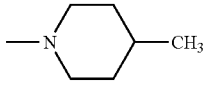 | logP = 2.74[a] |
| 128 | $CH_3$ | $CF_3$ | H | F | CN | H | 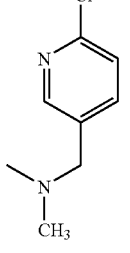 | logP = 2.80[a] |
| 129 | $CH_3$ | $CF_3$ | H | F | CN | H | 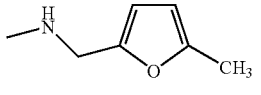 | logP = 2.50[a] |
| 130 | $CH_3$ | $CF_3$ | H | F | CN | H | $NH(CH_2)_5CN$ | logP = 2.40[a] |
| 131 | $CH_3$ | $CF_3$ | H | F | CN | H | 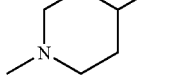 | logP = 2.80[a] |
| 132 | $CH_3$ | $CF_3$ | H | F | CN | H |  | logP = 2.88[a] |

TABLE 1-continued

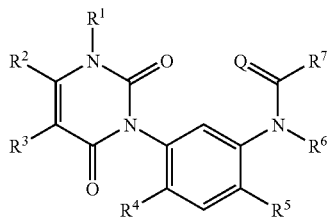

(I)

Examples of compounds of the formula (I). In all cases, Q represents oxygen.

| Ex. No. | R¹ | R² | R³ | R⁴ | R⁵ | R⁶ | R⁷ | Physical data |
|---|---|---|---|---|---|---|---|---|
| 133 | CH₃ | CF₃ | H | F | CN | H | (N-methylpiperidin-3-yl)carboxylic acid ethyl ester | logP = 2.70[a] |
| 134 | CH₃ | CF₃ | H | F | CN | H | -N(CH₃)CH₂CH₂CN | logP = 2.02[a] |
| 135 | CH₃ | CF₃ | H | F | CN | H | N(CH₂CH=CH₂)₂ | |
| 136 | CH₃ | CF₃ | H | F | CN | H | -OCH₂C(O)OC₂H₅ (methoxyacetic acid ethyl ester) | |

The logP values given in the table were determined in accordance with EEC Directive 79/831 Annex V.A8 by HPLC (High Performance Liquid Chromatography) using a reversed-phase column (C 18). Temperature: 43° C.
[a] Mobile phases for the determination in the acidic range: 0.1% aqueous phosphoric acid, acetonitrile; linear gradient from 10% acetonitrile to 90% acetonitrile - the corresponding measurement results are marked [a] in Table 1.
[b] Mobile phases for the determination in the neutral range: 0.01% molar aqueous phosphate buffer solution, acetonitrile; linear gradient from 10% acetonitrile to 90% acetonitrile - corresponding measurement results are marked [b] in Table 1.

Calibration was carried out using unbranched alkan-2-ones (with 3 to 16 carbon atoms) with known logP values (determination of the logP values by the retention times using linear interpolation between two successive alkanones).

The lambda max values were determined in the maxima of the chromatographic signals using the UV spectra from 200 nm to 400 nm.

Starting Materials of the Formula (II):

Example II-1

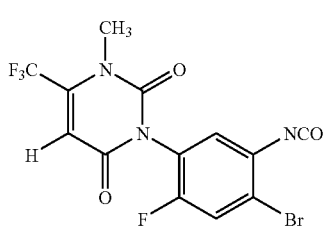

At about −20° C., 374.5 g (3.78 mol) of phosgene are initially charged in 1000 ml of chlorobenzene and, after removal of the cooling bath, a solution of 241 g (0.63 mol) of 3-(5-amino-4-bromo-2-fluorophenyl)-1-methyl-6-trifluoromethyl-1H-pyrimidine-2,4-dione in 1000 ml of chlorobenzene is added dropwise with stirring, over a period of 20 minutes, during which the internal temperature increases to about 10° C. The reaction mixture is then stirred at room temperature (about 20° C.) for about 30 minutes, then, with introduction of phosgene (about 280 g), heated to 120° C. and finally stirred at this temperature for about 60 minutes. For work-up, the volatile components are carefully distilled off under reduced pressure (about 14 mbar).

This gives 276 g (86% of theory, purity of the product 80.6%) of 3-(4-bromo-2-fluoro-5-isocyanatophenyl)-1-methyl-6-trifluoromethyl-1H-pyrimidine-2,4-dione which can be used without further purification for preparing compounds of the formula (I) according to the invention.

Example II-2

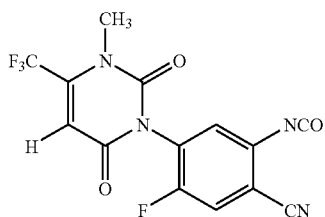

0.50 g (1.07 mmol) of 3-(5-amino-4-cyano-2-fluorophenyl)-1-methyl-6-trifluoromethyl-1H-pyrimidine-2,4-dione is initially charged in 50 ml of acetone, 0.24 g (1.23 mmol) of trichloromethyl chloroformate ("diphosgene") is added dropwise and the mixture is stirred at room temperature (about 20° C.) for 2 hours. The volatile components are then carefully distilled off under reduced pressure.

The product obtained in this manner as residue can be used without further purification for preparing compounds of the formula (I) according to the invention.

Analogously to Examples II-1 and II-2, it is also possible to prepare, for example, the compounds of the formula II listed in Table 2 below.

TABLE 2

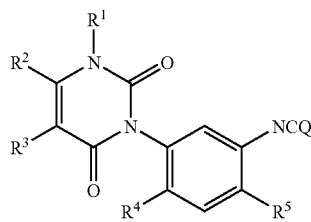

Examples of compounds of the formula (II)

| Ex. No. | Q | $R^1$ | $R^2$ | $R^3$ | $R^4$ | $R^5$ | Physical data |
|---|---|---|---|---|---|---|---|
| II-3 | O | $CH_3$ | $CF_3$ | H | F | Cl | |
| II-4 | O | $CH_3$ | $CF_3$ | H | Cl | Cl | |
| II-5 | O | $CH_3$ | $CF_3$ | H | Cl | Br | |
| II-6 | O | $CH_3$ | $CF_3$ | H | H | Cl | |
| II-7 | O | $CH_3$ | $CF_3$ | H | H | Br | |
| II-8 | O | $CH_3$ | $CF_3$ | H | H | CN | |

Use Examples:

Example A

| Pre-emergence test | |
|---|---|
| Solvent: | 5 parts by weight of acetone |
| Emulsifier: | 1 part by weight of alkylaryl polyglycol ether |

To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil. After 24 hours, the soil is sprayed with the preparation of active compound such that the particular amount of active compound desired is applied per unit area. The concentration of active compound in the spray liquor is chosen such that the particular amount of active compound desired is applied in 1000 liters of water per hectare.

After three weeks, the degree of damage to the plants is rated in % damage in comparison to the development of the untreated control. The figures denote:

0%=no effect (like untreated control)
100%=total destruction

In this test, for example, the compounds of Preparation Examples 2, 3, 4, 5, 6, 7, 8, 9, 10, 20, 21, 22, 24, 25, 26, 27, 28, 30, 31, 32, 37, 38, 39, 44, 45, 46, 47, 48 and 49 exhibit strong activity against weeds, and some are tolerated well by crop plants, such as, for example, maize, wheat, soya bean and sugar beet.

Example B

| Post-emergence test | |
|---|---|
| Solvent: | 5 parts by weight of acetone |
| Emulsifier: | 1 part by weight of alkylaryl polyglycol ether |

To produce a suitable preparation of active compound, 1 part by weight of active compound is mixed with the stated amount of solvent, the stated amount of emulsifier is added and the concentrate is diluted with water to the desired concentration.

Test plants of a height of 5-15 cm are sprayed with the preparation of active compound such that the particular amounts of active compound desired are applied per unit area. The concentration of the spray liquor is chosen such that the particular amounts of active compound desired are applied in 1000 l of water/ha.

After three weeks, the degree of damage to the plants is rated in % damage in comparison to the development of the untreated control.

The figures denote:

0%=no effect (like untreated control)
100%=total destruction

In this test, for example, the compounds of Preparation Examples 2, 3, 4, 5, 6, 7, 8, 9, 10, 21, 24, 25, 26, 27, 28, 30, 31, 32, 33, 34, 35, 36, 37, 38, 39, 40, 41, 42, 44, 45, 46, 47 and 48 exhibit strong activity against weeds, and some are tolerated well by crop plants, such as, for example, wheat.

The invention is claimed is:

1. A compound of formula (I)

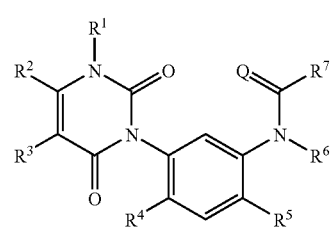

in which

Q represents oxygen, $R^1$ represents hydrogen or amino; or represents optionally cyano-, halogen-, or $C_1$-$C_4$-alkoxy-substituted alkyl having 1 to 6 carbon atoms, $R^2$ represents carboxyl, cyano, carbamoyl, or thiocarbamoyl; or represents optionally cyano-, halogen-, or $C_1$-$C_4$- alkoxy-substituted alkyl or alkoxy-carbonyl having in each case 1 to 6 carbon atoms in the alkyl groups, $R^3$ represents hydrogen or halogen; or represents optionally halogen-substituted alkyl having 1 to 6 carbon atoms, $R^4$ represents hydrogen, cyano, carbamoyl, thiocarbamoyl, or halogen, $R^5$ represents cyano, carbamoyl, thiocarbamoyl, or halogen; or represents optionally halogen-substituted alkyl or alkoxy having in each case 1 to 6 carbon atoms, $R^6$ represents hydrogen; represents optionally cyano-, carboxyl-, halogen-, $C_1$-$C_4$-alkoxy-, $C_1$-$C_4$-alkylthio-, $C_1$-$C_4$-alkylsulphinyl-, $C_1$-$C_4$-alkylsulphonyl-, $C_1$-$C_4$-alkyl-carbonyl-, or $C_1$-$C_4$-alkoxy-carbonyl-substituted alkyl having 1 to 6 carbon atoms; represents optionally cyano-, halogen-, or $C_1$-$C_4$-alkoxy-substituted alkylcarbonyl, alkoxycarbonyl, or alkylsulphonyl having in each case 1 to 6 carbon atoms in the alkyl groups; represents optionally halogen-substituted alkenyl, alkenylcarbonyl, alkenylsulphonyl, or alkynyl having in each case 3 to 6 carbon atoms in the alkenyl or alkynyl groups; represents optionally cyano-, halogen-, or $C_1$-$C_4$-alkyl-substituted cycloalkyl, cycloalkylalkyl, cycloalkylcarbonyl, cycloalkylalkylcarbonyl, cycloalkylsulphonyl, or cycloalkylalkylsulphonyl having in each case 3 to 6 carbon atoms in the cycloalkyl groups and optionally 1 to 4 carbon atoms in the alkyl moiety; represents optionally nitro-, cyano-, halogen-, $C_1$-$C_4$-alkyl-, $C_1$-$C_4$-haloalkyl-, $C_1$-$C_4$-alkoxy-, $C_1$-$C_4$-haloalkoxy-, or $C_1$-$C_4$-alkoxy-carbonyl-substituted aryl, arylalkyl, arylcarbonyl, arylalkylcarbonyl, arylsulfonyl, or arylalkylsulphonyl having in each case 6 or 10 carbon atoms in the aryl groups and optionally 1 to 4 carbon atoms in the alkyl moiety; or represents optionally nitro-, cyano-, halogen-, $C_1$-$C_4$-alkyl-, $C_1$-$C_4$-haloalkyl-, $C_1$-$C_4$-alkoxy-, $C_1$-$C_4$-haloalkoxy-, or $C_1$-$C_4$-alkoxy-carbonyl-substituted heterocyclylcarbonyl, heterocyclylalkylcarbonyl, heterocyclylsulphonyl, or heterocyclylalkylsulphonyl having in each case up to 6 carbon atoms, up to 5 nitrogen atoms, and/or 1 or 2 oxygen or sulphur atoms as ring members, wherein each heterocyclyl group also optionally contains 1 or 2 —SO groups, 1 or 2 —$SO_2$ groups, 1 or 2 —CO groups, or 1 or 2 —CS groups, and $R^7$ represents optionally halogen-substituted alkoxycarbonylalkoxy, alkoxycarbonylalkylthio, alkenyloxycarbonylalkoxy, alkenyloxycarbonylalkylthio, alkynyloxycarbonylalkoxy, alkynyloxycarbonylalkylthio, carbamoylalkoxy, carbamoylalkylthio, alkylaminocarbonylalkoxy, alkylaminocarbonylalkylthio, dialkylaminocarbonylalkoxy, dialkylaminocarbonylalkylthio, N-alkyl-N-alkenylaminocarbonylalkoxy, N-alkyl-N-alkenylaminocarbonylalkylthio, dialkenylaminocarbonylalkoxy, dialkenylaminocarbonylalkylthio, N-alkyl-N-alkynylaminocarbonylalkoxy, N-alkyl-N-alkynylaminocarbonylalkylthio having in each case up to 6 carbon atoms in the alkyl, alkenyl, or alkynyl groups; represents hydroxyamino; represents optionally halogen-substituted N-alkylhydroxyamino, alkoxyamino, N-alkylalkoxyamino, alkoxycarbonylalkoxyamino, or N-alkylalkoxycarbonylalkoxyamino having in each case 1 to 6 carbon atoms in the alkyl groups; represents optionally halogen-substituted alkenyloxyamino, N-alkylalkenyloxyamino, N-alkenylalkoxyamino, or N-alkenylalkenyloxyamino having in each case 3 to 6 carbon atoms in the alkenyl groups and optionally 1 to 6 carbon atoms in the alkyl groups; represents cycloalkyloxyamino or N-alkylcycloalkyloxyamino having in each case 3 to 6 carbon atoms in the cycloalkyl groups and optionally 1 to 6 carbon atoms in the alkyl group; represents optionally halogen-substituted aryloxyamino or N-alkylaryloxyamino having in each case 6 or 10 carbon atoms in the aryl groups and optionally 1 to 6 carbon atoms in the alkyl group; represents cyanoalkylamino having 1 to 6 carbon atoms; represents optionally cyano-, halogen-, $C_1$-$C_4$-alkoxy-, or $C_1$-$C_4$-alkoxycarbonyl-substituted dialkylamino having in each case 1 to 6 carbon atoms in the alkyl groups; represents optionally cyano-, halogen-, or $C_1$-$C_4$-alkoxy-carbonyl-substituted N-alkyl-N-alkenylamino or N-alkyl-N-alkynylamino having in each case up to 6 carbon atoms in the alkyl, alkenyl, or alkynyl groups; represents dialkenylamino or dialkynylamino having in each case up to 6 carbon atoms in the alkenyl or alkynyl groups; optionally nitro-, cyano-, halogen-, $C_1$-$C_4$-alkyl-, $C_1$-$C_4$-haloalkyl-, $C_1$-$C_4$-alkoxy-, $C_1$-$C_4$-haloalkoxy-, $C_1$-$C_4$-alkylthio-, $C_1$-$C_4$-haloalkylthio-, $C_1$-$C_4$-alkoxy-carbonyl-, $C_3$-$C_6$-cycloalkyl-, or monocyclic or bicyclic phenyl-substituted heterocyclyloxy, heterocyclylthio, heterocyclylamino, N-alkylheterocyclylamino, N-alkylheterocyclylalkylamino, or —N= (heterocyclyl), where the heterocyclyl group contains up to 6 carbon atoms, up to 5 nitrogen atoms and/or 1 or 2 oxygen atoms and/or 1 or 2 sulphur atoms and optionally additionally 1 or 2 —SO groups and/or 1 or 2 —$SO_2$ groups and/or 1 or 2 —CO groups and/or 1 or 2 —CS groups, and the alkyl group optionally contains 1 to 6 carbon atoms; a monocyclic or bicyclic nitrogen heterocycle that is attached via N, contains up to 9 carbon atoms, up to 5 nitrogen atoms, and optionally additionally 1 or 2 oxygen or sulphur atoms and optionally additionally 1 or 2 —SO groups, 1 or 2 —$SO_2$ groups, 1 or 2 —CO groups, 1 or 2 —CS groups, or one cyanoimino group (C=N—CN) and is optionally substituted by nitro, cyano, halogen, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, $C_1$-$C_4$-alkoxy-carbonyl, $C_1$-$C_4$-alkoxy-carbonyl-$C_1$-$C_2$-alkoxy, $C_1$-$C_4$-alkylcarbonylamino, $C_1$-$C_4$-alkoxy-carbonylamino, $C_2$-$C_4$-alkylenedioxy, $C_3$-$C_6$-cycloalkyl, or phenyl.

2. A compound of formula (I) according to claim 1 in which Q represents oxygen, $R^1$ represents hydrogen or amino; or represents optionally cyano-, fluorine-, chlorine-, bromine-, methoxy-, ethoxy-, or n- or i-propoxy-substituted alkyl having 1 to 5 carbon atoms, $R^2$ represents carboxyl, cyano, carbamoyl, or thiocarbamoyl; or represents optionally cyano-, fluorine-, chlorine-, bromine-, methoxy-, ethoxy-, or n- or i-propoxy-substituted alkyl or alkoxycarbonyl having in each case 1 to 5 carbon atoms in the alkyl groups, $R^3$ represents hydrogen, fluorine, chlorine, or bromine; or represents optionally fluorine-, chlorine-, or bromine-substituted alkyl having 1 to 5 carbon atoms, $R^4$ represents hydrogen, cyano, carbamoyl, thiocarbamoyl, fluorine, chlorine, or bromine, $R^5$ represents cyano, carbamoyl, thiocarbamoyl, fluorine, chlorine, or bromine; or represents optionally fluorine-, chlorine-, or bromine-substituted alkyl or alkoxy having in each case 1 to 5 carbon atoms, $R^6$ represents hydrogen; represents optionally cyano-, carboxyl-, fluorine-, chlorine-, bromine-, methoxy-, ethoxy-, n- or i-propoxy-, methylthio-, ethylthio-, n- or i-propylthio-, methylsulphinyl-, ethylsulphinyl-, n- or i-propylsulphinyl-, methylsulphonyl-, ethylsulphonyl-, acetyl-, propionyl-, n- or i-butyroyl-, methoxycarbonyl-, ethoxycarbonyl-, or n- or -propoxycarbonyl-substituted alkyl having 1 to 5 carbon atoms; represents optionally cyano-, fluorine-, chlorine-, bromine-, methoxy-, ethoxy-, or n- or i-propoxy-substituted alkylcarbonyl, alkoxycarbonyl, or alkylsulphonyl having in each case 1 to 5 carbon atoms in the alkyl groups; represents optionally fluorine-, chlorine-, or bromine-substituted alkenyl, alkenylcarbonyl, alkenylsulphonyl, or alkynyl having in each case 3 to 5 carbon atoms in the alkenyl or alkynyl groups; represents optionally cyano-, fluorine-, chlorine-, bromine-, methyl-, ethyl-, or n- or i-propyl-substituted cycloalkyl, cycloalkylalkyl, cycloalkylcarbonyl, cycloalkylalkylcarbonyl, cycloalkylsulphonyl, or cycloalkylalkylsulphonyl having in each case 3 to 6 carbon atoms in the cycloalkyl groups and optionally 1 to 3 carbon atoms in the alkyl moiety; represents optionally nitro-, cyano-, fluorine-, chlorine-, bromine-, methyl-, ethyl-, n- or i-propyl-, n-, i-, s-, or t-butyl-, trifluoromethyl-, chlorodifluoromethyl-, fluorodichloromethyl-, methoxy-, ethoxy-, n- or i-propoxy-, n-, i-, s-, or t-butoxy-, difluoromethoxy-, trifluoromethoxy-, chlorodifluoromethoxy-, fluorodichloromethoxy-, methoxycarbonyl-, ethoxycarbonyl-, n- or 1-propoxycarbonyl-, or n-, i-, s-, or t-butoxycarbonyl-substituted aryl, arylalkyl, arylcarbonyl, arylalkylcarbonyl, arylsulphonyl, or arylalkylsulphonyl having in each case 6 or 10 carbon atoms in the aryl groups and optionally 1 to 3 carbon atoms in the alkyl moiety; or represents optionally nitro-, cyano-, fluorine-, chlorine-, bromine-, methyl-, ethyl-, n- or i-propyl-, n-, i-, s-, or t-butyl-, trifluoromethyl-, chlorodifluoromethyl-, fluorodichloromethyl-, methoxy-, ethoxy-, n- or i-propoxy-, n-, i-, s-, or t-butoxy-, difluoromethoxy-, trifluoromethoxy-, chlorodifluoromethoxy-, fluorodichloromethoxy-, methoxycarbonyl-, ethoxycarbonyl-, n- or -propoxycarbonyl-, or n-, i-, s-, or t-butoxycarbonyl-substituted heterocyclylcarbonyl, heterocyclylalkylcarbonyl, heterocyclylsulphonyl, or heterocyclylalkylsulphonyl having in each case up to 5 carbon atoms, up to 4 nitrogen atoms, and/or one oxygen or sulphur atom as ring members, wherein each heterocyclyl group also optionally contains an —SO group, an —SO$_2$ group, 1 or 2 —CO groups, or 1 or 2 —CS groups, and $R^7$ represents optionally halogen-substituted alkoxycarbonylalkoxy, alkoxycarbonylalkylthio, alkenyloxycarbonylalkoxy, alkenyloxycarbonylalkylthio, alkynyloxycarbonylalkoxy, alkynyloxycarbonylalkylthio, carbamoylalkoxy, carbamoylalkylthio, alkylaminocarbonylalkoxy, alkylaminocarbonylalkylthio, dialkylaminocarbonylalkoxy, dialkylaminocarbonylalkylthio, dialkenylaminocarbonylalkoxy, dialkenylaminocarbonylalkylthio, dialkynylaminocarbonyloxy, or dialkynylaminocarbonylalkylthio having in each case up to 5 carbon atoms in the alkyl, alkenyl, or alkynyl groups; hydroxyamino; represents optionally halogen-substituted N-alkylhydroxyamino, alkoxyamino, N-alkylalkoxyamino, alkoxycarbonylalkoxyamino, or N-alkylalkoxycarbonylalkoxyamino having in each case 1 to 5 carbon atoms in the alkyl groups; represents optionally halogen-substituted alkenyloxyamino, N-alkyl-alkenyloxyamino, N-alkenylalkoxyamino or N-alkenylalkenyloxyamino having in each case 3 to 5 carbon atoms in the alkenyl groups and optionally 1 to 5 carbon atoms in the alkyl groups; represents cycloalkyloxyamino or N-alkylcycloalkyloxyamino having in each case 3 to 6 carbon atoms in the cycloalkyl groups and optionally 1 to 3 carbon atoms in the alkyl group; represents optionally halogen-substituted aryloxyamino or N-alkylaryloxyamino having in each case 6 or 10 carbon atoms in the aryl groups and optionally 1 to 3 carbon atoms in the alkyl group; represents cyanoalkylamino having 1 to 5 carbon atoms; represents optionally cyano-, fluorine-, chlorine-, methoxy-, ethoxy-, n- or i-propoxy-, methoxycarbonyl-, ethoxycarbonyl-, or n- or i-propoxycarbonyl-substituted dialkylamino having in each case 1 to 5 carbon atoms in the alkyl groups; represents optionally cyano-, fluorine-, chlorine-, methoxy-, ethoxy-, n- or i-propoxy-, methoxycarbonyl-, ethoxycarbonyl-, or n- or i-propoxycarbonyl-substituted N-alkyl-N-alkenylamino or N-alkyl-N-alkynylamino having in each case up to 5 carbon atoms in the alkyl, alkenyl, or alkynyl groups; represents dialkenylamino or dialkynylamino having in each case up to 5 carbon atoms in the alkenyl or alkynyl groups; represents optionally nitro-, cyano-, fluorine-, chlorine-, bromine-, methyl-, ethyl-, n- or i-propyl-, n-, i-, s-, or t-butyl-, difluoromethyl-, dichloromethyl-, trifluoromethyl-, chlorodifluoromethyl-, fluorodichloromethyl-, methoxy-, ethoxy-, n- or 1-propoxy-, n-, i-, s-, or t-butoxy-, difluoromethoxy-, trifluoromethoxy-, chlorodifluoromethoxy-, methylthio-, ethylthio-, n- or i-propylthio-, n-, i-, s- or t-butylthio-, difluoromethylthio-, trifluoromethylthio-, chlorodifluoromethylthio-, methoxycarbonyl-, ethoxycarbonyl-, n- or i-propoxycarbonyl-, n-, i-, s-, or t-butoxycarbonyl-, cyclopropyl-, cyclobutyl-, cyclopentyl-, cyclohexyl-, or phenyl-substituted heterocyclyloxy, heterocyclylthio, heterocyclylamino, N-alkylheterocyclylamino, N-alkylheterocyclylalkylamino, or —N=(heterocyclyl), where the monocyclic or bicyclic heterocyclyl group contains up to 6 carbon atoms, up to 5 nitrogen atoms, and/or 1 or 2 oxygen atoms and/or 1 or 2 sulphur atoms and optionally additionally 1 or 2 —SO groups and/or 1 or 2 —SO$_2$ groups and/or 1 or 2 —CO groups and/or 1 or 2 —CS groups and the alkyl group optionally contains 1 to 3 carbon atoms; represents a monocyclic or bicyclic nitrogen heterocycle that is attached via N, contains up to 9 carbon atoms, up to 5 nitrogen atoms, and optionally additionally 1 or 2 oxygen or sulphur atoms and optionally additionally 1 or 2 —SO groups, 1 or 2 —SO$_2$ groups, 1 or 2 —CO groups, 1 or 2 —CS groups or one cyanoimino group (C=N—CN) and is optionally substituted by nitro, cyano, fluorine, chlorine, bromine, methyl, ethyl, n- or i-propyl, n-, 1-, s-, or t-butyl, difluoromethyl, dichloromethyl, trifluoromethyl, chlorodifluoromethyl, fluorodichloromethyl, methoxy, ethoxy, n- or i-propoxy, n-, i-, s-, or t-butoxy, difluoromethoxy, trifluoromethoxy, chlorodifluoromethoxy, methylthio, ethylthio, n- or i-propylthio, n-, i-, s-, or t-butylthio, difluoromethylthio, trifluoromethylthio, chlorodifluoromethylthio, methoxycarbonyl, ethoxycarbonyl, n- or i-propoxycarbonyl, n-, i-, s-, or t-butoxycarbonyl, methoxycarbonylmethoxy, ethoxycarbonylmethoxy, acetylamino, propionylamino, methoxycarbonylamino, ethoxycarbonylamino, ethylenedioxy, propylenedioxy, cyclopropyl, cyclobutyl, cyclopentyl, cyclohexyl, or phenyl.

3. A compound of formula (I) according to claim 1 in which $R^1$ represents hydrogen or amino; or represents optionally cyano-, fluorine-, chlorine-, bromine-, methoxy-, ethoxy-, or n- or i-propoxy-substituted methyl, ethyl, n- or i-propyl, or n-, i-, or s-butyl, R² represents carboxyl, cyano, carbamoyl, or thiocarbamoyl; or represents optionally cyano-, fluorine-, chlorine-, bromine-, methoxy-, ethoxy-, or n- or i-propoxy-substituted methyl, ethyl, n- or i-propyl, methoxycarbonyl, ethoxycarbonyl, or n- or i-propoxycarbonyl, R³ represents hydrogen, fluorine, chlorine, or bromine; or represents optionally fluorine-, chlorine-, or bromine-substituted methyl, ethyl, or n- or i-propyl, R⁴ represents hydrogen, cyano, carbamoyl, thiocarbamoyl, fluorine, chlorine, or bromine, R⁵ represents cyano, carbamoyl, thiocarbamoyl, fluorine, chlorine, or bromine; or represents optionally fluorine-, chlorine-, or bromine-substituted methyl, ethyl, n- or i-propyl, methoxy, ethoxy, or n- or -propoxy, R⁶ represents hydrogen; represents optionally cyano-, carboxyl-, fluorine-, chlorine-, bromine-, methoxy-, ethoxy-, n- or i-propoxy-, methylthio-, ethylthio-, n- or i-propylthio-, methylsulphinyl-, ethylsulphinyl-, n- or i-propylsulphinyl-, methylsulphonyl-, ethylsulphonyl-, acetyl-, propionyl-, n- or i-butyroyl-, methoxycarbonyl-, ethoxycarbonyl-, or n- or i-propoxycarbonyl-substituted methyl, ethyl, n- or i-propyl, or n-, i-, or s-butyl; represents optionally cyano-, fluorine-, chlorine-, bromine-, methoxy-, ethoxy-, or n- or i-propoxy-substituted acetyl, propionyl, n- or i-butyroyl, methoxycarbonyl, ethoxycarbonyl, n- or i-propoxycarbonyl, n-, i-, s-, or t-butoxycarbonyl, methylsulphonyl, ethylsulphonyl, n- or i-propylsulphonyl, or n-, i-, or s-butylsulphonyl; represents optionally fluorine-, chlorine-, or bromine-substituted propenyl, butenyl, propenylsulphonyl, butenylsulphonyl, propynyl, or butynyl; represents optionally cyano-, fluorine-, chlorine-, bromine-, methyl-, or ethyl-substituted cyclopropyl, cyclobutyl, cyclopentyl, cyclohexyl, cyclopropylmethyl, cyclobutylmethyl, cyclopentylmethyl, cyclohexylmethyl, cyclopropylcarbonyl, cyclobutylcarbonyl, cyclopentylcarbonyl, cyclohexylcarbonyl, cyclopropylmethylcarbonyl, cyclobutylmethylcarbonyl, cyclopentylmethylcarbonyl, cyclohexylmethylcarbonyl, cyclopropylsulphonyl, cyclobutylsulphonyl, cyclopentylsulphonyl, cyclohexylsulphonyl, cyclopropylmethylsulphonyl, cyclobutylmethylsulphonyl, cyclopentylmethylsulphonyl, or cyclohexylmethylsulphonyl; represents optionally nitro-, cyano-, fluorine-, chlorine-, bromine-, methyl-, ethyl-, n- or i-propyl-, n-, i-, s-, or t-butyl-, trifluoromethyl-, chlorodifluoromethyl-, fluorodichloromethyl-, methoxy-, ethoxy-, n- or i-propoxy-, n-, 1-, s-, or t-butoxy-, difluoromethoxy-, trifluoromethoxy-, chlorodifluoromethoxy-, fluorodichloromethoxy-, methoxycarbonyl-, ethoxycarbonyl-, n- or i-propoxycarbonyl-, or n-, i-, s-, or t-butoxycarbonyl-substituted phenyl, phenylmethyl, phenylethyl, phenylpropyl, benzoyl, phenylacetyl, phenylsulphonyl, or phenylmethylsulphonyl; or represents optionally nitro-, cyano-, fluorine-, chlorine-, bromine-, methyl-, ethyl-, n- or i-propyl-, n-, i-, s-, or t-butyl-, trifluoromethyl-, chlorodifluoromethyl-, fluorodichloromethyl-, methoxy-, ethoxy-, n- or i-propoxy-, n-, i-, s-, or t-butoxy-, difluoromethoxy-, trifluoromethoxy-, chlorodifluoromethoxy-, fluorodichloromethoxy-, methoxycarbonyl-, ethoxycarbonyl-, n- or i-propoxycarbonyl-, or n-, i-, s-, or t-butoxycarbonyl-substituted heterocyclylcarbonyl, heterocyclylmethylcarbonyl, heterocyclylsulphonyl, or heterocyclylmethylsulphonyl, where the heterocyclyl is selected from the group consisting of furyl, tetrahydrofuryl, thienyl, pyrrolyl, pyrrolinyl, pyrrolidinyl, oxopyrrolidinyl, pyrrolyl, pyrazolyl, oxazolyl, oxazolinyl, oxazolidinyl, isoxazolyl, thiazolyl, thiazolinyl, thiazolidinyl, cyanoiminothiazolidinyl, imidazolyl, imidazolinyl, 2-oxo-1,3-diaza-cyclopentyl (2-oxoimidazolidinyl), triazolyl, oxotriazolinyl, thioxotriazolinyl, pyridinyl, piperidinyl, oxopiperidinyl, 2-oxo-1,3-diazacyclohexyl, morpholinyl, and piperazinyl, and R⁷ represents methoxycarbonylmethoxy, ethoxycarbonylmethoxy, n- or i-propoxycarbonylmethoxy, n-, i-, s-, or t-butoxycarbonylmethoxy, methoxycarbonylethoxy, ethoxycarbonylethoxy, n- or i-propoxycarbonylethoxy, n-, i-, s-, or t-butoxycarbonylethoxy, methoxycarbonylmethylthio, ethoxycarbonylmethylthio, n- or i-propoxycarbonylmethylthio, n-, s-, or t-butoxycarbonylmethylthio, methoxycarbonylethylthio, ethoxycarbonylethylthio, n- or i-propoxycarbonylethylthio, n-, i-, s- or t-butoxycarbonylethylthio, propenyloxycarbonylmethoxy, butenyloxycarbonylmethoxy, propenyloxycarbonylethoxy, butenyloxycarbonylethoxy, propenyloxycarbonylmethylthio, butenyloxycarbonylmethylthio, propenyloxycarbonylethylthio, butenyloxycarbonylethylthio, propynyloxycarbonylmethoxy, butynyloxycarbonylmethoxy, propynyloxycarbonylethoxy, butynyloxycarbonylethoxy, propynyloxycarbonylmethylthio, butynyloxycarbonylmethylthio, propynyloxycarbonylethylthio, butynyloxycarbonylethylthio, carbamoylmethoxy, carbamoylethoxy, carbamoylmethylthio, carbamoylethylthio, methylaminocarbonyl methoxy, ethylaminocarbonylethoxy, n- or i-propylaminocarbonylmethoxy, n-, i-, s-, or t-butylaminocarbonylmethoxy, methylaminocarbonylethoxy, ethylaminocarbonylethoxy, n- or i-propylaminocarbonylethoxy, n-, i-, s-, or t-butylaminocarbonylethoxy, methylaminocarbonylmethylthio, ethylaminocarbonylmethylthio, n- or i-propylaminocarbonylmethylthio, n-, i-, s-, or t-butylaminocarbonylmethylthio, methylaminocarbonylethylthio, ethylaminocarbonylethylthio, n- or i-propylaminocarbonylethylthio, n-, i-, s-, or t-butylaminocarbonylethylthio, dimethylaminocarbonylmethoxy, diethylaminocarbonylmethoxy, dimethylaminocarbonylethoxy, diethylaminocarbonylethoxy, dimethylaminocarbonylmethylthio, diethylaminocarbonylmethylthio, dimethylaminocarbonylethylthio, diethylaminocarbonylethylthio, dipropenylaminocarbonylmethoxy, dipropenylaminocarbonylethoxy, dipropenylaminocarbonylmethylthio, dipropenylaminocarbonylethylthio, dipropynylaminocarbonylmethoxy, dipropynylaminocarbonylethoxy, dipropynylaminocarbonylmethylthio, or dipropynylaminocarbonylethylthio; represents hydroxyamino; represents N-methylhydroxyamino, N-ethylhydroxyamino, N-n-propylhydroxyamino, N-i-propylhydroxyamino, methoxyamino, ethoxyamino, n- or i-propoxyamino, n-, i-, s- or t-butoxyamino, N-methylmethoxyamino, N-ethylmethoxyamino, N-methylethoxyamino, methoxycarbonylmethoxyamino, ethoxycarbonylmethoxyamino, n- or i-propoxycarbonylmethoxyamino, methoxycarbonylethoxyamino, ethoxycarbonylethoxyamino, n- or i-propoxycarbonylethoxyamino, N-methylmethoxycarbonylmethoxyamino, N-methylethoxycarbonylmethoxyamino, N-methyl-n-propoxycarbonylmethoxyamino, N-methyl-i-propoxycarbonylmethoxyamino, N-methylmethoxycarbonylethoxyamino, N-methylethoxycarbonylethoxyamino, N-methyl-n-propoxycarbonylethoxyamino, N-methyl-i-propoxycarbonylethoxyamino, propenyloxyamino, butenyloxyamino, N-methylpropenyloxyamino, N-methylbutenyloxyamino, N-propenyl-methoxyamino, N-propenylethoxyamino, N-propenyl-n-propoxyamino, N-propenyl-i-propoxyamino, N-propenylpropenyloxyamino, represents cyclopentyloxyamino, cyclohexyloxyamino, N-methylcyclopentyloxyamino, or N-methylcyclohexyloxyamino; represents phenoxyamino or N-methylphenoxyamino; represents cyanomethylamino, cyanoethylamino, cyanopropylamino, or cyanobutylamino; represents optionally cyano-, fluorine-, chlorine-, methoxy-, ethoxy-, n- or -propoxy-, methoxycarbonyl-, ethoxycarbonyl, or n- or i-propoxycarbonyl-substituted dimethylamino, diethylamino, dipropylamino, or dibutylamino; represents optionally cyano-, fluorine-, chlorine-, methoxy-, ethoxy-, n- or i-propoxy-, methoxycarbonyl-, ethoxycarbonyl-, or n- or i-propoxycarbonyl-substituted N-methyl-N-propenylamino, N-methyl-N-butenylamino, N-ethyl-N-propenylamino, N-ethyl-N-butenylamino, N-propyl-N-propenylamino, N-propyl-N-butenylamino, N-butyl-N-propenylamino, N-butyl-N-butenylamino, N-methyl-N-propynylamino, N-methyl-N-butynylamino, N-ethyl-N-propynylamino, N-ethyl-N-butynylamino, N-propyl-N-propynylamino, N-propyl-N-butynylamino, N-butyl-N-propynylamino, or N-butyl-N-butynylamino; represents dipropenylamino, dibutenylamino, dipropynylamino, or dibutynylamino; represents optionally nitro-, cyano-, fluorine-, chlorine-, bromine-, methyl-, ethyl-, n- or i-propyl-, n-, i-, s-, or t-butyl-, difluoromethyl-, dichloromethyl-, trifluoromethyl-, chlorodifluoromethyl-, fluorodichloromethyl-, methoxy-, ethoxy-, n- or i-propoxy-, n-, i-, s-, or t-butoxy-, difluoromethoxy-, trifluoromethoxy-, chlorodifluoromethoxy-, methylthio-, ethylthio-, n- or i-propylthio-, n-, i-, s-, or t-butylthio-, difluoromethylthio-, trifluoromethylthio-, chlorodifluoromethylthio-, methoxycarbonyl-, ethoxycarbonyl-, n- or i-propoxycarbonyl-, n-, i-, s-, or t-butoxycarbonyl-, methoxycarbonylmethoxy-, acetylamino-, ethylenedioxy-, propylenedioxy-, cyclopropyl-, cyclobutyl-, cyclopentyl-, cyclohexyl-, or phenyl-substituted heterocyclyloxy, heterocyclylthio, heterocyclylamino, N-methylheterocyclylamino, N-ethylheterocyclylamino, N-methylheterocyclylmethylamino, N-ethylheterocyclylmethylamino, or —N=(heterocyclyl), where the heterocyclyl is selected from the group consisting of furyl, tetrahydrofuryl, thienyl, pyrrolyl, pyrrolinyl, pyrrolidinyl, oxopyrrolidinyl, pyrrolyl, pyrazolyl, oxazolyl, oxazolinyl, oxazolidinyl, isoxazolyl, thiazolyl, thiazolinyl, thiazolidinyl, cyanoiminothiazolidinyl, imidazolyl, imidazolinyl, 2-oxo-1,3-diazacyclopentyl (2-oxoimidazolidinyl), triazolyl, oxotriazolinyl, thioxotriazolinyl, pyridinyl, piperidinyl, oxopiperidinyl, 2-oxo-1,3-diazacyclohexyl, morpholinyl, piperazinyl, and pyrimidinyl; or represents a monocyclic or bicyclic nitrogen heterocycle selected from the group consisting of pyrrolyl, pyrrolinyl, pyrrolidinyl, oxopyrrolidinyl, pyrazolyl, imidazolyl, imidazolinyl, 2-oxo-1,3-diazacyclopentyl (2-oxo-imidazolidinyl), 2-oxooxazolidinyl, isoxazolidinyl, thiazolinyl, 2-oxothiazolidinyl, isothiazolidinyl, 1-oxoisothiazolidinyl, 1,1-dioxoisothiazolidinyl, 2-cyanoiminothiazolidinyl, triazolyl, oxotriazolinyl, thioxotriazolinyl, pyridinyl, piperidinyl, oxopiperidinyl, 1,2-oxaza-cyclohexyl, 1,2-oxazacyclohexenyl, 2-oxo-1,3-diazacyclohexyl, morpholinyl, and piperazinyl, each of which is attached via N and is optionally substituted by nitro, cyano, fluorine, chlorine, bromine, methyl, ethyl, n- or i-propyl, n-, i-, s-, or t-butyl, difluoromethyl, dichloromethyl, trifluoromethyl, chlorodifluoromethyl, fluorodichloromethyl, methoxy, ethoxy, n- or i-propoxy, n-, i-, s-, or t-butoxy, difluoromethoxy, trifluoromethoxy, chlorodifluoromethoxy, methylthio, ethylthio, n- or i-propylthio, n-, i-, s-, or t-butylthio, difluoromethylthio, trifluoromethylthio, chlorodifluoromethylthio, methoxycarbonyl, ethoxycarbonyl, n- or i-propoxycarbonyl, n-, i-, s-, or t-butoxycarbonyl, cyclopropyl, cyclobutyl, cyclopentyl, cyclohexyl, or phenyl.

4. A compound of formula (I) according to claim 1 in which
$R^1$ represents hydrogen or amino; or represents optionally cyano-, fluorine-, chlorine-, methoxy-, or ethoxy-substituted methyl, ethyl, or n- or i-propyl,
$R^2$ represents optionally cyano-, fluorine-, chlorine-, methoxy-, ethoxy-, or n- or i-propoxy-substituted methyl, ethyl, or n- or i-propyl,
$R^3$ represents hydrogen, fluorine, or chlorine; or represents optionally fluorine- or chlorine-substituted methyl or ethyl,
$R^4$ represents hydrogen, fluorine, or chlorine,
$R^5$ represents cyano, carbamoyl, thiocarbamoyl, fluorine, chlorine, or bromine; or represents optionally fluorine- or chlorine-substituted methyl, ethyl, methoxy, or ethoxy,
$R^6$ represents hydrogen; represents optionally cyano-, carboxyl-, fluorine-, chlorine-, methoxy-, ethoxy-, n- or i-propoxy-, methylthio-, ethylthio-, methylsulphinyl-, ethylsulphinyl-, methylsulphonyl-, ethylsulphonyl-, acetyl-, propionyl-, n- or i-butyroyl-, methoxycarbonyl-, ethoxycarbonyl-, or n- or i-propoxycarbonyl-substituted methyl, ethyl, n- or i-, -propyl, n-, i-, or s-butyl; represents optionally cyano-, fluorine-, chlorine-, bromine-, methoxy-, ethoxy-, or n- or i-propoxy-substituted acetyl, propionyl, n- or i-butyroyl, methoxycarbonyl, ethoxycarbonyl, n- or i-propoxycarbonyl, methylsulphonyl, ethylsulphonyl, n- or i-propylsulphonyl, or n-, i-, or s-butylsulphonyl; represents optionally fluorine-, chlorine-, or bromine-substituted propenyl, butenyl, propynyl, or butynyl; represents optionally cyano-, fluorine-, chlorine-, methyl-, or ethyl-substituted cyclopropyl, cyclopentyl, cyclohexyl, cyclopropylmethyl, cyclopentylmethyl, cyclohexylmethyl, cyclopropylcarbonyl, cyclopentylcarbonyl, cyclohexylcarbonyl, cyclopropylsulphonyl, cyclopentylsulphonyl, or cyclohexylsulphonyl; represents optionally nitro-, cyano-, fluorine-, chlorine-, bromine-, methyl-, ethyl-, n- or i-propyl-, n-, i-, s-, or t-butyl-, trifluoromethyl-, chlorodifluoromethyl-, fluorodichloromethyl-, methoxy-, ethoxy-, n- or i-propoxy-, difluoromethoxy-, trifluoromethoxy-, chlorodifluoromethoxy-, fluorodichloromethoxy-, methoxycarbonyl-, ethoxycarbonyl-, n- or i-propoxycarbonyl-, or n-, i-, s-, or t-butoxycarbonyl-substituted phenyl, phenylmethyl, phenylethyl, benzoyl, phenylacetyl, phenylsulphonyl, or phenylmethylsulphonyl; or represents optionally nitro-, cyano-, fluorine-, chlorine-, bromine-, methyl-, ethyl-, n- or i-propyl-, n-, i-, s-, or t-butyl-, trifluoromethyl-, chlorodifluoromethyl-, fluorodichloromethyl-, methoxy-, ethoxy-, n- or i-propoxy-, n-, i-, s-, or t-butoxy-, difluoromethoxy-, trifluoromethoxy-, chlorodifluoromethoxy-, fluorodichloromethoxy-, methoxycarbonyl-, ethoxycarbonyl-, n- or i-propoxycarbonyl-, or n-, i-, s-, or t-butoxycarbonyl-substituted heterocyclylcarbonyl, heterocyclylmethylcarbonyl, heterocyclylsulphonyl, or heterocyclylmethylsulphonyl, where the heterocyclyl is selected from the group consisting of furyl, tetrahydrofuryl, thienyl, pyrrolyl, pyrrolinyl, pyrrolidinyl, oxopyrrolidinyl, pyrrolyl, pyrazolyl, oxazolyl, oxazolinyl, oxazolidinyl isoxazolyl, thiazolyl, thiazolinyl, thiazolidinyl, cyanoiminothiazolidinyl, imidazolyl, imidazolinyl, 2-oxo-1,3-diazacyclopentyl (2-oxoimidazolidinyl), triazolyl, oxotriazolinyl, thioxotriazolinyl, pyridinyl, piperidinyl, oxopiperidinyl, 2-oxo-1,3-diazacyclohexyl, morpholinyl, and piperazinyl; and $R^7$ represents methoxycarbonylmethoxy, ethoxycarbonylmethoxy, n- or i-propoxycarbonylmethoxy, n-, i-, s-, or t-butoxycarbonylmethoxy, methoxycarbonylethoxy, ethoxycarbonylethoxy, n- or i-propoxycarbonylethoxy, n-, i-, s-, or t-butoxycarbonylethoxy, methoxycarbonylmethylthio, ethoxycarbonylmethylthio, n- or i-propoxycarbonylmethylthio, n-, i-, s-, or t-butoxycarbonylmethylthio, methoxycarbonylethylthio, ethoxycarbonylethylthio, n- or i-propoxycarbonylethylthio, n-, i-, s-, or t-butoxycarbonylethylthio, propenyloxycarbonylmethoxy, butenyloxycarbonylmethoxy, propenyloxycarbonylethoxy, butenyloxycarbonylethoxy, propenyloxycarbonyl methylthio, butenyloxycarbonylmethylthio, propenyloxycarbonylethylthio, butenyloxycarbonylethylthio, propynyloxycarbonylmethoxy, butynyloxycarbonylmethoxy, propynyloxycarbonylethoxy, butynyloxycarbonylethoxy, propynyloxycarbonylmethylthio, butynyloxycarbonylmethylthio, propynyloxycarbonylethylthio, butynyloxycarbonylethylthio, methylaminocarbonylmethoxy, ethylaminocarbonylethoxy, n- or i-propylaminocarbonylmethoxy, n-, i-, s-, or t-butylaminocarbonylmethoxy, methylaminocarbonylethoxy, ethylaminocarbonylethoxy, n- or i-propylaminocarbonylethoxy, n-, i-, s-, or t-butylaminocarbonylethoxy, methylaminocarbonylmethylthio, ethylaminocarbonylmethylthio, n- or i-propylaminocarbonylmethylthio, n-, i-, s-, or t-butylaminocarbonylmethylthio, methylaminocarbonylethylthio, ethylaminocarbonylethylthio, n- or i-propylaminocarbonylethylthio, n-, i-, s-, or t-butylaminocarbonylethylthio, dimethylaminocarbonylmethoxy, diethylaminocarbonylmethoxy, dimethylaminocarbonylethoxy, diethylaminocarbonylethoxy, dimethylaminocarbonylmethylthio, diethylaminocarbonylmethylthio, dimethylaminocarbonylethylthio, diethylaminocarbonylethylthio, dipropenylaminocarbonylmethoxy, dipropenylaminocarbonylethoxy, dipropenylaminocarbonylmethylthio, dipropenylaminocarbonylethylthio, dipropynylaminocarbonylmethoxy, dipropynylaminocarbonylethoxy, dipropynylaminocarbonylmethylthio, or dipropynylaminocarbonylethylthio; represents hydroxyamino; represents N-methylhydroxyamino, N-ethyl-hydroxyamino, N-n-propylhydroxyamino, N-i-propylhydroxyamino, methoxyamino, ethoxyamino, n- or i-propoxyamino, n-, i-, s-, or t-butoxyamino, N-methylmethoxyamino, N-ethylmethoxyamino, N-methylethoxyamino, methoxycarbonylmethoxyamino, ethoxycarbonylmethoxyamino, n- or i-propoxycarbonylmethoxyamino, methoxycarbonylethoxyamino, ethoxycarbonylethoxyamino, n- or i-propoxycarbonylethoxyamino, N-methylmethoxycarbonylmethoxyamino, N-methylethoxycarbonylmethoxyamino, N-methyl-n-propoxycarbonylmethoxyamino, N-methyl-i-propoxycarbonylmethoxyamino, N-methylmethoxycarbonylethoxyamino, N-methylethoxycarbonylethoxyamino, N-methyl-n-propoxycarbonylethoxyamino, N-methyl-i-propoxycarbonylethoxyamino, propenyloxyamino, butenyloxyamino, N-methylpropenyloxyamino, N-methylbutenyloxyamino, N-propenylmethoxyamino, N-propenylethoxyamino, N-propenyl-n-propoxyamino, N-propenyl-i-propoxyamino, N-propenylpropenyloxyamino; represents phenoxyamino or N-methylphenoxyamino; represents cyanoethylamino, cyanopropylamino, or cyanobutylamino; represents dimethylamino, diethylamino, di-n-propylamino, di-i-propylamino, di-n-butylamino, or di-i-butylamino; represents N-methylcyanoethylamino, N-ethylcyanoethylamino, N-n-propylcyanoethylamino, N-i-propylcyanoethylamino, N-methylfluoroethylamino, N-ethylfluoroethylamino, N-n-propylfluoroethylamino, N-i-propylfluoroethylamino, N-methylmethoxyethylamino, N-ethylmethoxyethylamino, N-methylethoxyethylamino, N-ethylethoxyethylamino, N-methylmethoxycarbonylmethylamino, N-methylethoxycarbonylmethylamino, N-methylmethoxycarbonylethylamino, N-methylethoxycarbonylethylamino, represents N-methyl-N-propenylamino, N-methyl-N-butenylamino, N-ethyl-N-propenylamino, N-ethyl-N-butenylamino, N-propyl-N-propenylamino, N-propyl-N-butenylamino, N-butyl-N-propenylamino, N-butyl-N-butenylamino, N-methyl-N-propynylamino, N-methyl-N-butynylamino, N-ethyl-N-propynylamino, N-ethyl-N-butynylamino, N-propyl-N-propynylamino, N-propyl-N-butynylamino, N-butyl-N-propynylamino, or N-butyl-N-butynylamino; represents dipropenylamino, dibutenylamino, dipropynylamino, or dibutynylamino; represents optionally nitro-, cyano-, fluorine-, chlorine-, bromine-, methyl-, ethyl-, n- or i-propyl-, n-, i-, s-, or t-butyl-, difluoromethyl-, dichloromethyl-, trifluoromethyl-, chlorodifluoromethyl-, fluorodichloromethyl-, methoxy-, ethoxy-, n- or i-propoxy-, n-, i-, s-, or t-butoxy-, difluoromethoxy-, trifluoromethoxy-, chlorodifluoromethoxy-, methylthio-, ethylthio-, n- or i-propylthio-, n-, i-, s-, or t-butylthio-, difluoromethylthio-, trifluoromethylthio-, chlorodifluoromethylthio-, methoxycarbonyl-, ethoxycarbonyl-, n- or i-propoxycarbonyl-, n-, i-, s-, or t-butoxycarbonyl-, cyclopropyl-, cyclobutyl-, cyclopentyl-, cyclohexyl-, or phenyl-substituted heterocyclyloxy, heterocyclylthio, heterocyclylamino, N-methylheterocyclylamino, N-methylheterocyclylmethylamino, or —N=(heterocyclyl), where the heterocyclyl is selected from the group consisting of furyl, tetrahydrofuryl, thienyl, pyrrolyl, pyrrolinyl, pyrrolidinyl, oxopyrrolidinyl, pyrrolyl, pyrazolyl, oxazolyl, oxazolinyl, oxazolidinyl, isoxazolyl, thiazolyl, thiazolinyl, thiazolidinyl, cyanoiminothiazolidinyl, imidazolyl, imidazolinyl, 2-oxo-1,3-diazacyclopentyl (2-oxoimidazolidinyl), triazolyl, oxotriazolinyl, thioxotriazolinyl, pyridinyl, piperidinyl, oxopiperidinyl, 2-oxo-1,3-diazacyclohexyl, morpholinyl, piperazinyl, and pyrimidinyl; represents a monocyclic or bicyclic nitrogen heterocycle selected from the group consisting of pyrrolyl, pyrrolinyl, pyrrolidinyl, oxopyrrolidinyl, pyrazolyl, imidazolyl, imidazolinyl, 2-oxo-1,3-diazacyclopentyl (2-oxoimidazolidinyl), 2-oxo-1,3-oxazacyclopentyl (2-oxooxazolidinyl), isoxazolidinyl, thiazolinyl, 2-oxothiazolidinyl, 1,1-dioxoisothiazolidinyl, 2-cyanoiminothiazolidinyl, triazolyl, oxotriazolinyl, thioxotriazolinyl, pyridinyl, piperidinyl, oxopiperidinyl, 2-oxo-1,3-diazacyclohexyl, morpholinyl, and piperazinyl, each of which is attached via N and is optionally substituted by nitro, cyano, fluorine, chlorine, bromine, methyl, ethyl, n- or i-propyl, n-, i-, s-, or t-butyl, difluoromethyl, dichloromethyl, trifluoromethyl, chlorodifluoromethyl, fluorodichloromethyl, methoxy, ethoxy, n- or i-propoxy, n-, i-, s-, or t-butoxy, difluoromethoxy, trifluoromethoxy, chlorodifluoromethoxy, methylthio, ethylthio, n- or i-propylthio, n-, i-, s-, or t-butylthio, difluoromethylthio, trifluoromethylthio, chlorodifluoromethylthio, methoxycarbonyl, ethoxycarbonyl, n- or i-propoxycarbonyl, n-, i-, s-, or t-butoxycarbonyl, cyclopropyl, cyclobutyl, cyclopentyl, cyclohexyl, or phenyl.

5. A compound of formula (I) according to claim 1 in which $R^6$ represents hydrogen; or represents optionally fluorine-, chlorine-, methoxy-, or ethoxy-substituted methyl, ethyl, acetyl, methoxycarbonyl, or ethoxycarbonyl.

6. A compound of formula (I) according to claim 1 in which
Q represents oxygen,
$R^1$ represents hydrogen, amino, or methyl,
$R^2$ represents cyano or trifluoromethyl,
$R^3$ represents hydrogen, chlorine, or methyl,
$R^4$ represents hydrogen, fluorine, or chlorine,
$R^5$ represents cyano, thiocarbamoyl, chlorine, bromine, or trifluoromethyl,
$R^6$ represents hydrogen; represents optionally cyano-, fluorine-, chlorine-, methoxy-, ethoxy-, methylthio-, ethylthio-, methylsulphinyl-, ethylsulphinyl-, methylsulphonyl-, ethylsulphonyl-, acetyl-, propionyl-, methoxycarbonyl-, or ethoxycarbonyl-substituted methyl or ethyl; represents optionally cyano-, fluorine-, chlorine-, bromine-, methoxy-, or ethoxy-substituted acetyl, propionyl, methoxycarbonyl, or ethoxycarbonyl; represents optionally fluorine- or chlorine-substituted methylsulphonyl or ethylsulphonyl; represents optionally fluorine- or chlorine-substituted propenyl, butenyl, propynyl, or butynyl; represents optionally fluorine-, chlorine-, or methyl-substituted cyclopropyl, cyclopropylmethyl, cyclopropylcarbonyl, or cyclopropylsulphonyl; represents optionally nitro-, cyano-, fluorine-, chlorine-, bromine-, methyl-, ethyl-, n- or i-propyl-, n-, i-, s-, or t-butyl-, trifluoromethyl-, chlorodifluoromethyl-, fluorodichloromethyl-, methoxy-, ethoxy-, n- or i-propoxy-, difluoromethoxy-, trifluoromethoxy-, chlorodifluoromethoxy-, fluorodichloromethoxy-, methoxycarbonyl-, ethoxycarbonyl-, or n- or i-propoxycarbonyl-substituted phenyl, phenylmethyl, phenylethyl, benzoyl, phenylacetyl, phenylsulphonyl, or phenylmethylsulphonyl; or represents optionally nitro-, cyano-, fluorine-, chlorine-, bromine-, methyl-, ethyl-, n- or i-propyl-, n-, i-, s-, or t-butyl-, trifluoromethyl-, chlorodifluoromethyl-, fluorodichloromethyl-, methoxy-, ethoxy-, n- or i-propoxy-, n-, i-, s- or t-butoxy-, difluoromethoxy-, trifluoromethoxy-, chlorodifluoromethoxy-, fluorodichloromethoxy-, methoxycarbonyl-, ethoxycarbonyl-, n- or i-propoxycarbonyl-, or n-, i-, s-, or t-butoxycarbonyl-substituted heterocyclylcarbonyl, heterocyclylmethylcarbonyl, heterocyclylsulphonyl, or heterocyclylmethylsulphonyl, where the heterocyclyl is selected from the group consisting of furyl, tetrahydrofuryl, thienyl, pyrrolyl, pyrrolinyl, pyrrolidinyl, oxopyrrolidinyl, pyrrolyl, pyrazolyl, oxazolyl, oxazolinyl, oxazolidinyl, isoxazolyl, thiazolyl, thiazolinyl, thiazolidinyl, cyanoiminothiazolidinyl, imidazolyl, imidazolinyl, 2-oxo-1,3-diazacyclopentyl (2-oxoimidazolidinyl), triazolyl, oxotriazolinyl, thioxotriazolinyl, pyridinyl, piperidinyl, oxopiperidinyl, 2-oxo-1,3-diazacyclohexyl, morpholinyl, and piperazinyl, and
$R^7$ represents methoxycarbonylmethoxy, ethoxycarbonylmethoxy, n- or i-propoxycarbonylmethoxy, n-, i-, s-, or t-butoxycarbonylmethoxy, methoxycarbonylethoxy, ethoxycarbonylethoxy, n- or i-propoxycarbonylethoxy, n-, i-, s-, or t-butoxycarbonylethoxy, methoxycarbonylmethylthio, ethoxycarbonylmethylthio, n- or i-propoxycarbonylmethylthio, n-, i-, s-, or t-butoxycarbonyl-methylthio, methoxycarbonylethylthio, ethoxycarbonylethylthio, n- or i-propoxycarbonylethylthio, n-, i-, s-, or t-butoxycarbonylethylthio, propenyloxycarbonylmethoxy, butenyloxycarbonylmethoxy, propenyloxycarbonylethoxy, butenyloxycarbonylethoxy, propenyloxycarbonylmethylthio, butenyloxycarbonylmethylthio, propenyloxycarbonylethylthio, butenyloxycarbonylethylthio, propynyloxycarbonylmethoxy, butynyloxycarbonylmethoxy, propynyloxycarbonylethoxy, butynyloxycarbonylethoxy, propynyloxycarbonylmethylthio, butynyloxycarbonylmethylthio, propynyloxycarbonylethylthio, butynyloxycarbonylethylthio, methylaminocarbonylmethoxy, ethylaminocarbonylethoxy, n- or i-propylaminocarbonylmethoxy, n-, i-, s-, or t-butylaminocarbonylmethoxy, methylaminocarbonylethoxy, ethylaminocarbonylethoxy, n- or i-propylaminocarbonylethoxy, n-, i-, s- or t-butylaminocarbonylethoxy, methylaminocarbonylmethylthio, ethylaminocarbonylmethylthio, n- or i-propylaminocarbonylmethylthio, n-, i-, s-, or t-butylaminocarbonylmethylthio, methylaminocarbonylethylthio, ethylaminocarbonylethylthio, n- or i-propylaminocarbonylethylthio, n-, i-, s-, or t-butylaminocarbonylethylthio, dimethylaminocarbonylmethoxy, diethylaminocarbonylmethoxy, dimethylaminocarbonylethoxy, diethylaminocarbonylethoxy, dimethylaminocarbonylmethylthio, diethylaminocarbonylmethylthio, dimethylaminocarbonylethylthio, diethylaminocarbonylethylthio, dipropenylaminocarbonylmethoxy, dipropenylaminocarbonylethoxy, dipropenylaminocarbonylmethylthio, dipropenylaminocarbonylethylthio, dipropynylaminocarbonylmethoxy, dipropynylaminocarbonylethoxy, dipropynylaminocarbonylmethylthio, or dipropynylaminocarbonylethylthio.

7. A compound of formula (I) according to claim 1 in which
Q represents oxygen,
$R^1$ represents hydrogen, amino, or methyl,
$R^2$ represents cyano or trifluoromethyl,
$R^3$ represents hydrogen, chlorine, or methyl,
$R^4$ represents hydrogen, fluorine, or chlorine,
$R^5$ represents cyano, thiocarbamoyl, chlorine, bromine, or trifluoromethyl,
$R^6$ represents hydrogen; represents optionally cyano-, fluorine-, chlorine-, methoxy-, ethoxy-, methylthio-, ethylthio-, methylsulphinyl-, ethylsulphinyl-, methylsulphonyl-, ethylsulphonyl-, acetyl-, propionyl-, methoxycarbonyl-, or ethoxycarbonyl-substituted methyl or ethyl; represents optionally cyano-, fluorine-, chlorine-, bromine-, methoxy-, or ethoxy-substituted acetyl, propionyl, methoxycarbonyl, or ethoxycarbonyl; represents optionally fluorine- or chlorine-substituted methylsulphonyl or ethylsulphonyl; represents optionally fluorine- or chlorine-substituted propenyl, butenyl, propynyl, or butynyl; represents optionally fluorine-, chlorine-, or methyl-substituted cyclopropyl, cyclopropylmethyl, cyclopropylcarbonyl, or cyclopropylsulphonyl; represents optionally nitro-, cyano-, fluorine-, chlorine-, bromine-, methyl-, ethyl-, n- or i-propyl-, n-, i-, s-, or t-butyl-, trifluoromethyl-, chlorodifluoromethyl-, fluorodichloromethyl-, methoxy-, ethoxy-, n- or i-propoxy-, difluoromethoxy-, trifluoromethoxy-, chlorodifluoromethoxy-, fluorodichloromethoxy-, methoxycarbonyl-, ethoxycarbonyl-, or n- or i-propoxycarbonyl-substituted phenyl, phenylmethyl, phenylethyl, benzoyl, phenylacetyl, phenylsulphonyl, or phenylmethylsulphonyl; or represents optionally nitro-, cyano-, fluorine-, chlorine-, bromine-, methyl-, ethyl-, n- or i-propyl-, n-, i-, s-, or t-butyl-, trifluoromethyl-, chlorodifluoromethyl-, fluorodichloromethyl-, methoxy-, ethoxy-, n- or i-propoxy-, n-, i-, s-, or t-butoxy-, difluoromethoxy-, trifluoromethoxy-, chlorodifluoromethoxy-, fluorodichloromethoxy-, methoxycarbonyl-, ethoxycarbonyl-, n- or i-propoxycarbonyl-, or n-, i-, s-, or t-butoxycarbonyl-substituted heterocyclylcarbonyl, heterocyclylmethylcarbonyl, heterocyclylsulphonyl, or heterocyclylmethylsulphonyl, where the heterocyclyl is selected from the group consisting of furyl, tetrahydrofuryl, thienyl, pyrrolyl, pyrrolinyl, pyrrolidinyl, oxopyrrolidinyl, pyrrolyl, pyrazolyl, oxazolyl, oxazolinyl, oxazolidinyl, isoxazolyl, thiazolyl, thiazolinyl, thiazolidinyl, cyanoiminothiazolidinyl, imidazolyl, imidazolinyl, 2-oxo-1,3-diazacyclopentyl (2-oxoimidazolidinyl), triazolyl, oxotriazolinyl, thioxotriazolinyl, pyridinyl, piperidinyl, oxopiperidinyl, 2-oxo-1,3-diazacyclohexyl, morpholinyl, and piperazinyl, and $R^7$ represents hydroxyamino; represents N-methylhydroxyamino, N-ethylhydroxyamino, N-n-propylhydroxyamino, N-i-propylhydroxyamino, methoxyamino, ethoxyamino, n- or i-propoxyamino, n-, i-, s-, or t-butoxyamino, N-methylmethoxyamino, N-ethylmethoxyamino, N-methylethoxyamino, methoxycarbonylmethoxyamino, ethoxycarbonylmethoxyamino, n- or i-propoxycarbonylethoxyamino, methoxycarbonylethoxyamino, ethoxycarbonylethoxyamino, n- or i-propoxycarbonylethoxyamino, N-methylmethoxycarbonylmethoxyamino, N-methylethoxycarbonylmethoxyamino, N-methyl-n-propoxycarbonylmethoxyamino, N-methyl-i-propoxycarbonylmethoxyamino, N-methylmethoxycarbonylethoxyamino, N-methylethoxycarbonylethoxyamino, N-methyl-n-propoxycarbonylethoxyamino, N-methyl-i-propoxycarbonylethoxyamino, propenyloxyamino, butenyloxyamino, N-methylpropenyloxyamino, N-methylbutenyloxyamino, N-propenylmethoxyamino, N-propenylethoxyamino, N-propenyl-n-propoxyamino, N-propenyl-i-propoxyamino, or N-propenylpropenyloxyamino; or represents phenoxyamino or N-methylphenoxyamino.

8. A compound of formula (I) according to claim 1 in which
Q represents oxygen,
$R^1$ represents hydrogen, amino, or methyl,
$R^2$ represents cyano or trifluoromethyl,
$R^3$ represents hydrogen, chlorine, or methyl,
$R^4$ represents hydrogen, fluorine, or chlorine,
$R^5$ represents cyano, thiocarbamoyl, chlorine, bromine, or trifluoromethyl,
$R^6$ represents hydrogen; represents optionally cyano-, fluorine-, chlorine-, methoxy-, ethoxy-, methylthio-, ethylthio-, methylsulphinyl-, ethylsulphinyl-, methylsulphonyl-, ethylsulphonyl-, acetyl-, propionyl-, methoxycarbonyl-, or ethoxycarbonyl-substituted methyl or ethyl; represents optionally cyano-, fluorine-, chlorine-, bromine-, methoxy-, or ethoxy-substituted acetyl, propionyl, methoxycarbonyl, or ethoxycarbonyl; represents optionally fluorine- or chlorine-substituted methylsulphonyl or ethylsulphonyl; represents optionally fluorine- or chlorine-substituted propenyl, butenyl, propynyl, or butynyl; represents optionally fluorine-, chlorine-, or methyl-substituted cyclopropyl, cyclopropylmethyl, cyclopropylcarbonyl, or cyclopropylsulphonyl; represents optionally nitro-, cyano-, fluorine-, chlorine-, bromine-, methyl-, ethyl-, n- or i-propyl-, n-, i-, s-, or t-butyl-, trifluoromethyl-, chlorodifluoromethyl-, fluorodichloromethyl-, methoxy-, ethoxy-, n- or i-propoxy-, difluoromethoxy-, trifluoromethoxy-, chlorodifluoromethoxy-, fluorodichloromethoxy-, methoxycarbonyl-, ethoxycarbonyl-, or n- or i-propoxycarbonyl-substituted phenyl, phenylmethyl, phenylethyl, benzoyl, phenylacetyl, phenylsulphonyl, or phenylmethylsulphonyl; or represents optionally nitro-, cyano-, fluorine-, chlorine-, bromine-, methyl-, ethyl-, n- or i-propyl-, n-, i-, s-, or t-butyl-, trifluoromethyl-, chlorodifluoromethyl-, fluorodichloromethyl-, methoxy-, ethoxy-, n- or i-propoxy-, n-, i-, s-, or t-butoxy-, difluoromethoxy-, trifluoromethoxy-, chlorodifluoromethoxy-, fluorodichloromethoxy, methoxycarbonyl-, ethoxycarbonyl-, n- or i-propoxycarbonyl-, or n-, i-, s-, or t-butoxycarbonyl-substituted heterocyclylcarbonyl, heterocyclylmethylcarbonyl, heterocyclylsulphonyl, or heterocyclylmethylsulphonyl, where the heterocyclyl is selected from the group consisting of furyl, tetrahydrofuryl, thienyl, pyrrolyl, pyrrolinyl, pyrrolidinyl, oxopyrrolidinyl, pyrrolyl, pyrazolyl, oxazolyl, oxazolinyl, oxazolidinyl, isoxazolyl, thiazolyl, thiazolinyl, thiazolidinyl, cyanoiminothiazolidinyl, imidazolyl, imidazolinyl, 2-oxo-1,3-diaza-cyclopentyl (2-oxoimidazolidinyl), triazolyl, oxotriazolinyl, thioxotriazolinyl, pyridinyl, piperidinyl, oxopiperidinyl, 2-oxo-1,3-diazacyclohexyl, morpholinyl, and piperazinyl, and $R^7$ represents cyanoethylamino, cyanopropylamino, or cyanobutylamino; represents dimethylamino, diethylamino, di-n-propylamino, di-i-propylamino, di-n-butylamino, or di-i-butylamino; represents N-methylcyanoethylamino, N-ethylcyanoethylamino, N-n-propylcyanoethylamino, N-i-propylcyanoethylamino, N-methylfluoroethylamino, N-ethylfluoroethylamino, N-n-propylfluoroethylamino, N-i-propylfluoroethylamino, N-methylmethoxyethylamino, N-ethylmethoxyethylamino, N-methylethoxyethylamino, N-ethylethoxyethylamino, N-methylmethoxycarbonylmethylamino, N-methylethoxycarbonylmethylamino, N-methylmethoxycarbonylethylamino, N-methylethoxycarbonylethylamino, represents N-methyl-N-propenylamino, N-methyl-N-butenylamino, N-ethyl-N-propenylamino, N-ethyl-N-butenylamino, N-propyl-N-propenylamino, N-propyl-N-butenylamino, N-butyl-N-propenylamino, N-butyl-N-butenylamino, N-methyl-N-propynylamino, N-methyl-N-butynylamino, N-ethyl-N-propynylamino, N-ethyl-N-butynylamino, N-propyl-N-propynylamino, N-propyl-N-butynylamino, N-butyl-N-propynylamino, or N-butyl-N-butynylamino; or represents dipropenylamino, dibutenylamino, dipropynylamino, or dibutynylamino.

9. A compound of formula (I) according to claim 1 in which
Q represents oxygen,
$R^1$ represents hydrogen, amino, or methyl,
$R^2$ represents cyano or trifluoromethyl,
$R^3$ represents hydrogen, chlorine, or methyl,
$R^4$ represents hydrogen, fluorine, or chlorine,
$R^5$ represents cyano, thiocarbamoyl, chlorine, bromine, or trifluoromethyl,
$R^6$ represents hydrogen; represents optionally cyano-, fluorine-, chlorine-, methoxy-, ethoxy-, methylthio-, ethylthio-, methylsulphinyl-, ethylsulphinyl-, methylsulphonyl-, ethylsulphonyl-, acetyl-, propionyl-, methoxycarbonyl-, or ethoxycarbonyl-substituted methyl or ethyl; represents optionally cyano-, fluorine-, chlorine-, bromine-, methoxy-, or ethoxy-substituted acetyl, propionyl, methoxycarbonyl, or ethoxycarbonyl; represents optionally fluorine- or chlorine-substituted methylsulphonyl or ethylsulphonyl; represents optionally fluorine- or chlorine-substituted propenyl, butenyl, propynyl, or butynyl; represents optionally fluorine-, chlorine-, or methyl-substituted cyclopropyl, cyclopropylmethyl, cyclopropylcarbonyl, or cyclopropylsulphonyl; represents optionally nitro-, cyano-, fluorine-, chlorine-, bromine-, methyl-, ethyl-, n- or i-propyl-, n-, i-, s-, or t-butyl-, trifluoromethyl-, chlorodifluoromethyl-, fluorodichloromethyl-, methoxy-, ethoxy-, n- or i-propoxy-, difluoromethoxy-, trifluoromethoxy-, chlorodifluoromethoxy-, fluorodichloromethoxy-, methoxycarbonyl-, ethoxycarbonyl-, or n- or i-propoxycarbonyl-substituted phenyl, phenylmethyl, phenylethyl, benzoyl, phenylacetyl, phenylsulphonyl, or phenylmethylsulphonyl; or represents optionally nitro-, cyano-, fluorine-, chlorine-, bromine-, methyl-, ethyl-, n- or i-propyl-, n-, i-, s-, or t-butyl-, trifluoromethyl-, chlorodifluoromethyl-, fluorodichloromethyl-, methoxy-, ethoxy-, n- or i-propoxy-, n-, i-, s-, or t-butoxy-, difluoromethoxy-, trifluoromethoxy-, chlorodifluoromethoxy-, fluorodichloromethoxy-, methoxycarbonyl-, ethoxycarbonyl-, n- or i-propoxycarbonyl-, or n-, i-, s-, or t-butoxycarbonyl-substituted heterocyclylcarbonyl, heterocyclylmethylcarbonyl, heterocyclylsulphonyl, or heterocyclylmethylsulphonyl, where the heterocyclyl is selected from the group consisting of furyl, tetrahydrofuryl, thienyl, pyrrolyl, pyrrolinyl, pyrrolidinyl, oxopyrrolidinyl, pyrrolyl, pyrazolyl, oxazolyl, oxazolinyl, oxazolidinyl, isoxazolyl, thiazolyl, thiazolinyl, thiazolidinyl, cyanoiminothiazolidinyl, imidazolyl, imidazolinyl, 2-oxo-1,3-diazacyclopentyl (2-oxoimidazolidinyl), triazolyl, oxotriazolinyl, thioxotriazolinyl, pyridinyl, piperidinyl, oxopiperidinyl, 2-oxo-1,3-diazacyclohexyl, morpholinyl, and piperazinyl, and $R^7$ represents optionally nitro-, cyano-, fluorine-, chlorine-, bromine-, methyl-, ethyl-, n- or i-propyl-, n-, i-, s-, or t-butyl-, difluoromethyl-, dichloromethyl-, trifluoromethyl-, chlorodifluoromethyl-, fluorodichloromethyl-, methoxy-, ethoxy-, n- or i-propoxy-, n-, i-, s-, or t-butoxy-, difluoromethoxy-, trifluoromethoxy-, chlorodifluoromethoxy-, methylthio-, ethylthio-, n- or i-propylthio-, n-, i-, s-, or t-butylthio-, difluoromethylthio-, trifluoromethylthio-, chlorodifluoromethylthio-, methoxycarbonyl-, ethoxycarbonyl-, n- or i-propoxycarbonyl-, n-, s-, or t-butoxycarbonyl-, cyclopropyl-, cyclobutyl-, cyclopentyl-, cyclohexyl-, or phenyl-substituted heterocyclyloxy, heterocyclylthio, heterocyclylamino, N-methylheterocyclylamino, N-methylheterocyclylmethylamino, or —N=(heterocyclyl), where the heterocyclyl is selected from the group consisting of furyl, tetrahydrofuryl, thienyl, pyrrolyl, pyrrolinyl, pyrrolidinyl, oxopyrrolidinyl, pyrrolyl, pyrazolyl, oxazolyl, oxazolinyl, oxazolidinyl, isoxazolyl, thiazolyl, thiazolinyl, thiazolidinyl, cyanoiminothiazolidinyl, imidazolyl, imidazolinyl, 2-oxo-1,3-diazacyclopentyl (2-oxoimidazolidinyl), triazolyl, oxotriazolinyl, thioxotriazolinyl, pyridinyl, piperidinyl, oxopiperidinyl, 2-oxo-1,3-diazacyclohexyl, morpholinyl, piperazinyl, and pyrimidinyl.

10. A compound of formula (I) according to claim 1 in which

Q represents oxygen, $R^1$ represents hydrogen, amino, or methyl, $R^2$ represents cyano or trifluoromethyl, $R^3$ represents hydrogen, chlorine, or methyl, $R^4$ represents hydrogen, fluorine, or chlorine, $R^5$ represents cyano, thiocarbamoyl, chlorine, bromine, or trifluoromethyl, $R^6$ represents hydrogen; represents optionally cyano-, fluorine-, chlorine-, methoxy-, ethoxy-, methylthio-, ethylthio-, methylsulphinyl-, ethylsulphinyl-, methylsulphonyl-, ethylsulphonyl-, acetyl-, propionyl-, methoxycarbonyl-, or ethoxycarbonyl-substituted methyl or ethyl; represents optionally cyano-, fluorine-, chlorine-, bromine-, methoxy-, or ethoxy-substituted acetyl, propionyl, methoxycarbonyl, or ethoxycarbonyl; represents optionally fluorine- or chlorine-substituted methylsulphonyl or ethylsulphonyl; represents optionally fluorine- or chlorine-substituted propenyl, butenyl, propynyl, or butynyl; represents optionally fluorine-, chlorine-, or methyl-substituted cyclopropyl, cyclopropylmethyl, cyclopropylcarbonyl, or cyclopropylsulphonyl; represents optionally nitro-, cyano-, fluorine-, chlorine-, bromine-, methyl-, ethyl-, n- or i-propyl-, n-, i-, s-, or t-butyl-, trifluoromethyl-, chlorodifluoromethyl-, fluorodichloromethyl-, methoxy-, ethoxy-, n- or i-propoxy-, difluoromethoxy-, trifluoromethoxy-, chlorodifluoromethoxy-, fluorodichloromethoxy-, methoxycarbonyl-, ethoxycarbonyl-, or n- or i-propoxycarbonyl-substituted phenyl, phenylmethyl, phenylethyl, benzoyl, phenylacetyl, phenylsulphonyl, or phenylmethylsulphonyl; or represents optionally nitro-, cyano-, fluorine-, chlorine-, bromine-, methyl-, ethyl-, n- or i-propyl-, n-, i-, s-, or t-butyl-, trifluoromethyl-, chlorodifluoromethyl-, fluorodichloromethyl-, methoxy-, ethoxy-, n- or i-propoxy-, n-, i-, s-, or t-butoxy-, difluoromethoxy-, trifluoromethoxy-, chlorodifluoromethoxy-, fluorodichloromethoxy-, methoxycarbonyl-, ethoxycarbonyl-, n- or i-propoxycarbonyl-, or n-, i-, s-, or t-butoxycarbonyl-substituted heterocyclylcarbonyl, heterocyclylmethylcarbonyl, heterocyclylsulphonyl, or heterocyclylmethylsulphonyl, where the heterocyclyl is selected from the group consisting of furyl, tetrahydrofuryl, thienyl, pyrrolyl, pyrrolinyl, pyrrolidinyl, oxopyrrolidinyl, pyrrolyl, pyrazolyl, oxazolyl, oxazolinyl, oxazolidinyl, isoxazolyl, thiazolyl, thiazolinyl, thiazolidinyl, cyanoiminothiazolidinyl, imidazolyl, imidazolinyl, 2-oxo-1,3-diazacyclopentyl (2-oxoimidazolidinyl), triazolyl, oxotriazolinyl, thioxotriazolinyl, pyridinyl, piperidinyl, oxopiperidinyl, 2-oxo-1,3-diazacyclohexyl, morpholinyl, and piperazinyl, and $R^7$ represents a monocyclic or bicyclic nitrogen heterocycle selected from the group consisting of pyrrolyl, pyrrolinyl, pyrrolidinyl, oxopyrrolidinyl, pyrazolyl, imidazolyl, imidazolinyl, 2-oxo-1,3-diazacyclopentyl (2-oxo-imidazolidinyl), 2-oxo-1,3-oxazacyclopentyl (2-oxooxazolidinyl), isoxazolidinyl, thiazolinyl, 2-oxothiazolidinyl, 1,1-dioxoisothiazolidinyl, 2-cyanoiminothiazolidinyl, triazolyl, oxotriazolinyl, thioxotriazolinyl, pyridinyl, piperidinyl, oxopiperidinyl, 2-oxo-1,3-diazacyclohexyl, morpholinyl, and piperazinyl, each of which is attached via N and is optionally substituted by nitro, cyano, fluorine, chlorine, bromine, methyl, ethyl, n- or i-propyl, n-, i-, s-, or t-butyl, difluoromethyl, dichloromethyl, trifluoromethyl, chlorodifluoromethyl, fluorodichloromethyl, methoxy, ethoxy, n- or i-propoxy, n-, i-, s-, or t-butoxy, difluoromethoxy, trifluoromethoxy, chlorodifluoromethoxy, methylthio, ethylthio, n- or i-propylthio, n-, i-, s-, or t-butylthio, difluoromethylthio, trifluoromethylthio, chlorodifluoromethylthio, methoxycarbonyl, ethoxycarbonyl, n- or i-propoxycarbonyl, n-, i-, s-, or t-butoxycarbonyl, cyclopropyl, cyclobutyl, cyclopentyl, cyclohexyl, or phenyl.

11. A process for preparing compounds of formula (I) according to claim 1 comprising
(a) reacting a compound of formula (II)

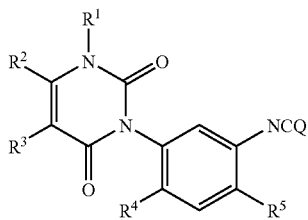

in which Q, $R^1$, $R^2$, $R^3$, $R^4$, and $R^5$ are as defined for formula (I) in claim 1,
with a compound of formula (III)

H—$R^7$   (III)

in which $R^7$ is as defined for formula (I) in claim 1, optionally in the presence of one or more reaction auxiliaries and optionally in the presence of one or more diluents, to form a compound of formula (Ia)

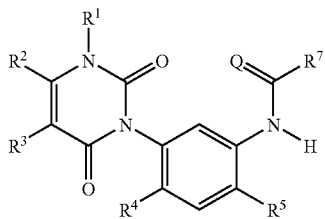

in which Q, $R^1$, $R^2$, $R^3$, $R^4$, $R^5$, and $R^7$ are as defined for formula (I) in claim 1, and
(b) optionally reacting the compound of formula (Ia) with a compound of formula (IV)

X—$R^6$   (IV)

in which
$R^6$ is as defined as for formula (I) in claim 1 but is not hydrogen, and X represents halogen or represents acetyloxy, propionyloxy, methoxysulphonyloxy, or ethoxysulphonyloxy,
optionally in the presence of one or more reaction auxiliaries and optionally in the presence of one or more diluents.

12. A compound of formula (II)

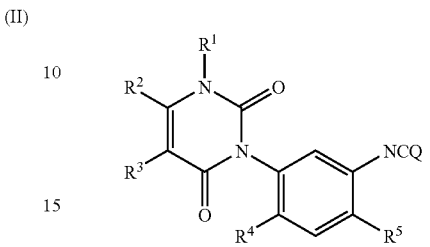

in which
Q represents oxygen,
$R^1$ represents hydrogen or amino; or represents optionally cyano-, halogen-, or $C_1$-$C_4$-alkoxy-substituted alkyl having 1 to 6 carbon atoms,
$R^2$ represents carboxyl, cyano, carbamoyl, or thiocarbamoyl; or represents optionally cyano-, halogen-, or $C_1$-$C_4$-alkoxy-substituted alkyl or alkoxycarbonyl having in each case 1 to 6 carbon atoms in the alkyl groups,
$R^3$ represents hydrogen or halogen; or represents optionally halogen-substituted alkyl having 1 to 6 carbon atoms,
$R^4$ represents hydrogen, cyano, carbamoyl, thiocarbamoyl, or halogen, and
$R^5$ represents cyano, carbamoyl, thiocarbamoyl, or halogen; or represents optionally halogen-substituted alkyl or alkoxy having in each case 1 to 6 carbon atoms.

13. A composition comprising one or more compounds of formula (I) according to claim 1 and one or more extenders and/or surfactants.

14. A method for controlling unwanted plants comprising allowing an effective amount of a compound of formula (I) according to claim 1 to act on the plant and/or its habitat.

15. A method for controlling unwanted plants comprising allowing an effective amount of a composition according to claim 13 to act on the plant and/or its habitat.

* * * * *